United States Patent [19]

Sasaki et al.

[11] Patent Number: 5,627,287
[45] Date of Patent: May 6, 1997

[54] PHTHALIDE COMPOUND AND A NEAR INFRARED ABSORBER AND A RECORDING MATERIAL EACH COMPRISING THE SAME COMPOUND

[75] Inventors: Hiroyuki Sasaki; Shinzo Nawamoto; Jun-ichi Taniguchi; Toshihiro Masaoka; Bunji Sawano; Sayuri Wada; Yojiro Kumagae, all of Osaka, Japan

[73] Assignee: Yamamoto Chemicals, Inc., Osaka, Japan

[21] Appl. No.: 377,237

[22] Filed: Jan. 24, 1995

[30] Foreign Application Priority Data

Jan. 25, 1994 [JP] Japan .................. 6-006279
Feb. 10, 1994 [JP] Japan .................. 6-037965
Jun. 3, 1994 [JP] Japan .................. 6-145673

[51] Int. Cl.⁶ .................................. C07D 209/14
[52] U.S. Cl. .............................. 548/463; 503/200
[58] Field of Search ............... 548/463; 503/200

[56] References Cited

U.S. PATENT DOCUMENTS

| | | | |
|---|---|---|---|
| 4,016,174 | 4/1977 | Farber | 548/463 X |
| 4,022,771 | 5/1977 | Farber | 260/240 |
| 4,119,776 | 10/1978 | Farber | 542/441 |
| 4,985,345 | 1/1991 | Hayakawa et al. | 430/335 |

FOREIGN PATENT DOCUMENTS

| | | |
|---|---|---|
| 2306987 | 4/1976 | France . |
| 2642363 | 2/1990 | France . |

*Primary Examiner*—Jacqueline Haley
*Attorney, Agent, or Firm*—Birch, Stewart, Kolasch & Birch

[57] ABSTRACT

A phthalide compound of general formula (I) and a near infrared absorber and a recording material each utilizing the phthalide compound are disclosed.

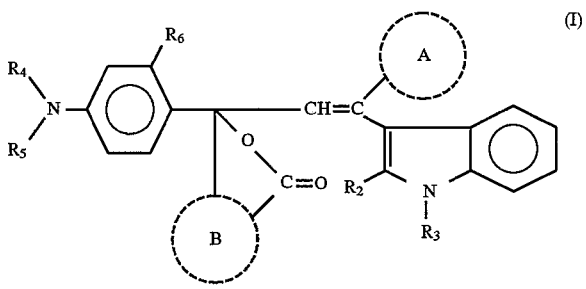

wherein ring A represents a substituent group of the following formula

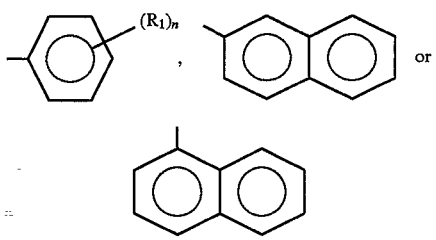

where the other substituents are as defined in the disclosure.

The near infrared absorber and the recorded image on the recording material absorb strongly the near infrared region with no appreciable absorption in the visible region of the spectrum. The near infrared absorber is colorless or pale in color and yet highly capable of absorbing near infrared radiation. The recorded image on the recording material can hardly be read with the eye but can be read with the OCR. Moreover, the effect on the developed shade of any concomitant color former in a recording material is minimal.

19 Claims, 21 Drawing Sheets

F I G. 2 6
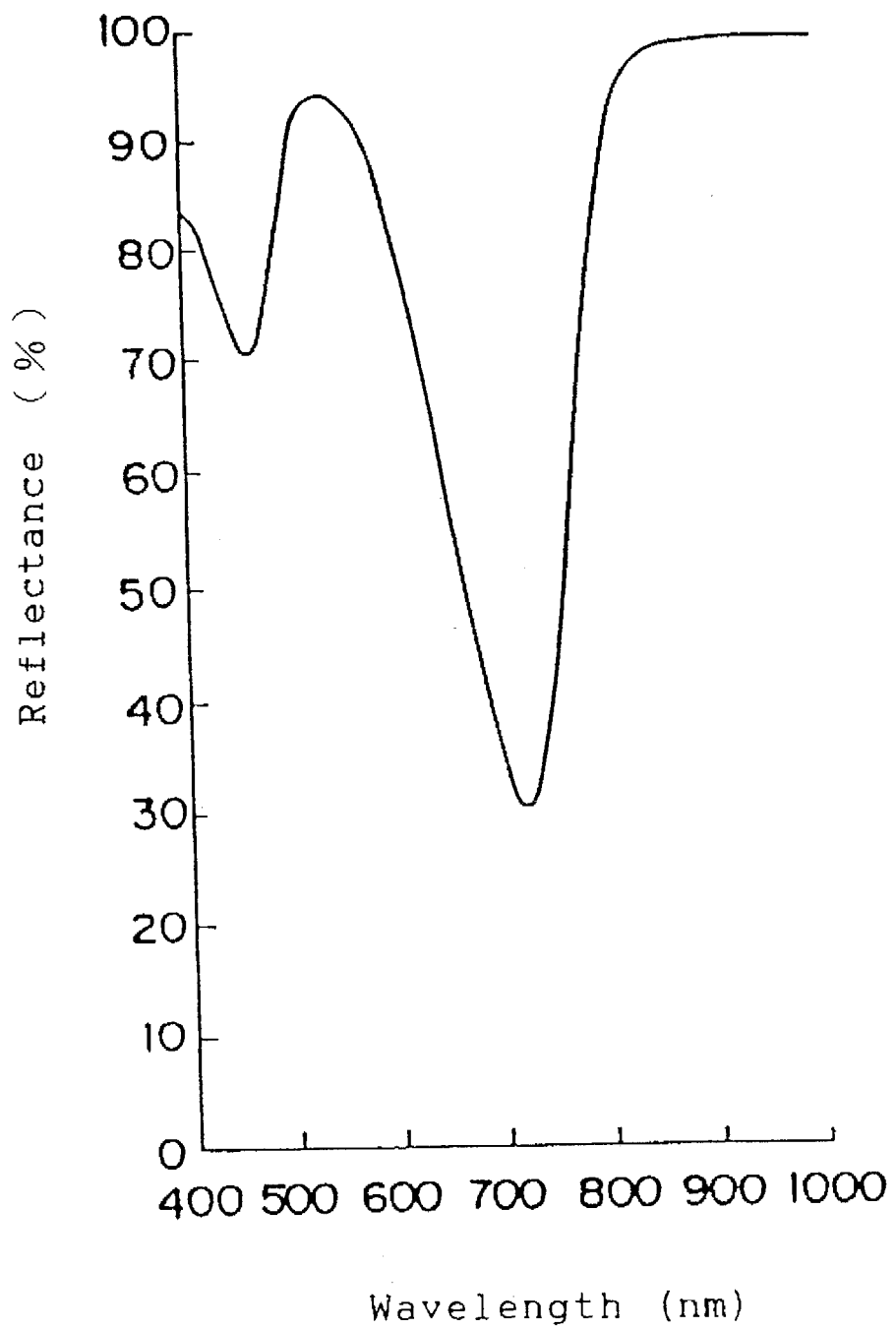

PHTHALIDE COMPOUND AND A NEAR INFRARED ABSORBER AND A RECORDING MATERIAL EACH COMPRISING THE SAME COMPOUND

FIELD OF THE INVENTION

This invention relates to a phthalide compound and a near infrared absorber and a recording material each comprising the same compound. More particularly, the invention relates to a novel phthalide compound and a near infrared absorber and a recording material each absorbing strongly the near infrared region but absorbing little the visible region of the spectrum.

BACKGROUND OF THE INVENTION

Recording materials utilizing the color reaction between an electron-donating color former (hereinafter referred to briefly as a color former) and an electron-accepting developer (hereinafter referred to briefly as a developer) are well known and particularly pressure-sensitive recording materials and thermo-sensitive recording materials are in broad use today.

Recently has increased a need for reading the image recorded on such a pressure-sensitive or thermo-sensitive recording materials with an optical character reader (hereinafter referred to as the OCR) utilizing a light-emitting diode, a semiconductor laser or the like as the light source. In order to read a recorded image with the OCR, it is essential that the image should have an absorption at the emission wavelength of the light source used. While the emission wavelength range of the OCR varies with different light sources used, light sources with emission wavelengths in the range of 650–750 nm are in the focus of current interest and, therefore, the recorded image preferably absorbs this particular wavelength range.

As for color formers providing recorded images absorbing the near infrared region of the spectrum, a number of compounds are already known. For example, as phthalide compounds capable of providing recorded images absorbing the wavelength range of about 650–750 nm, compounds (Compound A, B, C and D) of the following formulas are disclosed in U.S. Pat. No. 4,119,776 at col. 21, lines 36–68 of the specification.

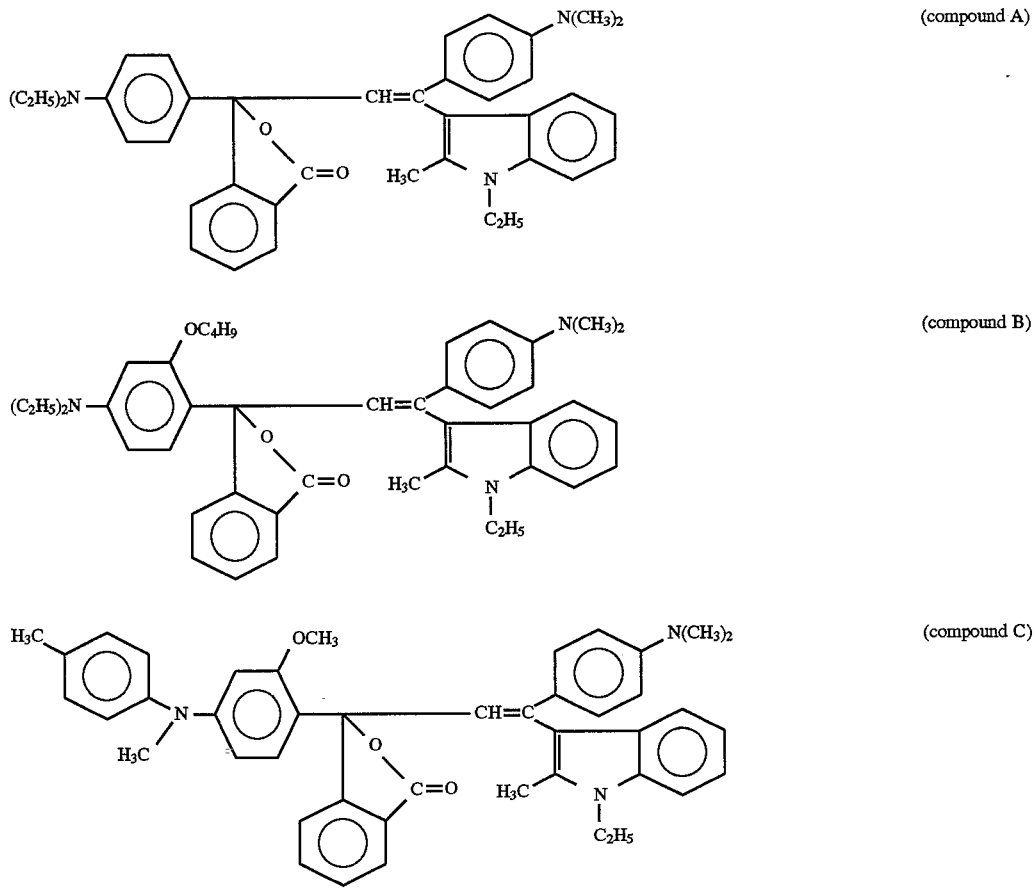

-continued

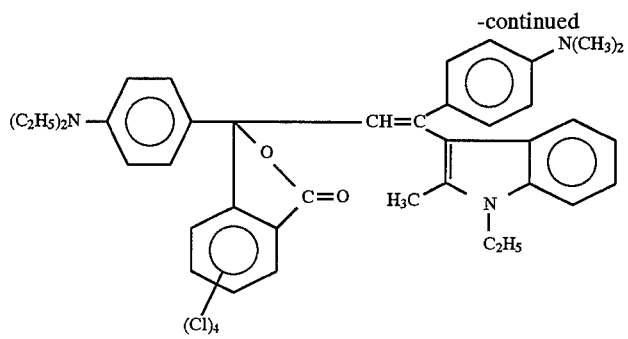

(compound D)

Recording materials utilizing these known phthalide compounds provide recorded images that absorb the visible region as well and are, therefore, blue-bluish green-green in color, thus insuring the advantage that the recorded images are visible to the eye. However, these materials are not satisfactory in applications where visible color development is undesirable. Thus, there are cases in which the recorded image is preferably invisible as it is true with bank customer secret codes or in which the print is preferably inconspicuous for aesthetic reasons as it is true with bar codes. Moreover, when a fluorane compound not absorbing the near infrared region and providing for a black image is used in an OCR-compatible black recording material, the use thereof in combination with any known phthalide compound tends to result in the change of color.

OBJECTS AND SUMMARY OF THE INVENTION

It is an object of this invention to provide a novel phthalide compound that, on reacting with a developer, absorbs strongly the near infrared region of the spectrum but does not absorb at all or absorbs only weakly the visible region.

It is a further object of this invention to provide a near infrared absorber that absorbs strongly the near infrared region but does not absorb at all or absorbs only weakly the visible region, that is to say that, by itself, is close to be colorless or white but absorbs the near infrared region and its uses.

It is a still further object of this invention to provide a recording material of the color former-developer type that provides for a recorded image that is either colorless or of pale color but absorbs strongly the near infrared region and a recording material including other color formers that does not undergo any appreciable change in color and absorbs strongly the near infrared region.

This invention relates, in one aspect, to a phthalide compound of general formula (I) and a process for producing the same compound.

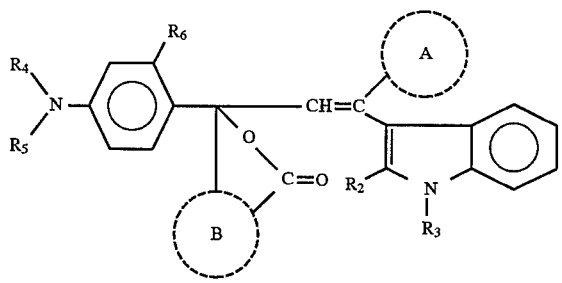

(I)

wherein ring A represents a substituent group of the following structural formula

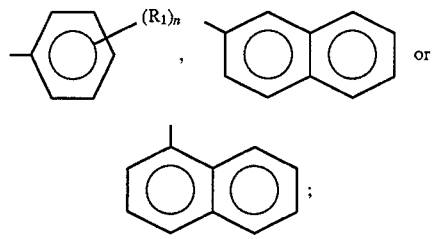

$R_1$ represents hydrogen, alkyl, alkoxy or halogen; n is an integer equal to 1 through 3, inclusive; ring B represents a substituent group of the following structural formula

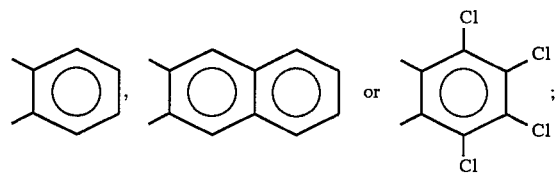

$R_2$ represents alkyl or aryl; $R_3$ represents alkyl; $R_4$ and $R_5$ independently represent alkyl or unsubstituted or substituted phenyl; $R_6$ represents hydrogen, alkyl or alkoxy.

This invention relates, in another aspect, to a near infrared absorber that is obtainable by reacting a phthalide compound of general formula (I) with an electron-accepting compound and a near infrared absorbent composition containing said infrared absorber.

This invention relates, in a further aspect, to a recording material utilizing the reaction between an electron-donating color former and an electron-accepting developer, which utilizes a phthalide compound of general formula (I) as said electron-donating color former.

BRIEF DESCRIPTION OF THE DRAWINGS

FIG. 26 is a reflection spectrum of the sheet of paper coated with the near infrared absorber produced from compound 92 and D-8 as manufactured in Example 71;

FIG. 32 is a reflection spectrum of the sheet of paper coated with the near infrared absorber produced from compound B and bisphenol A as manufactured in Comparison Example 13.

DETAILED DESCRIPTION OF THE INVENTION

Figure 1:
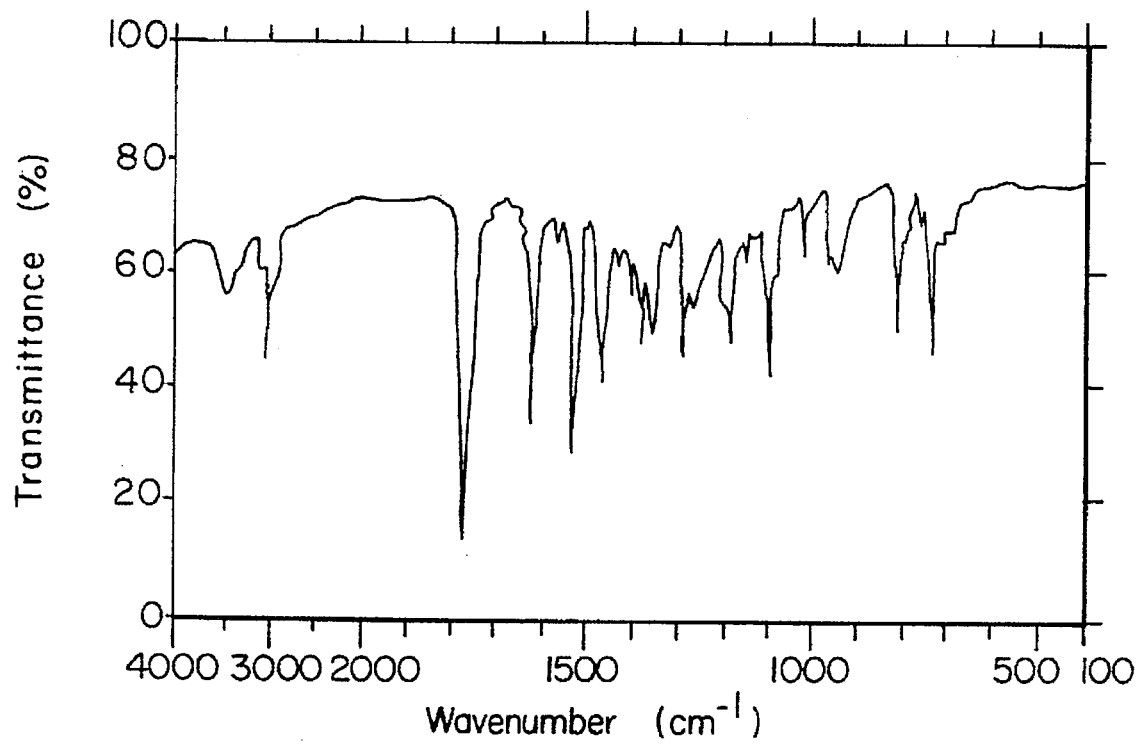
FIG. 1 is an infrared absorption spectrum of compound 1 as synthesized in Example 1.

Referring to the above general formula (I), the alkyl for $R_1$ on ring A is not critical in absorption character but from the standpoint of availability of the starting material, is preferably an alkyl group of 1–8 carbon atoms and, for still better results, a $C_{1-6}$ alkyl group. Thus, $R_1$ may for example be methyl, ethyl, n-propyl, isopropyl, n-butyl, isobutyl, sec-butyl, n-pentyl, isopentyl, n-hexyl, n-heptyl, n-octyl or 2-ethylhexyl. The alkoxy for $R_1$ is preferably a lower alkoxy group of 1–4 carbon atoms and, for still better results, a $C_{1-2}$ alkoxy group. Thus, for example, metoxy, ethoxy, n-propoxy, isopropoxy, n-butoxy, sec-butoxy and isobutoxy can be mentioned. The halogen for $R_1$ is preferably chlorine, bromine or fluorine and, for still better results, chlorine. The integer n is preferably equal to 1 or 2.

The alkyl for $R_2$ is preferably a lower alkyl group of 1–4 carbon atoms and, for still better results, a $C_{1-2}$ alkyl group. Thus, for example, methyl, ethyl, n-propyl and n-butyl can be mentioned. The aryl for $R_2$ is preferably phenyl or substituted phenyl, the preferred substituent of which is alkyl or halogen. Thus, said substituted phenyl may for example be o-tolyl, m-tolyl, p-tolyl, 2,4-xylyl, o-chlorophenyl, m-chlorophenyl or p-chlorophenyl.

$R_3$ is preferably an alkyl group of 1–12 carbon atoms and, for still better results, a $C_{1-8}$ alkyl group. Thus, the alkyl $R_3$ includes methyl, ethyl, n-propyl, isopropyl, n-butyl, isobutyl, n-pentyl, isopentyl, n-hexyl, n-heptyl, n-octyl, 2-ethylhexyl, n-decyl and n-dodecyl, among others.

The alkyl for $R_4$, $R_5$ is preferably an alkyl group of 1–8 carbon atoms and, for still better results, a $C_{1-6}$ alkyl group. Thus, methyl, ethyl, n-propyl, isopropyl, n-butyl, isobutyl, n-pentyl, isopentyl, n-hexyl, n-heptyl, n-octyl and 2-ethylhexyl can be mentioned as examples. The aryl for $R_4$, $R_5$ is preferably phenyl or substituted phenyl as preferably substituted by alkyl, alkoxy or halogen. Thus, said substituted phenyl includes o-tolyl, p-tolyl, m-tolyl, p-ethylphenyl, 2,4-xylyl, o-methoxyphenyl, m-metholxyphenyl, p-methoxyphenyl, p-ethoxyphenyl, o-chlorophenyl, m-chlorophenyl and p-chlorophenyl, among others.

The alkyl for $R_6$ is preferably an alkyl group of 1–4 carbon atoms, thus including methyl, ethyl, n-propyl, n-butyl and so on. The alkoxy for $R_6$ is preferably an alkoxy group of 1–8 carbon atoms and, for still better results, a $C_{1-6}$ alkoxy group. Thus, methoxy, ethoxy, n-propoxy, n-butoxy, n-pentyloxy and n-hexyloxy can be mentioned by way of example.

The preferred combination of these substituents is as follows.

Ring A is

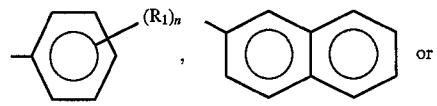

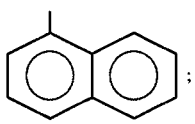

$R_1$ is hydrogen, $C_{1-8}$ alkyl, $C_{1-4}$ alkoxy or halogen; $R_2$ is $C_{1-4}$ alkyl or unsubstituted or substituted phenyl; $R_3$ is $C_{1-12}$ alkyl; $R_4$ and $R_5$ each is $C_{1-8}$ alkyl or unsubstituted or substituted phenyl; $R_6$ is hydrogen, $C_{1-4}$ alkyl or $C_{1-8}$ alkoxy; and ring B is

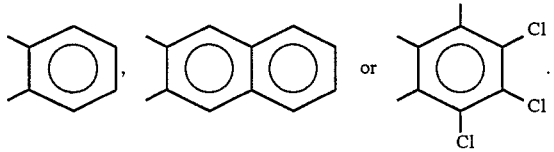

The more desirable combination of the substituents is that ring A is

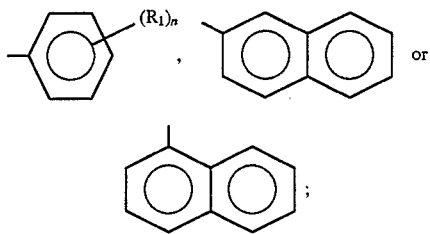

$R_1$ is hydrogen, $C_{1-6}$ alkyl, $C_{1-2}$ alkoxy or chlorine; $R_2$ is $C_{1-2}$ alkyl or phenyl; $R_3$ is $C_{1-8}$ alkyl; $R_4$ and $R_5$ each is $C_{1-6}$ alkyl or unsubstituted or substituted phenyl; $R_6$ is hydrogen, $C_{1-4}$ alkyl or $C_{1-6}$ alkoxy; and ring B is

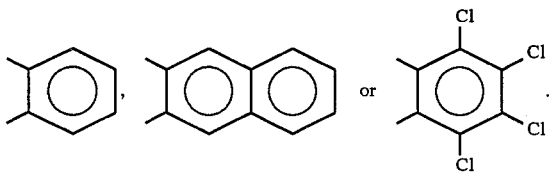

The phthalide compounds of general formula (I) wherein $R_1$ or $R_6$ is an alkoxy group may provide for colored images on reacting with a developer but since the developed colors are gray series colors, they are particularly preferred in terms of shade for use in black image-producing recording materials containing other black-producing color formers.

The phthalide compound (I) of this invention (hereinafter referred to as the compound of the invention) can be synthesized by, inter alia, reacting an ethylene compound of general formula (II) with a benzoic acid derivative of general formula (III) in the presence of a dehydrative condensing agent.

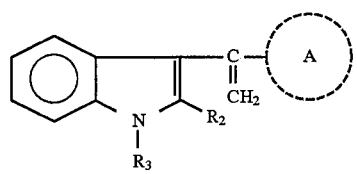

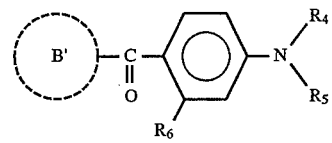

wherein ring A, ring B', and $R_2$–$R_6$ are as defined hereinbefore.

The dehydrative condensing agent that can be used includes acetic anhydride, a mixture of glacial acetic acid and concentrated sulfuric acid, polyphosphoric acid, phosphorus pentoxide, boron trifluoride, zinc chloride and so on. However, in availability from commercial sources, acetic anhydride is particularly suitable. When acetic anhydride is used as said dehydrative condensing agent, it is preferable to use not less than 1 mol of acetic anhydride per mol of the ethylene compound. Needless to say there is no upper limit to the proportion of acetic anhydride that may be used but from economic points of view the use of 1–5 molar equivalents is preferred and when an inert solvent such as toluene is used in combination, 1–2 molar equivalents are sufficient. The reaction temperature is preferably 30°–120° C. and, for still better results, 40°–80° C. If the reaction temperature exceeds 120° C., the amounts of byproducts tend to be increased. On the other hand, the reaction time tends to be protracted when the reaction temperature is below 30° C. There is virtually no restriction on reaction time but the reaction generally goes to completion in several hours.

For undeterred progress of this reaction, it is preferable to use an inert solvent, such as toluene or dichloroethane, in conjunction. When the dehydrative condensing agent is acetic anhydride, toluene is a preferred inert solvent from the standpoint of work-ability.

After completion of the reaction, the reaction mixture is treated with alkali, for example an aqueous solution of sodium hydroxide, and extracted with an organic solvent such as toluene for purification. From workability points of view, it is good practice to carry out the alkali treatment in the presence of an organic solvent.

The organic extract is washed with hot water and the organic layer is concentrated, preferably followed by stirring with methanol under reflux and subsequent cooling, to provide the phthalide compound. The phthalide compound can also be obtained by subjecting said organic extract to a conventional purification procedure, for example column chromatography, and, if necessary, further to the same methanol treatment as above.

The compound of this invention is a useful color former for recording material in that it is either white or of pale color, absorbing little the visible and near infrared regions of the spectrum. However, when reacted with a developer, the compound shows an intense absorption in the near infrared region of 680–750 nm and, yet, absorbs little visible light. Therefore, the near infrared absorber produced by the reaction between this compound and a developer is either colorless or of pale color to the eye and has the characteristic that, in the case of a recording material, the recorded image can hardly be recognized by the eye but can be read with the aid of an OCR using a light source with an emission band of 650–750 nm. Furthermore, when this compound is used in combination with other color formers, desired shades dependent on the concomitant color formers can be obtained.

The phthalide compound of this invention is characterized in that ring A in general formula (I) has any of the substituents mentioned hereinbefore. Recording materials containing known phthalide compounds (for example the aforementioned Compounds A–D) as described in inter alia U.S. Pat. No. 4,119,776, wherein this particular moiety is constituted by p-aminophenyl provide developed images that absorb the visible region as well and show colors in the blue-green series.

Specific examples of the compound of this invention are shown in Table 1.

TABLE 1

Ring A: phenyl ring with $(R_1)_n$ substituent

| | $R_1$ | n | Position of $R_1$ | $R_2$ | $R_3$ | $R_4$ | $R_5$ | $R_6$ | Ring B |
|---|---|---|---|---|---|---|---|---|---|
| Compound 1 | Me | 1 | 4- | Me | Et | Et | Et | H | Bz |
| Compound 2 | Et | 1 | 4- | Me | Et | Et | Et | H | Bz |
| Compound 3 | n-Bu | 1 | 4- | Me | Et | Et | Et | H | Bz |
| Compound 4 | n-Oc | 1 | 4- | Me | Et | Et | Et | H | Bz |
| Compound 5 | Me | 1 | 4- | Me | Et | Et | Et | Me | Bz |
| Compound 6 | H | | | Me | Et | n-Bu | n-Bu | Et | Bz |
| Compound 7 | n-Oc | 1 | 4- | Me | Et | Et | Et | Me | Bz |
| Compound 8 | Me | 1 | 4- | Me | Et | Me | Me | H | Bz |
| Compound 9 | H | | | Me | Et | Me | Me | Me | Bz |
| Compound 10 | n-Bu | 1 | 4- | Me | Et | Me | Me | H | Bz |
| Compound 11 | n-Oc | 1 | 4- | Me | Et | Me | Me | H | Bz |
| Compound 12 | Me | 1 | 4- | Me | Et | Me | Me | Me | Bz |
| Compound 13 | H | | | Me | Et | Me | Me | H | Bz |
| Compound 14 | H | | | Me | Et | n-Bu | n-Bu | H | Bz |
| Compound 15 | n-Bu | 1 | 4- | Me | Et | n-Bu | n-Bu | H | Bz |
| Compound 16 | Me | 1 | 4- | Me | n-Bu | Et | Et | H | Bz |
| Compound 17 | H | | | Me | n-Bu | Et | Et | H | Bz |
| Compound 18 | n-Oc | 1 | 4- | Me | n-Bu | Et | Et | Me | Bz |
| Compound 19 | n-Bu | 1 | 4- | Me | n-Bu | Me | Me | H | Bz |
| Compound 20 | H | | | Me | n-Bu | Me | Me | H | Bz |
| Compound 21 | Me | 1 | 4- | Me | n-Bu | Me | Me | Me | Bz |
| Compound 22 | H | | | Me | n-Bu | Me | Me | Me | Bz |
| Compound 23 | n-Bu | 1 | 4- | Me | n-Bu | n-Bu | n-Bu | H | Bz |
| Compound 24 | H | | | Me | n-Bu | n-Bu | n-Bu | H | Bz |
| Compound 25 | H | | | Me | n-Bu | n-Bu | n-Bu | Me | Bz |
| Compound 26 | Me | 1 | 4- | Me | n-Oc | Et | Et | H | Bz |
| Compound 27 | H | | | Me | n-Oc | Et | Et | Me | Bz |
| Compound 28 | n-Bu | 1 | 4- | Me | n-Oc | Me | Me | H | Bz |
| Compound 29 | H | | | Me | n-Oc | Me | Me | H | Bz |
| Compound 30 | H | | | Me | n-Oc | Me | Me | Me | Bz |
| Compound 31 | n-Oc | 1 | 4- | Me | n-Oc | n-Bu | n-Bu | H | Bz |
| Compound 32 | H | | | Me | n-Oc | n-Bu | n-Bu | Me | Bz |
| Compound 33 | Me | 1 | 4- | Ph | Et | Et | Et | H | Bz |
| Compound 34 | H | | | Ph | Et | Et | Et | H | Bz |
| Compound 35 | n-Bu | 1 | 4- | Ph | Et | Et | Et | H | Bz |
| Compound 36 | n-Oc | 1 | 4- | Ph | Et | Et | Et | H | Bz |
| Compound 37 | Me | 1 | 4- | Ph | Et | Et | Et | Me | Bz |
| Compound 38 | H | | | Ph | Et | Et | Et | Me | Bz |
| Compound 39 | n-Oc | 1 | 4- | Ph | Et | Et | Et | Me | Bz |
| Compound 40 | Me | 1 | 4- | Ph | Et | Me | Me | H | Bz |
| Compound 41 | H | | | Ph | Et | Me | Me | H | Bz |
| Compound 42 | n-Bu | 1 | 4- | Ph | Et | Me | Me | H | Bz |
| Compound 43 | n-Oc | 1 | 4- | Ph | Et | Me | Me | H | Bz |
| Compound 44 | Me | 1 | 4- | Ph | Et | Me | Me | Me | Bz |
| Compound 45 | H | | | Ph | Et | Me | Me | Me | Bz |
| Compound 46 | H | | | Ph | Et | n-Bu | n-Bu | H | Bz |
| Compound 47 | H | | | Ph | n-Bu | Et | Et | H | Bz |
| Compound 48 | n-Oc | 1 | 4- | Ph | n-Bu | Et | Et | Me | Bz |
| Compound 49 | n-Bu | 1 | 4- | Ph | n-Bu | Me | Me | H | Bz |
| Compound 50 | Me | 1 | 4- | Ph | n-Bu | Me | Me | Me | Bz |
| Compound 51 | H | | | Ph | n-Bu | n-Bu | n-Bu | H | Bz |
| Compound 52 | H | | | Ph | n-Bu | n-Bu | n-Bu | Me | Bz |
| Compound 53 | H | | | Ph | Et | Me | Me | n-Bu | Bz |
| Compound 54 | H | | | Ph | n-Oc | Me | Me | H | Bz |
| Compound 55 | H | | | Ph | n-Oc | Me | Me | Me | Bz |
| Compound 56 | H | | | Ph | n-Oc | n-Bu | n-Bu | Me | Bz |
| Compound 57 | H | | | Me | Et | Et | Et | H | Bz |
| Compound 58 | H | | | Et | Et | Et | Et | H | Bz |
| Compound 59 | n-Pr | 1 | 4- | Me | Me | Et | Et | H | Bz |
| Compound 60 | n-Oc | 1 | 4- | Me | Et | n-Pr | n-Pr | H | Bz |
| Compound 61 | Me | 1 | 4- | Et | Et | Et | Et | Et | Bz |

TABLE 1-continued

| Compound | | | | | | | | | |
|---|---|---|---|---|---|---|---|---|---|
| Compound 62 | H | | | Me | Et | Et | Et | n-Bu | Bz |
| Compound 63 | n-Oc | 1 | 4- | Me | Me | Et | Et | Me | Bz |
| Compound 64 | Me | 1 | 4- | Et | n-Pr | Me | Me | H | Bz |
| Compound 65 | H | | | n-Bu | Me | n-Pr | n-Pr | H | Bz |
| Compound 66 | n-Bu | 1 | 4- | p-tol | Et | Me | Me | H | Bz |
| Compound 67 | n-Pr | 1 | 4- | Me | Et | n-He | n-He | H | Bz |
| Compound 68 | Me | 1 | 4- | Me | n-Pr | Me | Me | Me | Bz |
| Compound 69 | H | | | n-Pr | n-He | Me | Me | Me | Bz |
| Compound 70 | H | | | Me | Et | Et | Et | Me | Bz |
| Compound 70 | n-Bu | 1 | 4- | p-tol | Et | n-Bu | n-Bu | H | Bz |
| Compound 72 | Me | 1 | 4- | Ph | Et | Et | Me | H | Bz |
| Compound 73 | H | | | Ph | Et | Et | Me | H | Bz |
| Compound 74 | n-Bu | 1 | 4- | Ph | Et | n-Pr | Et | H | Bz |
| Compound 75 | n-Oc | 1 | 4- | Ph | Et | Et | Et | Et | Bz |
| Compound 76 | Me | 1 | 4- | p-tol | Et | Et | Et | Me | Bz |
| Compound 77 | Et | 1 | 4- | p-ClPh | Me | Et | Et | n-Bu | Bz |
| Compound 78 | n-Pr | 1 | 4- | Ph | Et | Et | Me | Me | Bz |
| Compound 79 | Me | 1 | 4- | p-tol | Et | Me | Me | H | Bz |
| Compound 80 | H | | | Ph | Me | n-He | n-He | H | Bz |
| Compound 81 | n-Bu | 1 | 4- | Et | Et | n-Pr | n-Pr | H | Bz |
| Compound 82 | n-Pr | 1 | 4- | Et | Et | Me | Me | H | Bz |
| Compound 83 | Me | 1 | 4- | Ph | n-He | Me | Me | Me | Bz |
| Compound 84 | H | | | Ph | n-Oc | Et | Et | H | Bz |
| Compound 85 | H | | | Ph | n-Pr | n-Bu | n-Bu | H | Bz |
| Compound 86 | H | | | p-tol | Et | Et | Et | MeO | Bz |
| Compound 87 | Me | 1 | 4- | Me | Et | n-Bu | n-Bu | EtO | Bz |
| Compound 88 | 2-EtHe | 1 | 4- | Et | Me | p-ClPh | Et | n-OcO | Bz |
| Compound 89 | Me | 1 | 4- | Me | Et | Et | Et | n-BuO | Bz |
| Compound 90 | n-Pr | 1 | 4- | i-Pr | n-He | Ph | Ph | Me | Bz |
| Compound 91 | H | | | Me | Et | p-EtOPh | Et | H | Bz |
| Compound 92 | Me | 1 | 2- | Me | Et | Et | Et | H | Bz |
| Compound 93 | i-Bu | 1 | 2- | n-Bu | Et | p-tol | Et | n-BuO | Bz |
| Compound 94 | n-Pe | 1 | 2- | Me | Et | n-Bu | n-Bu | EtO | Bz |
| Compound 95 | n-Pr | 1 | 2- | Ph | Me | n-Pe | n-Pe | Et | Bz |
| Compound 96 | s-Bu | 1 | 3- | m-tol | Et | Ph | Me | MeO | Bz |
| Compound 97 | Me | 1 | 3- | Me | Et | Et | Et | H | Bz |
| Compound 98 | MeO | 1 | 4- | Me | Et | Et | Et | H | Bz |
| Compound 99 | MeO | 1 | 4- | Ph | n-Bu | p-MeOPh | Et | MeO | Bz |
| Compound 100 | EtO | 1 | 4- | Me | n-Oc | Ph | Et | n-OcO | Bz |
| Compound 101 | EtO | 1 | 4- | Me | Et | n-Oc | n-Oc | n-Bu | Bz |
| Compound 102 | n-PrO | 1 | 4- | Et | n-He | i-Pr | n-Bu | n-BuO | Bz |
| Compound 103 | n-BuO | 1 | 4- | Ph | n-Pr | Me | i-Bu | n-Bu | Bz |
| Compound 104 | i-PrO | 1 | 2- | n-Bu | Et | o-tol | Me | H | Bz |
| Compound 105 | i-BuO | 1 | 2- | Me | Et | n-Pr | Me | EtO | Bz |
| Compound 106 | MeO | 1 | 3- | Me | n-Do | m-tol | Et | n-Bu | Bz |
| Compound 107 | EtO | 1 | 3- | Me | Et | Me | Me | n-HeO | Bz |
| Compound 108 | Cl | 1 | 4- | Me | Et | Et | Et | H | Bz |
| Compound 109 | Cl | 1 | 4- | m-ClPh | n-Hp | Me | Me | i-BuO | Bz |
| Compound 110 | Cl | 1 | 4- | n-Pr | n-Pe | Ph | Me | Et | Bz |
| Compound 111 | Cl | 1 | 2- | Me | n-De | n-Bu | n-Bu | EtO | Bz |
| Compound 112 | Cl | 1 | 2- | Ph | Et | Ph | Me | H | Bz |
| Compound 113 | Br | 1 | 4- | n-Bu | Me | Et | Me | n-Bu | Bz |
| Compound 114 | Br | 1 | 4- | Me | Et | p-tol | Et | MeO | Bz |
| Compound 115 | Br | 1 | 2- | n-Bu | 2-EtHe | Et | Me | n-HpO | Bz |
| Compound 116 | F | 1 | 4- | Me | i-Bu | Me | Me | Me | Bz |
| Compound 117 | F | 1 | 4- | Ph | Et | p-ClPh | Et | H | Bz |
| Compound 118 | F | 1 | 2- | Me | Et | Et | Et | n-BuO | Bz |
| Compound 119 | Me | 2 | 2,3- | Et | Me | Et | Et | H | Bz |
| Compound 120 | Me | 2 | 2,4- | Ph | Me | Me | Me | EtO | Bz |
| Compound 121 | Me | 2 | 2,4- | Me | Et | Et | Et | H | Bz |
| Compound 122 | Me | 2 | 2,5- | Ph | Me | Me | Me | n-Bu | Bz |
| Compound 123 | Me | 3 | 2,4,6- | Me | Et | p-tol | Et | n-OcO | Bz |
| Compound 124 | Me | 3 | 2,3,4- | Me | Et | Et | Et | MeO | Bz |
| Compound 125 | Me | 2 | 3,5- | n-Pr | Et | Me | Ph | Et | Bz |
| Compound 126 | Et | 2 | 2,4- | Me | Et | Me | Me | H | Bz |
| Compound 127 | Et | 2 | 2,5- | Et | Me | p-MeOPh | Me | Me | Bz |
| Compound 128 | MeO | 3 | 2,4,6- | Me | Et | Et | Et | n-PeO | Bz |
| Compound 129 | MeO | 2 | 2,5- | p-tol | Et | Me | Me | H | Bz |
| Compound 130 | MeO | 2 | 3,4- | Me | Et | Ph | Ph | n-BuO | Bz |
| Compound 131 | MeO | 2 | 3,5- | n-Bu | Et | Et | s-Bu | Et | Bz |
| Compound 132 | EtO | 2 | 2,4- | Ph | Me | n-Bu | n-Bu | n-Heo | Bz |
| Compound 133 | Cl | 2 | 2,4- | Me | Et | Et | Et | H | Bz |
| Compound 134 | Cl | 3 | 2,4,6- | Me | Me | p-ClPh | Et | EtO | Bz |
| Compound 135 | Cl | 2 | 2,5- | Me | Et | Ph | Ph | H | Bz |
| Compound 136 | Cl | 3 | 2,3,4- | n-Bu | Et | Et | Et | Me | Bz |
| Compound 137 | Cl | 2 | 3,5- | Ph | Me | Et | Et | i-PrO | Bz |
| Compound 138 | Br | 2 | 2,4- | n-Bu | Me | n-Bu | n-Bu | H | Bz |
| Compound 139 | Br | 3 | 2,3,4- | p-tol | n-Pr | Me | Me | Me | Bz |
| Compound 140 | Br | 2 | 2,5- | Me | Et | Et | Et | MeO | Bz |

TABLE 1-continued

| | | | | | | | | | |
|---|---|---|---|---|---|---|---|---|---|
| Compound 141 | F | 2 | 2,4- | n-Bu | Et | p-EtOPh | Et | H | Bz |
| Compound 142 | F | 2 | 2,5- | Ph | Et | Et | Et | MeO | Bz |
| Compound 143 | H | | | Ph | Et | Me | Me | n-Bu | Np |
| Compound 144 | Me | 1 | 4- | Me | Et | Et | Et | H | Np |
| Compound 145 | n-Pr | 1 | 4- | Me | Et | n-Bu | Et | EtO | Np |
| Compound 146 | MeO | 1 | 4- | Me | Et | n-Bu | n-Bu | MeO | Np |
| Compound 147 | n-BuO | 1 | 4- | n-Bu | Me | Me | Me | H | Np |
| Compound 148 | Et | 1 | 2- | Ph | Et | Et | Et | H | Np |
| Compound 149 | Cl | 1 | 4- | Me | Et | n-Bu | Et | EtO | Np |
| Compound 150 | Me | 2 | 2,4- | Me | Et | Ph | Et | Me | Np |
| Compound 151 | MeO | 2 | 3,4- | Ph | n-Bu | Me | Me | H | Np |
| Compound 152 | Cl | 3 | 2,3,4- | p-tol | Et | Ph | Et | n-PrO | Np |
| Compound 153 | H | | | Me | Et | Me | Me | Me | TcBz |
| Compound 154 | H | | | Ph | Et | Me | Me | MeO | TcBz |
| Compound 155 | Me | 1 | 4- | Me | Et | Et | Et | H | TcBz |
| Compound 156 | Me | 1 | 2- | Me | Et | Et | Et | H | TcBz |
| Compound 157 | n-Bu | 1 | 3- | Et | Et | p-ClPh | Et | Et | TcBz |
| Compound 158 | MeO | 1 | 4- | Me | n-Bu | n-Pr | Me | H | TcBz |
| Compound 159 | EtO | 1 | 4- | Ph | n-Bu | Ph | Me | n-PrO | TcBz |
| Compound 160 | Cl | 1 | 4- | Me | Et | Me | Me | MeO | TcBz |
| Compound 161 | Br | 1 | 4- | p-tol | Et | Me | Me | H | TcBz |
| Compound 162 | Me | 3 | 2,4,6- | Me | Et | Me | Me | n-BuO | TcBz |
| Compound 163 | MeO | 2 | 3,4- | Me | Me | Et | Et | Me | TcBz |
| Compound 164 | Cl | 2 | 2,4- | Me | Me | Ph | Ph | H | TcBz |

Ring A: 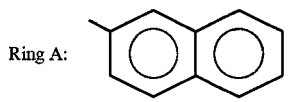

| | $R_2$ | $R_3$ | $R_4$ | $R_5$ | $R_6$ | Ring B |
|---|---|---|---|---|---|---|
| Compound 165 | Me | Et | Et | Et | H | Bz |
| Compound 166 | Ph | Et | Me | Me | Me | Bz |
| Compound 167 | Et | Me | Ph | Et | Eto | Bz |
| Compound 168 | Me | Et | n-Pr | Et | n-BuO | Bz |
| Compound 169 | p-tol | n-Bu | n-Bu | Et | n-PeO | Bz |
| Compound 170 | n-Bu | n-He | Ph | Ph | n-Bu | Bz |
| Compound 171 | p-tol | Et | Ph | Ph | MeO | Np |
| Compound 172 | Me | n-Bu | Me | Me | Et | Np |
| Compound 173 | Me | Me | Et | Et | n-BuO | N |
| Compound 174 | Ph | Et | Ph | Et | H | Np |
| Compound 175 | Me | Et | Et | Et | H | TcBz |
| Compound 176 | Me | Et | n-Bu | Et | EtO | TcBz |
| Compound 177 | Me | n-Bu | Ph | Et | Me | TcBz |
| Compound 178 | Ph | Et | Ph | Ph | i-PrO | TcBz |

Ring A: 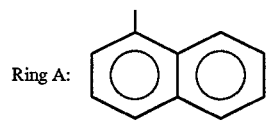

| | $R_2$ | $R_3$ | $R_4$ | $R_5$ | $R_6$ | Ring B |
|---|---|---|---|---|---|---|
| Compound 179 | Me | Et | Et | Et | H | Bz |
| Compound 180 | Ph | Et | n-Bu | Me | MeO | Bz |
| Compound 181 | Et | Me | Et | Et | Et | Bz |
| Compound 182 | Me | Et | Ph | Et | EtO | Bz |
| Compound 183 | p-tol | n-Bu | Ph | Ph | H | Bz |
| Compound 184 | Me | Et | n-Pr | Et | Me | Np |
| Compound 185 | Me | Et | Et | Et | MeO | Np |
| Compound 186 | Ph | Et | Ph | Et | Me | Np |
| Compound 187 | n-Bu | n-Bu | Ph | Ph | H | Np |
| Compound 188 | n-Bu | Et | n-Bu | Et | n-BuO | TcBz |
| Compound 189 | Ph | n-Pr | Me | Me | H | TcBz |
| Compound 190 | Me | Et | Ph | Ph | n-OcO | TcBz |
| Compound 191 | Me | Et | Ph | Et | Me | TcBz |

In the table, H stands for hydrogen; Me for methyl, Et for ethyl, n-Pr for n-propyl, i-Pr for isopropyl, n-Bu for n-butyl, i-Bu for isobutyl, s-Bu for sec-butyl, n-Pe for n-pentyl, n-He for n-hexyl, n-Hp for n-heptyl, n-Oc for n-octyl, 2-EtHe for 2-ethylhexyl, n-De for n-decyl, n-Do for n-dodecyl, Ph for phenyl, p-tol for p-tolyl, o-tol for o-tolyl, m-tol for m-tolyl, p-ClPh for p-chlorophenyl, m-C₁Ph for m-chlorophenyl, p-MeOPh for p-methoxyphenyl, p-EtOPh for p-ethoxyphenyl, MeO for methoxy, EtO for ethoxy, n-PrO for n-propoxyl, i-PrO for isopropoxy, n-BuO for n-butoxy, i-BuO for isobutoxy, n-PeO for n-pentyloxy, n-HeO for n-hexyloxyl, n-HpO for n-heptyloxy, n-OcO for n-octyloxy, Cl for chlorine, Br for bromine, F for fluorine

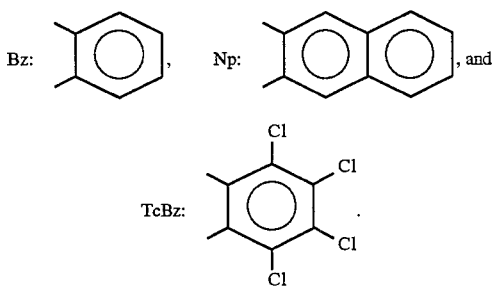

It is considered that the near infrared absorber of this invention is an electron transfer reaction product between the color former and a developer and, on account of this reaction, absorbs the near infrared region. Generally, it can be produced by dissolving the color former and developer in a solvent and distilling off the solvent. In its application, the above solution may be coated on a support, e.g. a sheet of wood-free paper or synthetic paper or a plastic film, and dried to provide the desired near infrared absorber on the support. In some cases, the absorber can be manufactured by melting the color former and developer under heating and cooling the melt.

The developer that can be used in the near infrared absorber includes, among others, phenol derivatives, acidic polymers, metal modification products thereof, organic carboxylic acids and metal salts thereof.

The following are some examples of developers.

Phenol derivatives: 4-tert-butylphenol, 4-octylphenol, 4-phenylphenol, 1-naphthol, 2-naphthol, hydroquinone, resorcinol, 4-tert-octylcatechol, 2,2'-dihydroxybiphenyl, 4,4'-dihydroxydiphenyl ether, 2,2-bis(4-hydroxyphenyl) propane [generic name: bisphenol A], tetrabromobisphenol A, 1,1-bis(4-hydroxyphenyl)cyclohexane, 2,2-bis(4-hydroxy-3-methylphenyl)propane, 2,2-bis(4-hydroxyphenyl)-4-methylpentane, 1,4-bis(4-hydroxycumyl) benzene, 1,3,5-tris(4-hydroxycumyl)benzene, 4,4'-(m-phenylenediisopropylidene)bisphenol, 4,4'-(p-phenylenediisopropylidene)bisphenol, ethyl bis(4-hydroxyphenyl)acetate, n-butyl 4,4-bis(4-hydroxyphenyl) valerate, benzyl 4-hydroxybenzoate, phenethyl 4-hydroxybenzoate, 2-phenoxyethyl 2,4-dihydroxybenzoate, dimethyl 4-hydroxyphthalate, n-propyl gallate, n-octyl gallate, n-dodecyl gallate, n-octadecyl gallate, hydroquinone monobenzyl ether, bis(3-methyl-4-hydroxyphenyl)sulfide, bis(2-methyl-4-hydroxyphenyl) suflide, bis(3-phenyl-4-hydroxyphenyl)suflide, bis(3-cyclohexyl-4-hydroxyphenyl)sulfide, bis(4-hydroxyphenyl) sulfoxide, bis(4-hydroxyphenyl)sulfone [generaic name bisphenol S], tetrabromobisphenol S, bis(3-allyl-4-hydroxyphenyl)suflone, 2,4'-dihydroxydiphenyl sulfone, 4-hydroxy-4'-methyldiphenyl sulfone, 4-hydroxy-4'-chlorodiphenyl sulfone, 4-hydroxy-4'-n-propoxydiphenyl sulfone, 4-hydroxy-4'-isopropoxydiphenyl sulfone, 4-hydroxy-4'-n-butoxydiphenyl sulfone, 3,4-dihydroxy-4'-methyldiphenyl sulfone, 2,4-dihydroxydiphenyl sulfone, 2-methoxy-4'-hydroxydiphenyl sulfone, 2-ethoxy-4'-hydroxydiphenyl sulfone, bis(2-hydroxy-5-tert-butylphenyl)sulfone, bis(2-hydroxy-5-chlorophenyl) sulfone, 4-hydroxybenzophenone, 2,4-dihydroxybenzophenone, 1,7-bis(4-hydroxyphenylthio)-3,5-dioxaheptane, 1,5-bis(4-hydroxyphenylthio)-3-oxapentane and so on.

The acidic polymer or its metal modification product includes phenol resin, alkylphenol resin, maleic acid resin, phenol-acetylene resin, phenol-formaldehyde resin, products of condensation of carboxylic acids containing at least one hydroxyl group with formaldehyde, and modification products thereof with polyvalent metals such as zinc, nickel, etc., among others.

The organic carboxylic acid or its metal salt includes various organic acids such as salicylic acid, 3-isopropylsalicylic acid, 3-tert-butylsalicylic acid, 3-benzylsalicylic acid, 3-chloro-5-(α-methylbenzyl) salicylic acid, 3-phenyl-5-(α,α-dimethylbenzyl)salicylic acid, 3,5-di-(α-methylbenzyl)salicylic acid, 4-(3-p-toluenesulfonylpropyloxy)salicylic acid, 5-{p-[2-(p-methoxyphenoxy)ethoxy]cumyl}salicylic acid, 3-cyclohexylsalicylic acid, 3,5-di-tert-butylsalicylic acid, 3-methyl-5-α-methylbenzylsalicylic acid, 4-[2-(4-methoxyphenoxy)ethoxy]salicylic acid, 2-hydroxy-3-naphthoic acid, 2-hydroxy-6-naphthoic acid, monobenzyl phthalate, monophenyl phthalate, 4-nitrobenzoic acid, 3-nitrobenzoic acid, 2-nitrobenzoic acid and 4-chlorobenzoic acid or their salts with various metals (e.g. nickel, zinc, aluminum, calcium, etc.) and complexes such as zinc thiocyanate antipyrine complex, molybdic acid acetylacetone complex, etc., among others.

Aside from the above compounds, the known developers for color-forming recording materials, e.g. urea derivatives such as phenylthiourea, and inorganic developers such as clay can also be employed as well.

Among the particularly preferred developers, the preferred phenol derivative includes bisphenol A, bisphenol S, benzyl p-hydroxybenzoate, 2,2-bis(p-hydroxyphenyl)-4-methylpentane, 3,3'-diallyl-4,4'-dihydroxydiphenyl sulfone, 1,1-bis(p-hydroxyphenyl)cyclohexane, 1,5-bis(p-hydroxyphenylmercapto)-3-oxapentane, 4-hydroxy-4'-isopropoxydiphenyl sulfone, 3,4-dihydroxy-4'-methyldiphenyl sulfone, 1,7-bis(4-hydroxyphenylthio)-3,5-dioxaheptane, tetrabromobisphenol A and tetrabromobisphenol S, among others.

The preferred acidic polymer or its metal modification product includes zinc-modified p-octylphenolformaldehyde resin, p-phenylphenol resin and p-alkyl-phenol-formaldehyde resin (e.g. known under the tradenames of Tamanol and Hitanol), among others.

The preferred organic carboxylic acid or its metal salt includes salicylic acid derivative zinc salts such as zinc 4-[2-(4-methoxyphenoxy)ethoxy]salicylate, among others.

The ratio of the compound of this invention to the developer varies with different species of the compound but may generally be about 10:90–75:25 and preferably about 20:80–50:50.

The near infrared absorber of this invention can be put to use as it is or in the form of a near infrared absorbing composition containing a binder and other additives, for example by such techniques as coating, compounding, or hard-coating on or with such matrices as paper, plastic sheet, plastic film, glass, clear resin, etc. or polymerizing with monomers, in such applications as near infrared absorbing filters, optical recording media, protective goggles, agricultural film, heat rays absorbing glass, filters for light-receiving devices and so forth.

The phthalide compound of this invention can be used in secret ink, in which application the characters or codes written or printed are not visible to the eye but can be read with the OCR or equivalent. As for secret ink, an oil-based secret ink can be produced by, for example, dissolving the phthalide compound of this invention and a developer in an oily vehicle, if necessary followed by adding an oil-soluble binder resin or the like. A water-based ink for secret pen writing can be produced by, for example, dispersing the near infrared absorber containing both the compound of this invention and a developer in a water-soluble organic solvent such as alcohol and, then, adding water, if necessary together with a water-soluble binder resin or the like.

In the production of said oil-based secret ink, the vehicle can be an ordinary organic solvent such as aromatic hydrocarbons, e.g. toluene and xylene, methyl ethyl ketone and so on. However, in the production of writing utensils (felt pen, ball-point pen, etc.), it is advantages, from the standpoint of health protection and safety, to employ an aliphatic or alicyclic hydrocarbon solvent boiling at 75°–180° C. The alicyclic hydrocarbon solvent mentioned just above includes dimethylcyclohexane, ethylcyclohexane, propylcyclohexane, butylcyclohexane, cyclohexene, etc., and the aliphatic hydrocarbon solvent includes saturated aliphatic hydrocarbons such as n-hexane, n-octane, isooctane, etc. and petroleum-based mixture solvents such as ligroin, mineral spirit, purified rubber oil, and so on.

For the production of a water-based ink, an alcohol or an aqueous solution of a low-volatile or non-volatile hydrophilic organic solvent can be used with advantage as a dispersant. The alcohol mentioned above preferably includes lower alcohols such as methanol, ethanol, isopropyl alcohol, etc., while the preferred aqueous solution of low-volatile or non-volatile hydrophilic organic solvent includes aqueous solutions prepared by dissolving 5–200 parts of ethylene glycol, diethylene glycol, triethylene glycol, propylene glycol, dipropylene glycol, glycerol, diglycerol, methylcarbitol, ethylcarbitol, butylcarbitol, ethylcellosolve, butylcellosolve or the like in each 100 parts of water.

If necessary, a variety of water-soluble resins (for a water-based secret ink) and solvent-soluble resins (for an oil-based secret ink) can be used as the dispersant, binder and/or thickener.

Among the solvent-soluble resins mentioned above can be reckoned hydrogenated rosin and rosin ester resin, alkylphenol resin, polyolefin resin, rosin-modified alkyd resin, ketone resin and so on.

Among the water-soluble resins can be reckoned melamine-formaldehyde polymer, water-soluble acrylic resin, ligninsulfonic acid, etc., while the water-dispersible resin may for example be polyvinyl butyral, styrene-butadiene copolymer or the like.

The preferred formulation per 100 parts of ink is 5–20 parts of the compound of this invention, 10–30 parts of developer, 5–20 parts of resin and 40–80 parts of solvent.

In a recording material utilizing the reaction between a color former and a developer, the compound of this invention can be used singly in the recording material or, if necessary, can be used in combination with one or more different coloring materials (color former). Particularly, a black colored image can be obtained by using one or more species of the compound of this invention in combination with one or more species of the fluorane compound of general formula (IV)

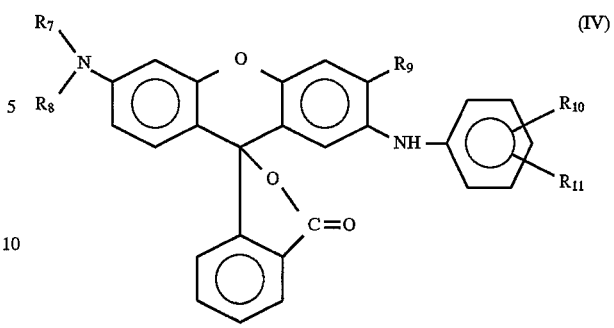

wherein $R_7$ and $R_8$ independently represent alkyl, alkoxyalkyl, cycloalkyl, aryl or tetrahydrofuryl; $R_9$ represents hydrogen, methyl or chlorine; $R_{10}$ and $R_{11}$ independently represent hydrogen, alkyl, chlorine or fluorine; $R_7$ and $R_8$ may, taken together with the adjacent nitrogen atom, form a heterocyclic group.

The following is a partial listing of species of the fluorane compound of general formula (IV) which can be used in this invention.

2-Anilino-3-methyl-6-dimethylaminofluorane, 2-anilino-3-methyl-6-diethylaminofluorane, 2-anilino-3-methyl-6-di-n-propylaminofluorane, 2-anilino-3-methyl-6-di-n-butylaminofluorane, 2-anilino-3-methyl-6-di-n-pentylaminofluorane, 2-anilino-3-methyl-6-(N-methyl-N-ethylamino)fluorane, 2-anilino-3-methyl-6-(N-methyl-N-n-propylamino)fluorane, 2-anilino-3-methyl-6-(N-methyl-N-n-butylamino)fluorane, 2-anilino-3-methyl-6-(N-methyl-N-isobutylamino)fluorane, 2-anilino-3-methyl-6-(N-methyl-N-n-pentylamino)fluorane, 2-anilino-3-methyl-6-(N-methyl-N-cyclohexylamino)fluorane, 2-anilino-3-methyl-6-(N-ethyl-N-n-propylamino)fluorane, 2-anilino-3-methyl-6-(N-ethyl-N-n-butylamino)fluorane, 2-anilino-3-methyl-6-(N-ethyl-N-isobutylamino)fluorane, 2-anilino-3-methyl-6-(N-ethyl-N-n-pentylamino)fluorane, 2-anilino-3-methyl-6-(N-ethyl-N-isopentylamino)fluorane, 2-anilino-3-methyl-6-(N-ethyl-N-n-octylamino)fluorane, 2-anilino-3-methyl-6-[N-ethyl-N-(3-ethoxypropyl)amino]fluorane, 2-anilino-3-methyl-6-(N-ethyl-N-p-tolylamino)fluorane, 2-anilino-3-methyl-6-(N-ethyl-N-tetrahydrofrufurylamino)fluorane, 2-anilino-3-chloro-6-diethylaminofluorane, 2-(2-chloroanilino)-6-diethylaminofluorane, 2-(2-chloroanilino)-6-di-n-butylaminofluorane, 2-(2-fluoroanilino)-6-diethylaminofluorane, 2-(3-trifluoromethylanilino)-6-diethylaminofluorane, 2-(3-methylanilino)-3-methyl-6-diethylaminofluorane, 2-(4-methylanilino)-3-methyl-6-diethylaminofluorane, 2-(4-tertpentylanilino)-3-methyl-6-diethylaminofluorane, 2-(3-chloro-4-methylanilino)-3-methyl-6-diethylaminofluorane, 2-(2,4-dimethylanilino)-3-methyl-6-diethylaminofluorane, 2-(2,6-dimethylanilino)-3-methyl-6-diethylaminofluorane, 2-(2,6-diethylanilino)-3-methyl-6-diethylaminofluorane, 2-(2,4-dimethylanilino)-3-methyl-6-di-n-butylaminofluorane, 2-(2,6-dimethylanilino)-3-methyl-6-di-n-butylaminofluorane and 2-(2,6-diethylanilino)-3-methyl-6-di-n-butylaminofluorane, among others.

In addition with the combined use of the compound of this invention and the fluorane compound of general formula (IV), other color formers that are conventionally used in recording materials of this type can be selectively used as required for the purpose of adjusting the developed color or absorption characteristics.

The diaryl phthalide compound, among said other color formers, includes 3,3-bis(4-dimethylaminophenyl)-6-dimethylaminophthalide (generic name CVL), 3,3-bis(4- dimethylaminophenyl)phthalide, 3-(4-dimethylaminophenyl)-3-(4-diethylamino-2-methylphenyl)-6dimethylaminophthalide, 3,3-bis(9-ethylcarbazol-3-yl)-6-dimetylaminophthalide and 3-(4-dimethylaminophenyl)-3-(1-methylpyrrol-3-yl)-6-dimethylaminophthalide, among others.

The indolyl phthalide compound, among said other color formers, includes 3-(4-dimethylaminophenyl)-3-(1,2-dimethylindol-3-yl)phthalide, 3,3-bis(1,2-dimethylindol-3-yl)-6-dimethylaminophthalide, 3,3-bis(1-ethyl-2-methylindol-3-yl)phthalide, 3,3-bis(1-n-butyl-2-methylindol-3-yl)phthalide, 3,3-bis(1-n-octyl-2-methylindol-3-yl)phthalide, 3-(2-ethoxy-4-diethylaminophenyl)-3-(1-ethyl-2-methylindol-3-yl)phthalide, 3-(2-ethoxy-4-dibutylaminophenyl)-3-(1-ethyl-2-methylindol-3-yl)phthalide and 3-(2-ethoxy-4-diethylaminophenyl)-3-(1-octyl-2-methylindol-3-yl)phthalide, among others.

The vinyl phthalide compound includes 3-(4-diethylaminophenyl)-3-[2,2-bis(1-ethyl-2-methylindol-3-yl)ethenyl]phthalide, 3,3-bis[2-(4-dimethylaminophenyl)-2-(4-methoxyphenyl)ethenyl]-4,5,6,7-tetrachlorophthalide, 3,3-bis[2-(4-pyrrolidinophenyl)-2-(4-methoxyphenyl)ethenyl]-4,5,6,7-tetrachlorophthalide, 3,3-bis[2,2-bis(4-dimethylaminophenyl)ethenyl]-4,5,6,7-tetrachlorophthalide and 3,3-bis[2,2-bis(4-pyrrolidinophenyl)ethenyl]-4,5,6,7-tetrabromophthalide, among others.

The azaphthalide compound includes 3,3-bis(4-diethylamino-2-ethoxyphenyl)-4-azaphthalide, 3-(4-diethylamino-2-ethoxyphenyl)-3-[4-(N-ethyl-N-phenylamino)-2-ethoxyphenyl]-4-azaphthalide, 3-(4-diethylamino-2-ethoxyphenyl)-3-(1-ethyl-2-methylindol-3-yl)-4-azaphthalide and 3-(4-diethylamino-2-ethoxyphenyl)-3-(1-n-octyl-2-methylindol-3-yl)-4-azaphthalide, among others.

The diarylmethane compound includes 4,4'-bis(dimethylamino)benzhydryl benzyl ether and N-halophenylleucauramine, among others.

The rhodamine lactam compound includes rhodamine B anilinolactam, rhodamine B (4-nitroanilino)lactam and rhodamine B (4-chloroanilino)lactam, among others.

The thiazine compound includes benzoyl leucomethylene blue and p-nitrobenzoyl leucomethylene blue, among others.

The spiropyran compound includes 3-methylspirodinaphthopyran, 3-ethylspirodinaphthopyran, 3-phenylspirodinaphthopyran, 3-benzylspirodinaphthopyran and 3-propylspirodibenzopyran, among others.

The fluorene compound includes 3,6-bis(dimethylamino)fluorenespiro[9,3']-6'-dimethylaminophthalide, 3-diethylamino-6-(N-allyl-N-methylamino)fluorenespiro[9,3']-6'-dimethylaminophthalide, 3,6-bis(dimethylamino)-spiro[fluorene-9,6'-6'H-chromeno(4,3-b)indole], 3,6-bis(dimethylamino)-3'-methylspiro[fluorene-9,6'-6'H-chromeno(4,3-b)indole], 3,6-bis(diethylamino)-3'-methyl-spiro[fluorene-9,6'-6'-H-chromeno(4,3-b)indole], among others.

These color formers can be used singly or in combination.

When the compound of this invention is used in combination with a fluorane compound of general formula (IV) or further with other color formers, the compound of this invention preferably accounts for at least 10% of the total weight of all color formers present. If its proportion is less than 10% by weight, there may be cases in which the recorded image can hardly be read with the OCR.

Pressure-sensitive recording materials utilizing the phthalide compound of this invention can be produced by the various known methods disclosed in inter alia Japanese Tokkyo Koho S-42-20144. A general procedure comprises microencapsulating a solution of the color former in an inner-phase solvent by a known microencapsulation technique, e.g. coacervation, interfacial polymerization, in situ polymerization, etc., using a macromolecular compound as a wall-forming material and coating the encapsulated color former on the reverse side of a support such as a sheet of wood-free paper or synthetic paper or a plastic film to provide a CB sheet. On the other hand, a developer is coated on the obverse side of another support to provide a CF sheet. When the CB sheet and CF sheet are superimposed with the coated sides in contact and a pressure is applied to the assembly, the microcapsules in the compressed area are ruptured, whereupon the color former contained in the capsules reacts with the developer to form an image on the obverse side of the CF sheet. Moreover, when a plurality of CFB sheets carrying the developer on the obverse sides and the encapsulated color former on the reverse sides of the respective supports are interposed between said CB sheet and CF sheet, a plurality of image records can be obtained. The invention can also be applied to a recording material of the self-contained type carrying both the developer and encapsulated color former on the same side of its support or to a recording material such that either the developer or the microencapsulated color former occurs within a support, with the other being present in a coating layer.

The developer which can be used in the pressure-sensitive recording material includes inorganic developers such as acid clay, activated clay, attapulgite, zeolite, bentonite, kaolin, etc. and organic developers such as phenolic compounds, novolac phenolic resin or its salts with polyvalent metals, aromatic carboxylic acid derivatives or their salts with polyvalent metals, salicylic acid derivatives or their salts with polyvalent metals, salicylic acid resin or its salts with polyvalent metals, terpene phenol resin or its salts with polyvalent metals, and so on. Particularly preferred are salicylic acid derivative zinc salts and p-octylphenol resin zinc salt.

Thermo-sensitive recording materials utilizing the phthalide compound of this invention can be manufactured by the various known methods disclosed in inter alia Japanese Tokkyo Koho S-45-14039. A general procedure comprises dispersing the color former, developer and sensitizer respectively together with an aqueous solution of a water-soluble polymer such as poly(vinyl alcohol) by means of an attriter, sandmill or the like equipment until a particle diameter not greater than several microns is attained. The sensitizer may be dispersed together with either the color former or the developer or both. The resulting respective dispersions are blended and supplemented, if necessary, with a pigment, binder, wax, metal soap, antioxidant, ultraviolet absorber, etc. to provide a thermo-sensitive coating composition. This thermo-sensitive coating composition is coated on a support such as a sheet of wood-free paper or synthetic paper or a plastic film and smoothened by calendering to provide a thermo-sensitive recording sheet. For improved color developability, the thermo-sensitive coating composition may be coated on a support having a precoated layer containing an adiabatic material such as a plastic pigment or silica. Where necessary, using an aqueous solution of a water-soluble polymer a top coat may be provided on the thermo-sensitive recording layer for imparting water resistance and chemical resistance.

The developer which can be used in the thermo-sensitive recording material may for example be a phenol derivative, an organic acid or its metal salt or complex, or a urea derivative.

Some examples of the respective types of developers are listed below.

The phenol derivative includes 4-tert-butylphenol, 4-octylphenol, 4-phenylphenol, 1-naphthol, 2-naphthol, hydroquinone, resorcinol, 4-tert-octylcatechol, 2,2'-dihydroxybiphenyl, 4,4'-dihydroxydiphenyl ether, 2,2-bis(4-hydroxyphenyl)propane [generic name: bisphenol A], tetrabromobisphenol A, 1,1-bis(4-hydroxyphenyl)cyclohexane, 2,2-bis(4-hydroxy-3-methylphenyl)propane, 2,2-bis(4-hydroxyphenyl)-4-methylpentane, 1,4-bis(4-hydroxycumyl) benzene, 1,3,5-tris(4-hydroxycumyl)benzene, 4,4'-(m-phenylenediisopropylidene)bisphenol, 4,4'-(p-phenylenediisopropylidene)bisphenol, ethyl bis(4-hydroxyphenyl)acetate, n-butyl 4,4-bis(4-hydroxyphenyl) valerate, benzyl 4-hydroxybenzoate, phenethyl 4-hydroxybenzoate, 2-phenoxyethyl 2,4-dihydroxybenzoate, dimethyl 4-hydroxyphthalate, n-propyl gallate, n-octyl gallate, n-dodecyl gallate, n-octadecyl gallate, hydroquinone monobenzyl ether, bis(3-methyl-4-hydroxyphenyl)sulfide, bis(2-methyl-4-hydroxyphenyl) sulfide, bis(3-phenyl-4-hydroxyphenyl)sulfide, bis(3-cyclohexyl-4-hydroxyphenyl)sulfide, bis(4-hydroxyphenyl) sulfoxide, bis(4-hydroxyphenyl)sulfone [generic name bisphenol S], tetrabromobisphenol S, bis(3-allyl-4-hydroxyphenyl)sulfone, 2,4'-dihydroxydiphenyl sulfone, 4-hydroxy-4'-methyldiphenyl sulfone, 4-hydroxy-4'-chlorodiphenyl sulfone, 4-hydroxy-4'-n-propoxydiphenyl sulfone, 4-hydroxy-4'-isopropoxydiphenyl sulfone, 4-hydroxy-4'-n-butoxydiphenyl sulfone, 3,4-dihydroxy-4'-methyldiphenyl sulfone, 2,4-dihydroxydiphenyl sulfone, 2-methoxy-4'-hydroxydiphenyl sulfone, 2-ethoxy-4'-hydroxydiphenyl sulfone, bis(2-hydroxy-5-tert-butylphenyl)sulfone, bis(2-hydroxy-5-chlorophenyl) sulfone, 4-hydroxybenzophenone, 2,4-dihydroxybenzophenone, 1,7-bis(4-hydroxyphenylthio)-3,5-dioxaheptane and 1,5-bis(4-hydroxyphenylthio)-3-oxapentane, among others.

The organic carboxylic acid or its metal salt includes various organic acids such as salicylic acid, 3-isopropylsalicylic acid, 3-tert-butylsalicylic acid, 3-benzylsalicylic acid, 3-chloro-5-(α-methylbenzyl) salicylic acid, 3-phenyl-5-(α,α-dimethylbenzyl)salicylic acid, 3,5-bis(α-methylbenzyl)salicylic acid, 4-(3-p-toluenesulfonylpropyloxy)salicylic acid, 5-{p-[2-(p-methoxyphenoxy)ethoxy]cumyl}salicylic acid, 3-cyclohexylsalicylic acid, 3,5-di-tert-butylsalicylic acid, 3-methyl-5-α-methylbenzylsalicylic acid, 4-[2-(4-methoxyphenoxy)ethoxy]salicylic acid, 2-hydroxy-3-naphthoic acid, 2-hydroxy-6-naphthoic acid, monobenzyl phthalate, monophenyl phthalate, 4-nitrobenzoic acid, 3-nitrobenzoic acid, 2-nitrobenzoic acid and 4-chlorobenzoic acid or their salts with various metals (e.g. nickel, zinc, aluminum, calcium, etc.) and complexes such as zinc thiocyanate antipyrine complex and molybdic acid acetylacetone complex, among others.

The urea derivative includes phenylthiourea, N,N'-bis(3-trifluoromethylphenyl)thiourea and 1,4-bis(3-chlorophenyl) thiosemicarbazide, among others. These compounds can be used alone or in combination.

The sensitizer which can be used includes a variety of heat-meltable substances. The following is a partial listing of such substances.

The acid amide compound that can be used as said sensitizer includes caproic acid amide, capric acid amide, stearic acid amide, palmitic acid amide, oleic acid amide, stearyl urate and stearyl anilide, among others.

The fatty acid or its metal salt includes stearic acid, behenic acid, palmitic acid, etc. and their salts with zinc, aluminum, calcium, etc., among others.

The ester compound includes benzyl 4-benzyloxybenzoate, phenyl 2-naphthoate, phenyl 1-hydroxy-2-naphthoate, dibenzyl oxalate, di(4-methylbenzyl)oxalate, di(4-chlorobenzyl)oxalate, diphenacyl glutarate, di(4-methylphenyl)carbonate and dibenzyl terephthalate, among others.

The hydrocarbon compound includes 4-benzylbiphenyl, m-terphenyl, fluorene, fluoranthene, 2,6-diisopropylnaphthalene and 3-benzylacenaphthene, among others.

The ether compound includes 2-benzyloxynaphthalene, 2-(4-methylbenzyloxy)naphthalene, 1,4-diethoxynaphthalene, 1,4-dibenzyloxynaphthalene, 1,2-diphenoxyethane, 1,2-bis(3-methylphenoxy)ethane, 1-phenoxy-2-(4-ethylphenoxy)ethane, 1-(4-methoxyphenoxy)-2-phenoxyethane, 1-(4-methoxyphenoxy)-2-(3-methylphenoxy)ethane, 1-(4-methoxyphenoxy)-2-(2-methylphenoxy)ethane, 4-(4-methylphenoxy)biphenyl, 1,4-bis(2-chlorobenzyloxy) benzene, 4,4'-di-n-butoxydiphenyl sulfone, 1,2-diphenoxybenzene, 1,4-bis(2-chlorophenoxy)benzene, 1,4-bis(4-methylphenoxy)benzene, 1,4-bis(3-methylphenoxymethyl)benzene, 1-(4-chlorobenzyloxy)-4-ethoxybenzene, 4,4'-diphenoxydiphenyl ether, 1,4-bis(4-benzylphenoxy)benzene and 1,4-bis[(4-methylphenoxy) methoxymethyl]benzene, among others. These substances can be used singly or in combination.

Particularly preferred are 4-benzylbiphenyl, m-terphenyl, 2-benzyloxynaphthalene, di(4-methylbenzyl)oxalate and 1,2-bis(3-methylphenoxy)ethane.

As the pigment, various organic and inorganic pigments can be used. Preferred species are calcium carbonate, barium sulfate, titanium dioxide, aluminum hydroxide, amorphous silica, urea-formaldehyde resin powder, polyethylene powder and so on.

The binder may be a water-soluble polymer or a water-insoluble polymer. Preferred examples of the water-soluble polymer are methylcellulose, carboxymethylcellulose, hydroxyethylcellulose, starch and its derivatives, styrene-maleic anhydride copolymer hydrolyzate, ethylene-maleic anhydride copolymer hydrolyzate, isobutyrene-maleic anhydride copolymer hydrolyzate, poly(vinyl alcohol), carboxyl-modified poly(vinyl alcohol), polyacrylamide and so on. The water-insoluble polymer includes styrene-butadiene rubber latex, acrylonitrile-butadiene rubber latex and vinyl acetate emulsion, among others.

The wax includes, among preferred species, paraffin wax, carboxyl-modified paraffin wax and polyethylene wax.

The metal soap includes metal salts of higher fatty acids. Among preferred species are zinc stearate, calcium stearate and aluminum stearate.

The antioxidant that can be used includes hindered phenol compounds.

The ultraviolet absorber includes, UV absorbers in the benzophenone series and these in the benzotriazole series.

The following examples are intended to describe this invention in further detail and should by no means been construed as defining the scope of the invention.

EXAMPLES

Example 1

Production of 3-[1-(1-ethyl-2-methylindol-3-yl)-1-(4-methylphenyl)ethylen-2-yl]-3-(4-diethylaminophenyl) phthalide (compound 1)

6.9 g (0.025 mol) of 1-(1-ethyl-2-methylindol-3-yl)-1-(4-methylphenyl)ethylene, 7.4 g (0.025 mol) of 2-(4- diethylaminobenzoyl)benzoic acid, 5.1 g (0.05 mol) of acetic anhydride and 10 mL of toluene were stirred together at 50°–55° C. for 4 hours. After cooling, 100 mL of toluene and 50 g of 10% sodium hydroxide (aqueous) were added. The mixture was stirred under reflux for 1 hour and the toluene layer was then separated, washed with warm water, filtered and concentrated. The residue was stirred in 50 mL of methanol under reflex for 1 hour. After cooling, the precipitate was collected by filtration and dried to provide 8.0 g (yield 58%) of white powder. m.p. 156°–157° C. This powder was verified by mass spectrometry and elemental analysis to be the title phthalide compound. Its infrared absorption spectrum is presented in FIG. 1. MS (m/z): 554 (M$^+$)

| Elemental analysis: | C | H | N |
| --- | --- | --- | --- |
| Calcd. (C$_{38}$H$_{38}$N$_2$O$_2$) | 82.26% | 6.92% | 5.05% |
| Found | 82.20% | 6.98% | 5.02% |

The 1-(1-ethyl-2-methylindol-3-yl)-1-(4-methylphenyl)ethylene used in this example was synthesized in the following manner.

47.7 g (0.3 mol) of 1-ethyl-2-methylindole, 60.3 g (0.45 mol) of 4'-methylacetophenone, 1.0 g of p-toluenesulfonic acid monohydrate and 150 mL of toluene were stirred together at 118°–120° C. for 5 hours and after cooling, 100 g of 1% sodium hydroxide (aq.) was added. The mixture was further stirred for 1 hour, after which the toluene layer was separated, washed with warm water, filtered and concentrated. The residue was subjected to column chromatography on silica gel using hexane as an eluent to provide 70 g (yield 85%) of light-red liquid. This liquid was verified by the following analyses to be the objective ethylene compound. MS (m/z): 275 (M$^+$)

| Elemental analysis: | C | H | N |
| --- | --- | --- | --- |
| Calcd. (C$_{20}$H$_{21}$N) | 87.21% | 7.70% | 5.09% |
| Found | 87.12% | 7.95% | 5.13% |

The 2-(4-diethylaminobenzoyl)benzoic acid used was synthesized in the following manner.

To a mixture of 300 g of chlorobenzene and 134 g of aluminum chloride was added 149 g (1 mol) of diethylaniline dropwise under ice-cooling and stirring. Then, 74 g (0.5 mol) of phthalic anhydride was added slowly and the mixture was stirred at 45°–50° C. for 4 hours. The reaction mixture was poured into 1 L of water and the chlorobenzene was distilled off. The precipitate was collected by filtration, washed with warm water, dried and recrystallized from methanol to provide 122.5 g (yield 82.5%) of yellow-white powder. m.p. 183.5°–184° C. This powder was verified by the following analyses to be the objective benzoic acid derivative. MS (m/z): 297 (M$^+$)

| Elemental analysis: | C | H | N |
| --- | --- | --- | --- |
| Calcd. (C$_{18}$H$_{19}$NO$_3$) | 72.69% | 6.45% | 4.71% |
| Found | 72.62% | 6.40% | 4.72% |

Example 2

Production of 3-[1-(1-ethyl-2-methylindol-3-yl)-1-phenylethylen-2-yl]-3-(4-dimethylaminophenyl)phthalide (compound 13)

Figure 2:
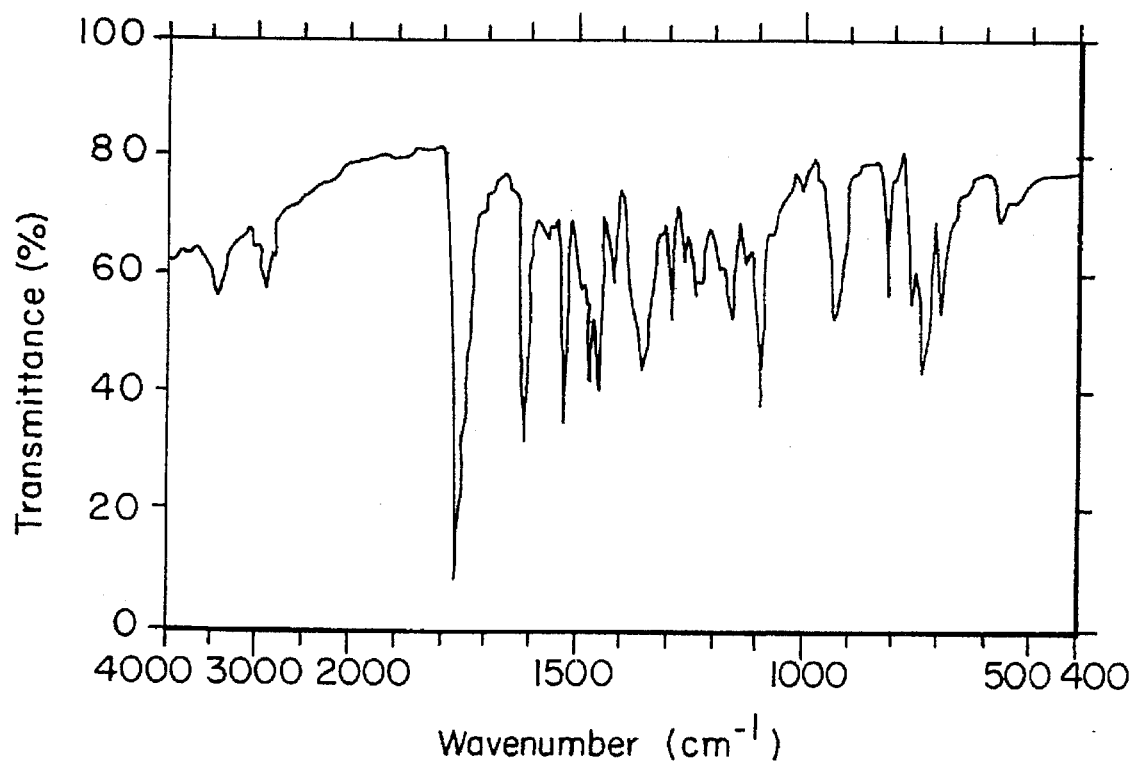
FIG. 2 is an infrared absorption spectrum of compound 13 as synthesized in Example 2.

9.6 g (0.037 mol) of 1-(1-ethyl-2-methylindol-3-yl)-1-phenylethylene, 10.0 g (0.037 mol) of 2-(4-dimethylaminobenzoyl)benzoic acid, 7.5 g (0.074 mol) of acetic anhydride and 15 mL of toluene were stirred together at 55°–60° C. for 4.5 hours. After cooling, 100 mL of toluene and 50 g of 10% sodium hydroxide (aq.) were added. The mixture was stirred for 1 hour, after which the toluene layer was taken, washed with warm water, filtered and concentrated. The residue was subjected to column chromatography on silica gel using toluene as an eluent to fractionally isolate the objective compound. This product was further stirred in 50 mL of IPA under reflux for 1 hour. After cooling, the precipitate was collected by filtration and dried to provide 8.1 g (yield 42%) of white powder. m.p. 163°–165° C. Based on the following mass spectrum and elemental analysis, this powder was confirmed to be the title phthalide compound. Its infrared absorption spectrum is presented in FIG. 2. MS (m/z): 512 (M$^+$)

| Elemental analysis: | C | H | N |
| --- | --- | --- | --- |
| Calcd. (C$_{35}$H$_{32}$N$_2$O$_2$) | 81.99% | 6.30% | 5.47% |
| Found | 81.83% | 6.26% | 5.46% |

The 1-(1-ethyl-2-methylindol-3-yl)-1-phenylethylene used in this example was synthesized in the following manner.

95.5 g (0.6 mol) of 1-ethyl-2-methylindole, 79.3 g (0.66 mol) of acetophenone, 2.0 g of p-toluenesulfonic acid monohydrate and 300 mL of toluene were stirred together at 118°–120° C. for 5 hours and after cooling, 200 g of 1% sodium hydroxide (aq.) was added. The mixture was further stirred for 1 hour, after which the toluene layer was taken, washed with warm water, filtered and concentrated. The residue was subjected to column chromatography on silica gel using hexane as an eluent to provide 148 g (yield 94%) of light-red liquid. This liquid was verified by the following analyses to be the objective ethylene compound. MS (m/z): 261 (M$^+$)

| Elemental analysis: | C | H | N |
| --- | --- | --- | --- |
| Calcd. (C$_{19}$H$_{19}$N) | 87.30% | 7.34% | 5.36% |
| Found | 86.72% | 7.75% | 4.56% |

The 2-(4-diethylaminobenzoyl)benzoic acid used was synthesized in the following manner.

To a mixture of 300 g of chlorobenzene and 134 g of aluminum chloride was added 121 g (1 mol) of dimethylaniline dropwise under ice-cooling and stirring. Then, 74 g (0.5 mol) of phthalic anhydride was added slowly and the mixture was stirred at 45°–50° C. for 4 hours. The reaction mixture was poured into 1 L of water and the chlorobenzene was distilled off. The precipitate was collected by filtration, washed with warm water, dried and recrystallized from methanol to provide 111 g (yield 82.5%) of yellow-white powder. m.p. 198°–199° C. This powder was verified by the following analyses to be the objective benzoic acid derivative. MS (m/z): 269 (M$^+$)

| Elemental analysis: | C | H | N |
|---|---|---|---|
| Calcd. (C$_{16}$H$_{15}$NO$_3$) | 71.35% | 5.63% | 5.20% |
| Found | 71.32% | 5.56% | 5.19% |

Example 3

Production of 3-[1-(1-n-butyl-2-methylindol-3-yl)-1-(4-n-butylphenyl)ethylen-2-yl]-3-(4-di-n-butylaminophenyl)phthalide (compound 23)

13.8 g (0.04 mol) of 1-(1-n-butyl-2-methylindol-3-yl)-1-(4-n-butylphenyl)ethylene, 14.2 g (0.04 mol) of 2-(4-di-n-butylaminobenzoyl)benzoic acid, 8.1 g (0.08 mol) of acetic anhydride and 16 mL of toluene were stirred together at 55°–60° C. for 4.5 hours. After cooling, 100 mL of toluene and 50 g of 10% sodium hydroxide (aq.) were added. The mixture was further stirred for 1 hour and the toluene layer was then separated, washed with warm water, filtered and concentrated. The residue was subjected to column chromatography on silica gel using toluene as an eluent and the eluate was concentrated to provide 9.6 g (yield 35%) of a colorless viscous resinous substance. This substance was verified by mass spectrometry and elemental analysis to be the title phthalide compound. MS (m/z): 680 (M$^+$)

| Elemental analysis: | C | H | N |
|---|---|---|---|
| Calcd. (C$_{47}$H$_{56}$N$_2$O$_2$) | 82.88% | 8.30% | 4.11% |
| Found | 82.70% | 8.15% | 4.03% |

The 1-(1-n-butyl-2-methylindol-3-yl)-1-(4-n-butylphenyl)ethylene used in this example was synthesized in the following manner.

23.8 g (0.127 mol) of 1-n-butyl-2-methylindole, 25 g (0.14 mol) of 4'-n-butylacetophenone, 0.4 g of p-toluenesulfonic acid monohydrate and 60 mL of toluene were stirred together at 118°–120° C. for 5 hours and after cooling, 40 g of 1% sodium hydroxide (aq.) was added. The mixture was further stirred for 1 hour, after which the toluene layer was separated, washed with warm water, filtered and concentrated. The residue was subjected to column chromatography on silica gel using hexane as an eluent to provide 35 g (yield 78%) of light-red liquid. This liquid was verified by the following analyses to be the objective ethylene compound. MS (m/z): 345 (M$^+$)

| Elemental analysis: | C | H | N |
|---|---|---|---|
| Calcd. (C$_{25}$H$_{31}$N) | 86.89% | 9.06% | 4.05% |
| Found | 86.92% | 9.07% | 4.01% |

The 2-(4-di-n-butylaminobenzoyl)benzoic acid used was synthesized in the following manner.

To a mixture of 300 g of chlorobenzene and 134 g of aluminum chloride was added 205 g (1 mol) of di-n-butylaniline dropwise under ice-cooling and stirring. Then, 74 g (0.5 mol) of phthalic anhydride was added slowly and the mixture was stirred at 45°–50° C. for 4 hours. The reaction mixture was then poured into 1 L of water and the chlorobenzene was distilled off. The precipitate was collected by filtration, washed with warm water, dried and recrystallized from methanol to provide 138 g (yield 78.2%) of yellow-white powder. m.p. 171°–172° C. This powder was verified by the following analyses to be the objective benzoic acid derivative. MS (m/z): 353 (M$^+$)

| Elemental analysis: | C | H | N |
|---|---|---|---|
| Calcd. (C$_{22}$H$_{27}$NO$_3$) | 74.74% | 7.71% | 3.36% |
| Found | 74.75% | 7.68% | 4.02% |

Example 4

Production of 3-[1-(1-ethyl-2-phenylindol-3-yl)-1-phenylethylen-2-yl]-3-(4-dimethylaminophenyl)phthalide (compound 41)

Figure 3:
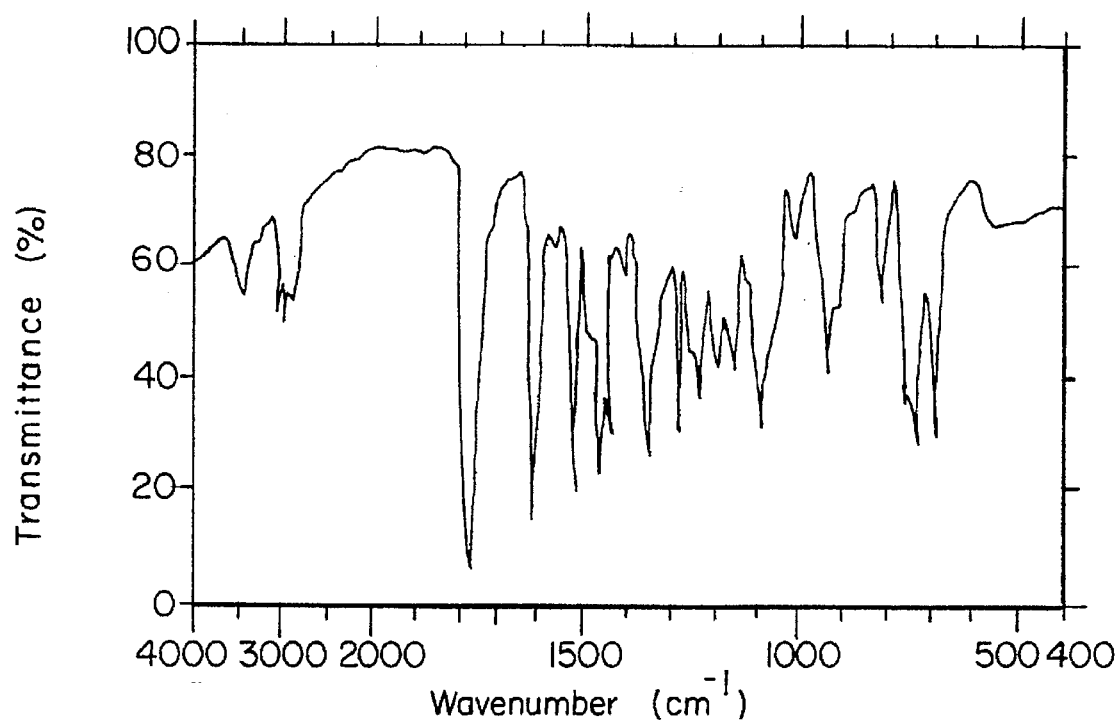
FIG. 3 is an infrared absorption spectrum of compound 41 as synthesized in Example 4.

12 g (0.037 mol) of 1-(1-ethyl-2-phenylindol-3-yl)-1-phenylethylene, 10 g (0.037 mol) of 2-(4-dimethylaminobenzoyl)benzoic acid, 7.5 g (0.074 mol) of acetic anhydride and 15 mL of toluene were stirred together at 55°–60° C. for 4.5 hours. After cooling, 150 mL of toluene and 75 g of 10% sodium hydroxide (aq.) were added. The mixture was stirred under reflux for 1 hour and the toluene layer was then taken, washed with warm water, filtered and concentrated. The residue was stirred in 70 ml of IPA under reflux for 1 hour. After cooling, the precipitate was collected by filtration and dried to provide 4.6 g (yield 21.6%) of light yellow powder. m.p. 85°–88° C. This powder was verified by mass spectrometry and elemental analysis to be the title phthalide compound. Its infrared absorption spectrum is presented in FIG. 3. MS (m/z): 574 (M$^+$)

| Elemental analysis: | C | H | N |
|---|---|---|---|
| Calcd. (C$_{40}$H$_{34}$N$_2$O$_2$) | 83.58% | 5.97% | 4.88% |
| Found | 83.60% | 5.90% | 4.81% |

The 1-(1-ethyl-2-phenylindol-3-yl)-1-phenylethylene used in this example was synthesized in the following manner.

66.4 g (0.3 mol) of 1-ethyl-2-phenylindole, 39.6 g (0.33 mol) of acetophenone, 1.0 g of p-toluenesulfonic acid monohydrate and 150 mL of toluene were stirred together at 118°–120° C. for 5 hours and after cooling, 100 g of 1% sodium hydroxide (aq.) was added. The mixture was further stirred for 1 hour, after which the toluene layer was separated, washed with warm water, filtered and concentrated. The residue was subjected to column chromatography on silica gel using hexane as an eluent to provide 10 g (yield 10%) of light-red liquid. This liquid was verified by the following analyses to be the objective ethylene compound. MS (m/z): 323 (M$^+$)

| Elemental analysis: | C | H | N |
|---|---|---|---|
| Calcd. (C$_{24}$H$_{21}$N) | 89.11% | 6.56% | 4.33% |
| Found | 89.02% | 6.60% | 4.28% |

Example 5

Production of 3-[1-(1-ethyl-2-methylindol-3-yl)-1-phenylethylen-2-yl]-3-(4-diethylaminophenyl)phthalide (compound 57)

Figure 4:
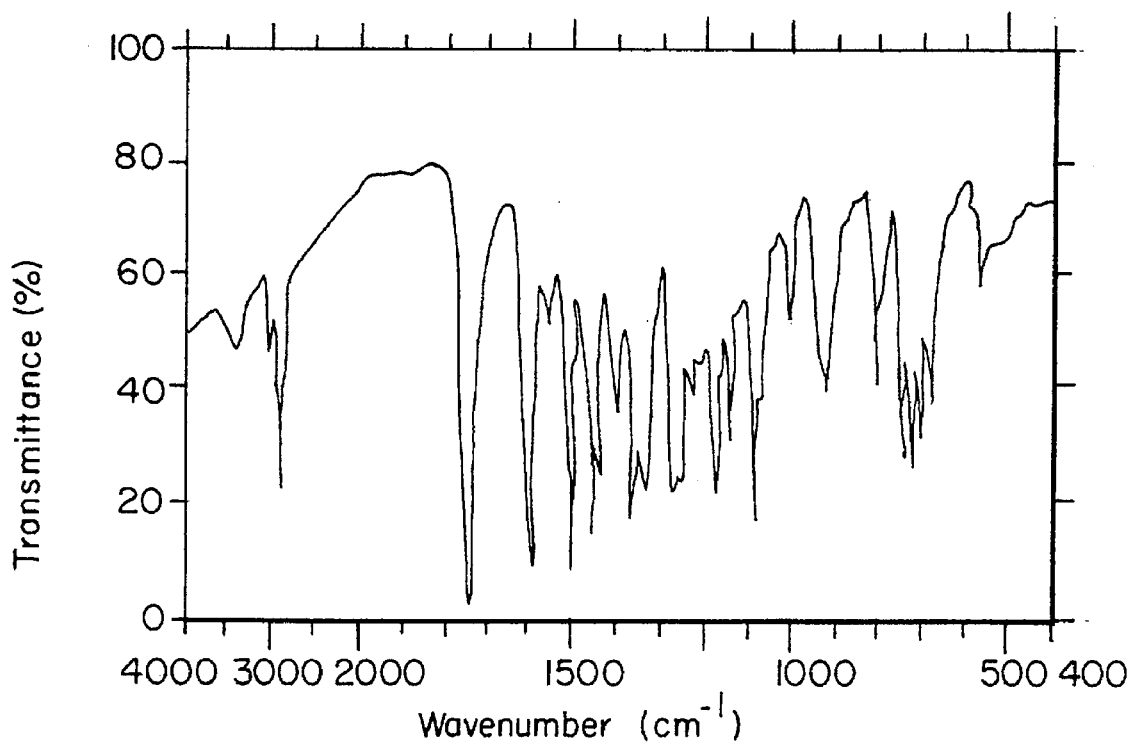
FIG. 4 is an infrared absorption spectrum of compound 57 as synthesized in Example 5.

18.3 g (0.07 mol) of 1-(1-ethyl-2-methylindol-3-yl)-1-phenylethylene, 20.8 g (0.07 mol) of 2-(4-diethylaminobenzoyl)benzoic acid, 14.2 g (0.14 mol) of acetic anhydride and 28 mL of toluene were stirred together at 55°–60° C. for 5 hours. After cooling, 150 mL of toluene and 75 g of 10% sodium hydroxide (aq.) were added. The mixture was stirred for 1 hour, after which the toluene layer was separated, washed with warm water, filtered and concentrated. The residue was subjected to column chromatography on silica gel using toluene as an eluent to isolate the objective compound. After concentration, this product was further stirred in 70 mL of IPA under reflux for 1 hour. After cooling, the precipitate was collected by filtration and dried to provide 4.6 g (yield 17.9%) of white powder. m.p. 123°–126° C. Based on the following mass spectrum and elemental analysis, this powder was confirmed to be the title phthalide compound. Its infrared absorption spectrum is presented in FIG. 4. MS (m/z): 540 ($M^+$)

| Elemental analysis: | C | H | N |
|---|---|---|---|
| Calcd. ($C_{37}H_{36}N_2O_2$) | 82.18% | 6.72% | 5.18% |
| Found | 81.99% | 6.75% | 5.13% |

Example 6

Production of 3-[1-(1-ethyl-2-methylindol-3-yl)-1-phenylethylen-2-yl]-3-(2-methyl-4-diethylaminophenyl)phthalide (compound 70)

Figure 5:
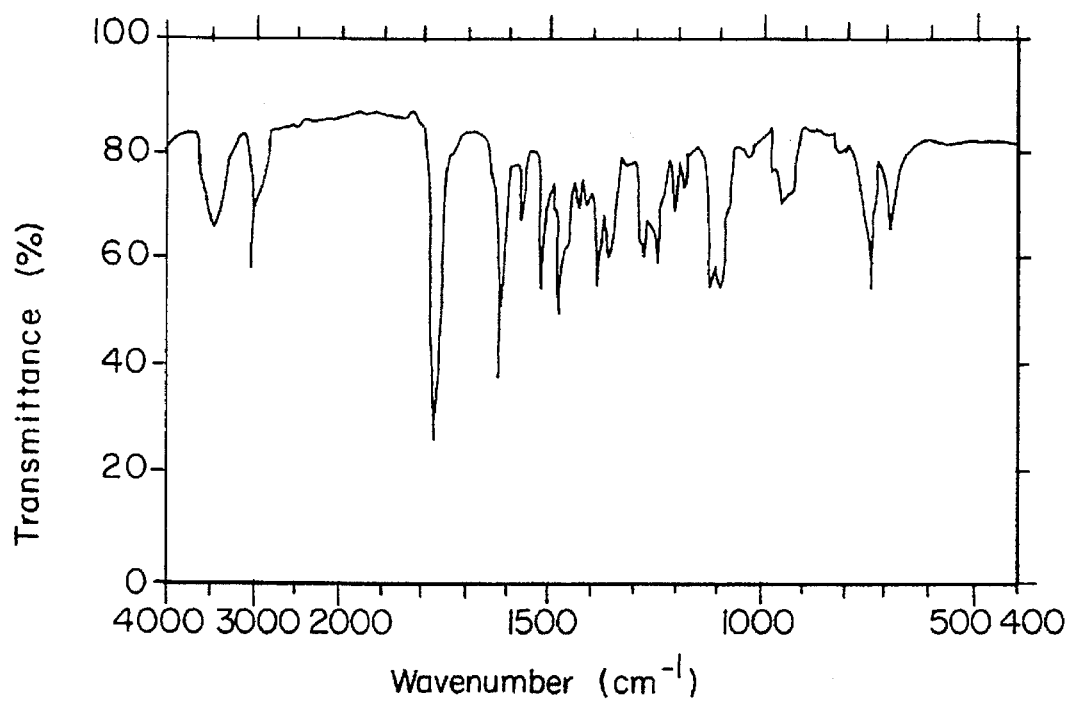
FIG. 5 is an infrared absorption spectrum of compound 70 as synthesized in Example 6.

9.6 g (0.037 mol) of 1-(1-ethyl-2-methylindol-3-yl)-1-phenylethylene, 11.5 g (0.037 mol) of 2-(2-methyl-4-diethylaminobenzoyl)benzoic acid, 7.5 g (0.074 mol) of acetic anhydride and 15 mL of toluene were stirred together at 55°–60° C. for 4.5 hours. After cooling, 100 mL of toluene and 50 g of 10% sodium hydroxide (aq.) were added. The mixture was stirred for 1 hour, after which time the toluene layer was taken, washed with warm water, filtered and concentrated. The residue was subjected to column chromatography on silica gel using toluene as an eluent to isolate the objective compound. This product was further stirred in 50 mL of IPA under reflux for 1 hour. After cooling, the precipitate was collected by filtration and dried to provide 4.7 g (yield 22%) of white powder. m.p. 115°–118° C. Based on the following mass spectrum and elemental analysis, this powder was confirmed to be the title phthalide compound. Its infrared absorption spectrum is presented in FIG. 5. MS (m/z): 554 ($M^+$)

| Elemental analysis: | C | H | N |
|---|---|---|---|
| Calcd. ($C_{38}H_{38}N_2O_2$) | 82.26% | 6.92% | 5.05% |
| Found | 82.29% | 6.85% | 5.08% |

The 2-(2-methyl-4-diethylaminobenzoyl)benzoic acid used in this example was synthesized in the following manner.

To a mixture of 295 g of chlorobenzene and 134 g of aluminum chloride was added 163 g (1 mol) of diethyltoluidine dropwise under ice-cooling and stirring. Then, 74 g (0.5 mol) of phthalic anhydride was added slowly and the mixture was stirred at 45°–50° C. for 4 hours. The reaction mixture was then poured into 1 L of water and the chlorobenzene was distilled off. The precipitate was collected by filtration, washed with warm water, dried and recrystallized from methanol to provide 116 g (yield 74.6%) of white powder. m.p. 142°–142.5° C. This powder was verified by the following analyses to be the objective benzoic acid derivative. MS (m/z): 311 ($M^+$)

| Elemental analysis: | C | H | N |
|---|---|---|---|
| Calcd. ($C_{19}H_{21}NO_3$) | 73.28% | 6.81% | 4.50% |
| Found | 72.18% | 6.84% | 4.38% |

Example 7

Production of 3-[1-(1-n-octyl-2-phenylindol-3-yl)-1-phenylethylen-2-yl]-3-(4-diethylaminophenyl)phthalide (compound 84)

28.5 g (0.07 mol) of 1-(1-n-octyl-2-phenylindol-3-yl)-1-phenylethylene, 20.8 g (0.07 mol) of 2-(4-diethylaminobenzoyl)benzoic acid, 14.2 g (0.14 mol) of acetic anhydride and 28 mL of toluene were stirred together at 55°–60° C. for 4 hours. After cooling, 100 mL of toluene and 50 g of 10% sodium hydroxide (aq.) were added. The mixture was stirred for 1 hour, after which the toluene layer was separated, washed with warm water, filtered and concentrated. The residue was subjected to column chromatography on silica gel using toluene as an eluent and the eluate was concentrated to provide 7.2 g (yield 15%) of a colorless viscous resinous substance. This substance was verified by mass spectrometry and elemental analysis to be the title phthalide compound. MS (m/z): 686 ($M^+$)

| Elemental analysis: | C | H | N |
|---|---|---|---|
| Calcd. ($C_{48}H_{50}N_2O_2$) | 83.91% | 7.35% | 4.08% |
| Found | 83.96% | 7.30% | 4.05% |

The 1-(1-n-octyl-2-phenylindol-3-yl)-1-phenylethylene used in this example was synthesized in the following manner.

61.0 g (0.2 mol) of 1-n-octyl-2-phenylindole, 26.4 g (0.22 mol) of acetophenone, 1.0 g of p-toluenesulfonic acid monohydrate and 100 mL of toluene were stirred together at 118°–120° C. for 5 hours and after cooling, 100 g of 1% sodium hydroxide (aq.) was added. The mixture was further stirred for 1 hour, after which the toluene layer was separated, washed with warm water, filtered and concentrated. The residue was subjected to column chromatography on silica gel using hexane as an eluent to provide 71 g (yield 87%) of light-red liquid. This liquid was verified by the following analyses to be the objective ethylene compound. MS (m/z): 407 ($M^+$)

| Elemental analysis: | C | H | N |
|---|---|---|---|
| Calcd. ($C_{30}H_{33}N$) | 88.39% | 8.18% | 3.44% |
| Found | 88.29% | 8.20% | 3.47% |

Example 8

Production of 3-[1-(1-ethyl-2-methylindol-3-yl)-1-(4-methylphenyl)ethylen-2-yl]-3-(2-ethoxy-4-di-n-butylaminophenyl)phthalide (compound 87)

41.3 g (0.15 mol) of 1-(1-ethyl-2-methylindol-3-yl)-1-(4-methylphenyl)ethylene, 59.6 g (0.15 mol) of 2-(2-ethoxy-4-di-n-butylaminobenzoyl)benzoic acid, 40.8 g (0.40 mol) of acetic anhydride and 10 mL of toluene were stirred together at 45°–50° C. for 4 hours. After cooling, 150 mL of toluene and 150 mL of warm water were added. The mixture was stirred for 1 hour, after which the toluene layer was separated, washed with warm water, filtered and concentrated.

Figure 6:
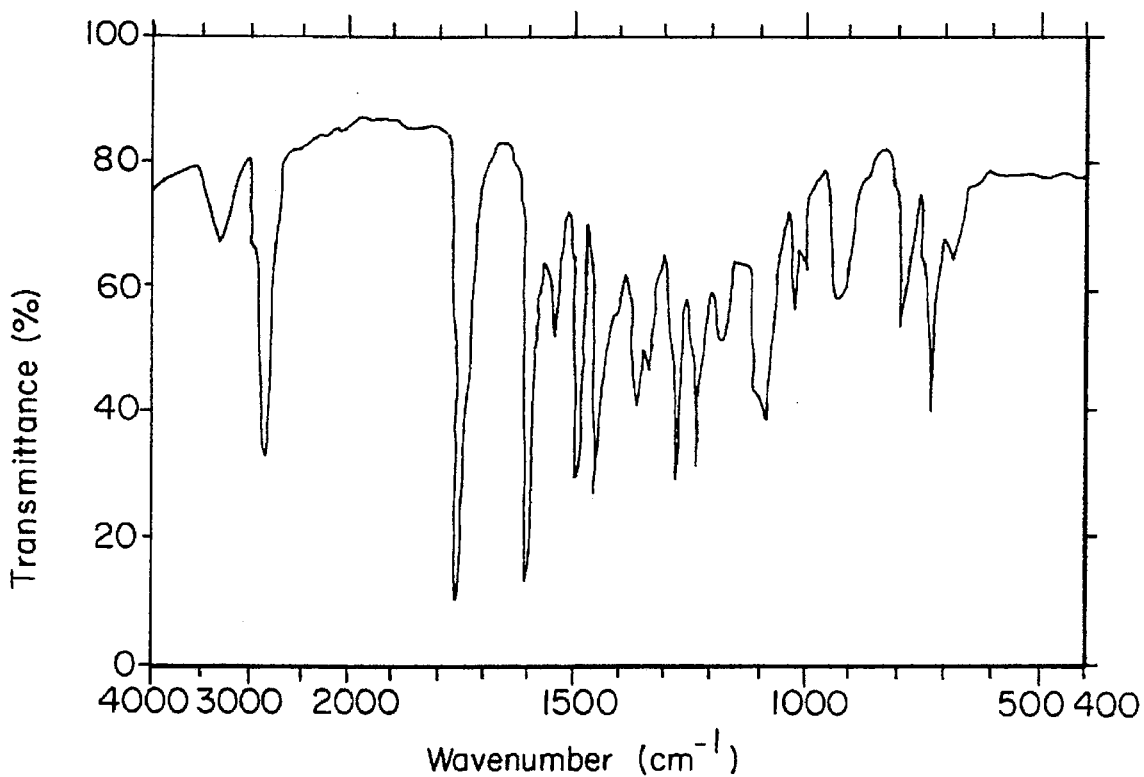
FIG. 6 is an infrared absorption spectrum of compound 87 as synthesized in Example 8.

The residue was subjected to column chromatography on silica gel using toluene as an eluent and the eluate was concentrated to provide 19.5 g (yield 19.9%) of pale brown oil. This oil was verified by mass spectrometry and elemental analysis to be the title phthalide compound. Its infrared absorption spectrum is presented in FIG. 6. MS (m/z): 654 ($M^+$)

| Elemental analysis: | C | H | N |
|---|---|---|---|
| Calcd. ($C_{44}H_{50}N_2O_3$) | 80.70% | 7.70% | 4.28% |
| Found | 80.70% | 7.81% | 4.33% |

The 2-(2-ethoxy-4-di-n-butylaminobenzoyl)benzoic acid used in this example was synthesized in the following manner.

To a mixture of 325 g of chlorobenzene and 149.9 g of aluminum chloride was added 274.3 g (1.1 mol) of 3-n-ethoxy-N,N-di-n-butylaniline dropwise under ice-cooling and stirring. Then, 81.5 g (0.55 mol) of phthalic anhydride was added and the mixture was stirred at 45°–50° C. for 4 hours. The reaction mixture was then poured into 1 L of water and the chlorobenzene was distilled off. The precipitate was taken, diluted with 200 mL of toluene and extracted with aqueous sodium hydroxide solution. The extract was precipitated from diluted hydrochloric acid and the precipitate was recovered, washed with warm water and dried. It was then recrystallized from toluene-methanol to provide 111.8 g (yield 51.1%) of yellowish white powder. This powder was verified by the following analyses to be the objective benzoic acid derivative. MS (m/z): 397 ($M^+$)

| Elemental analysis: | C | H | N |
|---|---|---|---|
| Calcd. ($C_{24}H_{31}NO_4$) | 72.52% | 7.86% | 3.52% |
| Found | 72.46% | 7.81% | 3.49% |

Example 9

Production of 3-[1-(1-ethyl-2-methylindol-3-yl)-1-(4-methylphenyl)ethylen-2-yl]-3-[2-n-butoxy-4-diethylaminophenyl)phthalide (compound 89)

Figure 7:
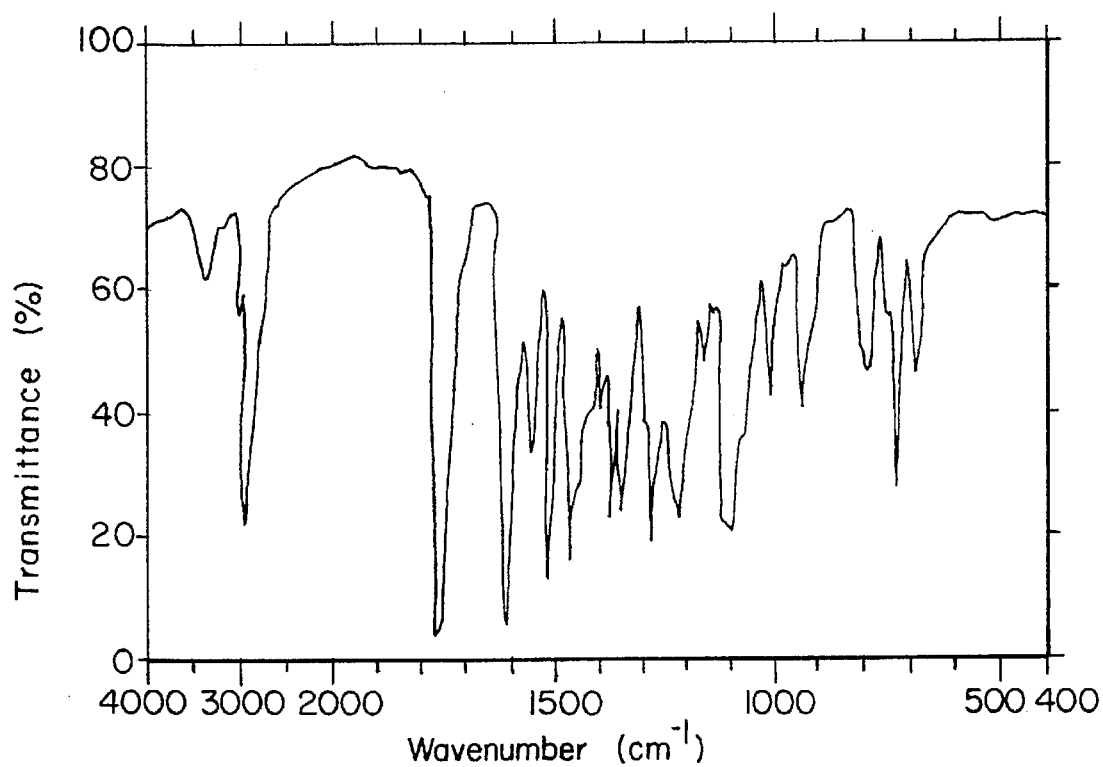
FIG. 7 is an infrared absorption spectrum of compound 89 as synthesized in Example 9.

41.3 g (0.15 mol) of 1-(1-ethyl-2-methylindol-3-yl)-1-(4-methylphenyl)ethylene, 55.4 g (0.15 mol) of 2-(2-n-butoxy-4-dimethylaminobenzoyl)benzoic acid, 40.8 g (0.40 mol) of acetic anhydride and 15 mL of toluene were stirred together at 55°–60° C. for 4.5 hours. After cooling, 150 mL of toluene and 150 mL of warm water were added. The mixture was stirred for 1 hour, after which time the toluene layer was separated, washed with warm water, filtered and concentrated. The residue was subjected to column chromatography on silica gel using toluene as an eluent and the eluate was concentrated to provide 16.1 g (yield 17.1%) of yellow oil. This oil was verified by mass spectrometry and elemental analysis to be the title phthalide compound. Its infrared absorption spectrum is presented in FIG. 7. MS (m/z): 626 ($M^+$)

| Elemental analysis: | C | H | N |
|---|---|---|---|
| Calcd. ($C_{42}H_{46}N_2O_3$) | 80.48% | 7.40% | 4.47% |
|  | 80.55% | 7.38% | 4.48% |

The 2-(2-n-butoxy-4-diethylaminobenzoyl)benzoic acid used in this example was synthesized in the following manner.

To a mixture of 325 g of chlorobenzene and 149.9 g of aluminum chloride was added 243.1 g (1.1 mol) of 3-n-ethoxy-N,N-di-n-butylaniline dropwise under ice-cooling and stirring. Then, 81.4 g (0.55 mol) of phthalic anhydride was added and the mixture was stirred at 45°–50° C. for 4 hours. The reaction mixture was then poured into 1 L of water and the chlorobenzene was distilled off. The oil layer was separated, diluted with 200 mL of toluene and extracted with aqueous sodium hydroxide solution. The extract was treated with diluted hydrochloric acid and the resulting precipitate was collected and washed with warm water. It was then recrystallized from toluene-methanol to provide 100.6 g (yield 49.5%) of yellowish white powder. This powder was verified by the following analyses to be the objective benzoic acid derivative. MS (m/z): 369 ($M^+$)

| Elemental analysis: | C | H | N |
|---|---|---|---|
| Calcd. ($C_{22}H_{27}NO_4$) | 71.52% | 7.37% | 3.79% |
| Found | 71.59% | 7.31% | 3.83% |

Example 10

Production of 3-[1-(1-ethyl-2-methylindol-3-yl)-1-phenylethylen-2-yl]-3-[4-N-ethyl-N-(4-ethoxyphenyl)aminophenyl]phthalide (compound 91)

Figure 8:
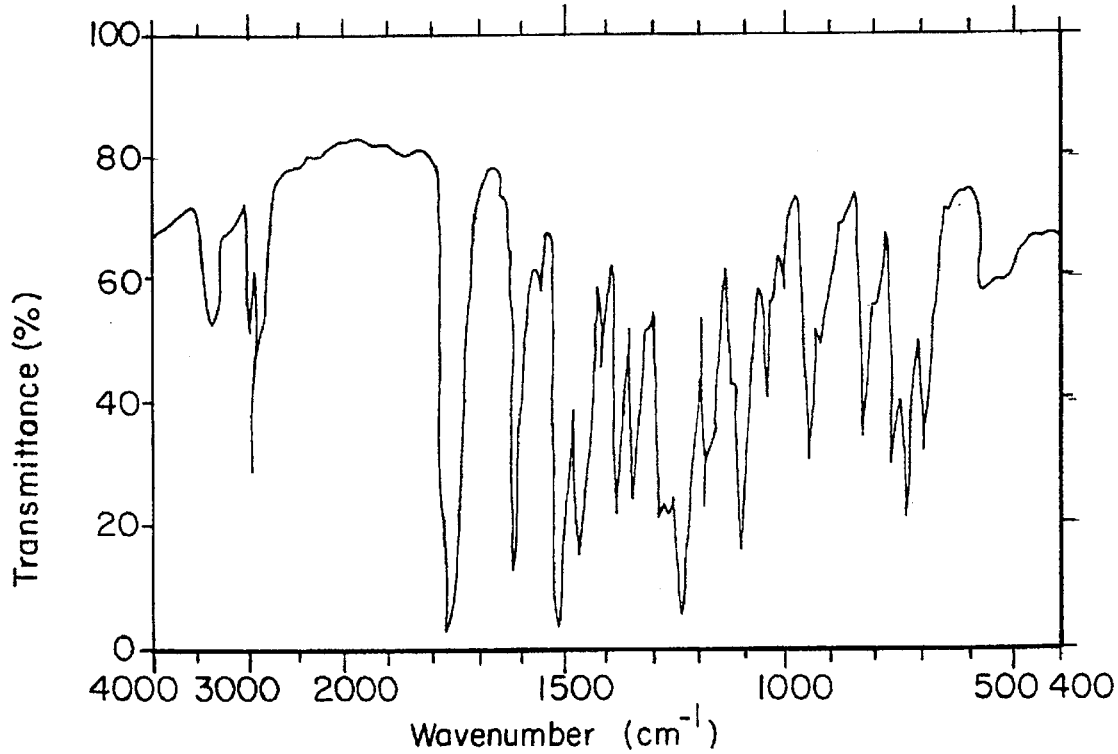
FIG. 8 is an infrared absorption spectrum of compound 91 as synthesized in Example 10.

20.9 g (0.08 mol) of 1-(1-ethyl-2-methylindol-3-yl)-1-phenylethylene, 31.1 g (0.08 mol) of 2-[4-N-ethyl-N-(4-ethoxyphenyl)aminobenzoyl)benzoic acid, 16.3 g (0.16 mol) of acetic anhydride and 33 mL of toluene were stirred together at 60°–65° C. for 4 hours. After cooling, 300 mL of toluene and 180 g of 2% sodium hydroxide (aq.) were added. The mixture was further stirred for 1 hour and the toluene layer was then separated, washed with warm water, filtered and concentrated. The residue was subjected to column chromatography on silica gel using toluene as an eluent and the eluate was concentrated. The residue was stirred in 500 mL of n-hexane under reflux for 1 hour. After cooling, the precipitate was collected by filtration and dried to provide 9.1 g (yield 18%) of white powder. m.p. 112°–113° C. This powder was verified by mass spectrometry and elemental analysis to be the title phthalide compound. Its infrared absorption spectrum is presented in FIG. 8. MS (m/z): 632 ($M^+$)

| Elemental analysis: | C | H | N |
|---|---|---|---|
| Calcd. ($C_{43}H_{40}N_2O_3$) | 81.62% | 6.37% | 4.43% |
| Found | 81.73% | 6.32% | 4.49% |

The 2-[4-N-ethyl-N-(4-ethoxyphenyl)aminobenzoyl)benzoic acid used in this example was synthesized in the following manner.

To a mixture of 319 g of chlorobenzene and 160.0 g of aluminum chloride was added 136.2 g (0.56 mol) of N-ethyl-N-(4-ethoxyphenyl)aniline dropwise under ice-cooling and stirring. Then, 88.8 g (0.60 mol) of phthalic anhydride was added and the mixture was stirred at 45°–50° C. for 4 hours. The reaction mixture was then poured into 1 L of water and the chlorobenzene was distilled off. The oil layer was separated, diluted with 100 mL of toluene and extracted with aqueous sodium hydroxide solution. The extract was treated with diluted hydrochloric acid and the resulting precipitate was collected by filtration, washed with warm water and dried. It was then recrystallized from methanol to provide 74.6 g (yield 34.2%) of green-white powder. This powder was verified by the following analyses to be the objective benzoic acid derivative. MS (m/z): 389 (M⁺)

| Elemental analysis: | C | H | N |
|---|---|---|---|
| Calcd. ($C_{24}H_{23}NO_4$) | 74.02% | 5.95% | 3.60% |
| Found | 73.98% | 5.91% | 3.54% |

Example 11

Production of 3-[1-(1-ethyl-2-methylindol-3-yl)-1-(2-methylphenyl)ethylen-2-yl]-3-(4-diethylaminophenyl)phthalide (compound 92)

Figure 9:
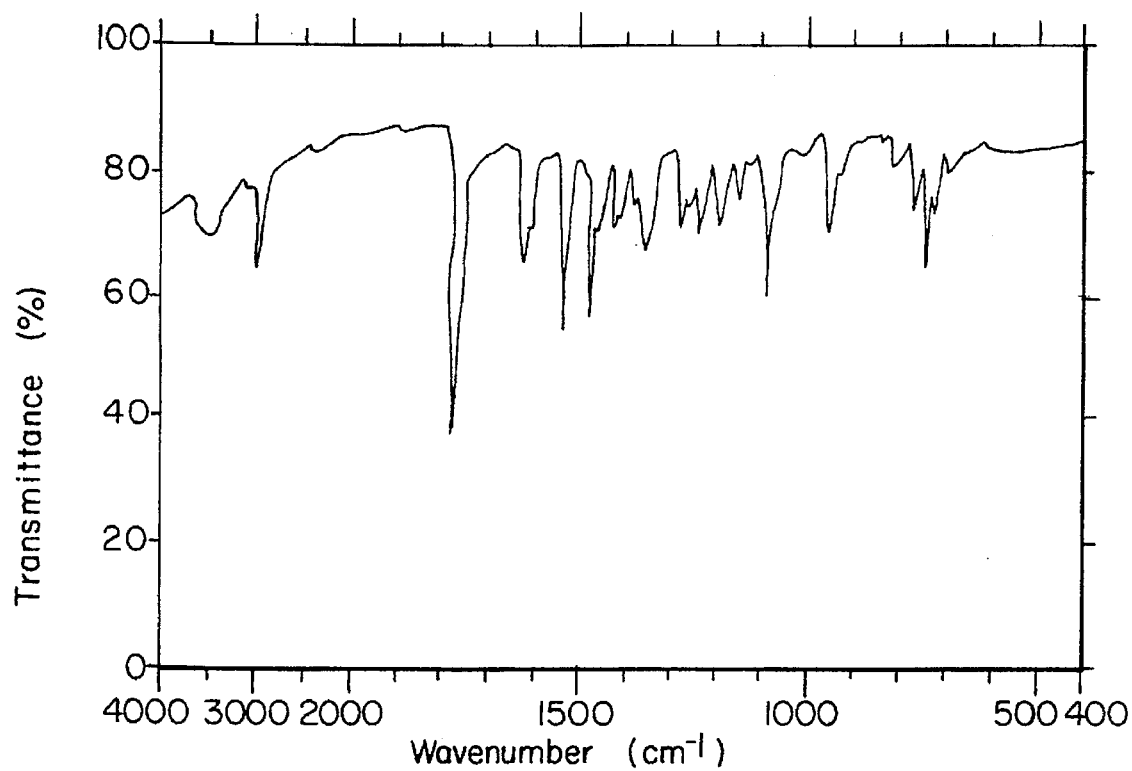
FIG. 9 is an infrared absorption spectrum of compound 92 as synthesized in Example 11.

110.2 g (0.40 mol) of 1-(1-ethyl-2-methylindol-3-yl)-1-(2-methylphenyl)ethylene, 118.9 g (0.40 mol) of 2-(4-diethylaminobenzoyl)benzoic acid, 81.7 g (0.80 mol) of acetic anhydride and 160 mL of toluene were stirred together at 50°–55° C. for 5 hours. After cooling, 700 mL of toluene and 200 g of 5% sodium hydroxide (aq.) were added. The mixture was stirred under reflux for 2 hours and the toluene layer was then separated, washed with warm water, filtered and concentrated. The residue was stirred in 1500 ml of methanol under reflex for 1 hour. After cooling, the precipitate was collected by filtration and dried to provide a yellow-white powder. The powder was recrystallized from a solvent mixture of 1500 mL of methanol and 750 mL of toluene to give 87.2 g (yield 39.3%) of white powder. m.p. 188°–190° C. This powder was verified by mass spectrometry and elemental analysis to be the title phthalide compound. Its infrared absorption spectrum is presented in FIG. 9. MS (m/z): 554 (M⁺)

| Elemental analysis: | C | H | N |
|---|---|---|---|
| Calcd. ($C_{38}H_{38}N_2O_2$) | 82.28% | 6.90% | 5.05% |
| Found | 82.33% | 6.89% | 5.09% |

The 1-(1-ethyl-2-methylindol-3-yl)-1-(2-methylphenyl)ethylene used in this example was synthesized in the following manner.

79.6 g (0.50 mol) of 1-ethyl-2-methylindole, 80.5 g (0.60 mol) of 2'-methylacetophenone, 1.5 g of p-toluenesulfonic acid monohydrate and 200 mL of toluene were stirred together at 118°–120° C. for 4 hours and after cooling, 600 g of 1% sodium hydroxide (aq.) was added. The mixture was further stirred for 10 minutes, after which the toluene layer was separated, washed with warm water, filtered and concentrated. The residue was subjected to column chromatography on silica gel using hexane as an eluent to provide 117.0 g (yield 85%) of light-red liquid. Based on the following analyses, this liquid was confirmed to be the objective ethylene compound. MS (m/z): 275 (M⁺)

| Elemental analysis: | C | H | N |
|---|---|---|---|
| Calcd. ($C_{20}H_{21}N$) | 87.23% | 7.69% | 5.09% |
| Found | 87.30% | 7.75% | 5.01% |

Example 12

Production of 3-[1-(1-ethyl-2-methylindol-3-yl)-1-(3-methylphenyl)ethylen-2-yl]-3-(4-diethylaminophenyl)phthalide (compound 97)

Figure 10:
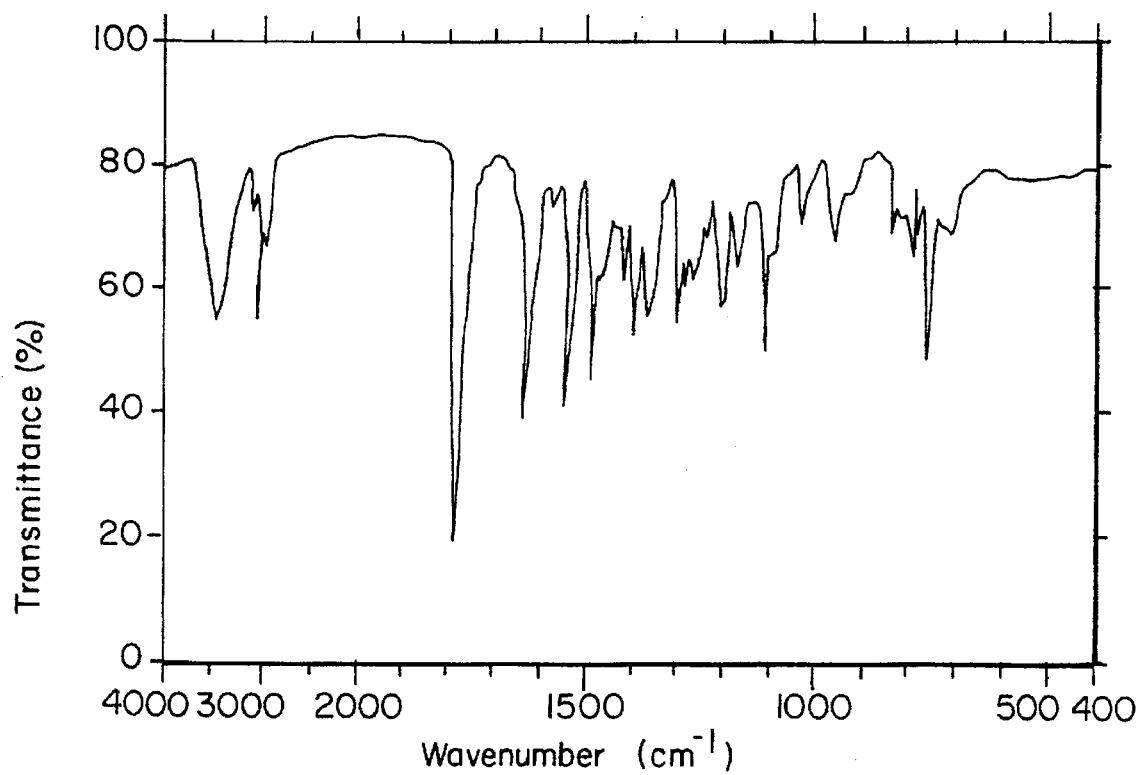
FIG. 10 is an infrared absorption spectrum of compound 97 as synthesized in Example 12.

82.6 g (0.30 mol) of 1-(1-ethyl-2-methylindol-3-yl)-1-(3-methylphenyl)ethylene, 89.2 g (0.30 mol) of 2-(4-diethylaminobenzoyl)benzoic acid, 61.3 g (0.60 mol) of acetic anhydride and 120 mL of toluene were stirred together at 50°–55° C. for 4.0 hours. After cooling, 1000 mL of toluene and 500 g of 5% sodium hydroxide (aq.) were added. The mixture was stirred for 1 hour and the toluene layer was then separated, washed with warm water, filtered and concentrated. The residue was subjected to column chromatography on silica gel using toluene as an eluent to isolate the objective compound. This product was purified by recrystallization from a mixture of 200 mL of methanol and 40 mL of toluene to give a white granular precipitate. The melting point of this granular product was 105°–112° C. (a foam produced). The granules were stirred in 800 mL of n-hexane under reflux for 1 hour. After cooling, the precipitate was collected by filtration and dried to provide 36.1 g (yield 21.7%) of white powder. m.p. 104°–105° C. This powder was verified by mass spectrometry and elemental analysis to be the title phthalide compound. Its infrared absorption spectrum is presented in FIG. 10. MS (m/z): 554 (M⁺)

| Elemental analysis: | C | H | N |
|---|---|---|---|
| Calcd. ($C_{38}H_{38}N_2O_2$) | 82.28% | 6.90% | 5.05% |
| Found | 82.20% | 6.85% | 5.11% |

The 1-(1-ethyl-2-methylindol-3-yl)-1-(3-methylphenyl)ethylene used in this example was synthesized in the following manner.

47.7 g (0.30 mol) of 1-ethyl-2-methylindole, 41.5 g (0.31 mol) of 3'-methylacetophenone, 1.0 g of p-toluenesulfonic acid monohydrate and 150 mL of toluene were stirred together at 118°–120° C. for 4 hours and after cooling, 300 g of 1% sodium hydroxide (aq.) was added. The mixture was further stirred for 1 hour, after which the toluene layer was separated, washed with warm water, filtered and concentrated. The residue was subjected to column chromatography on silica gel using hexane as an eluent to provide 58.7 g (yield 71%) of light-red liquid. This liquid was verified by the following analyses to be the objective ethylene compound. MS (m/z): 275 (M⁺)

| Elemental analysis: | C | H | N |
|---|---|---|---|
| Calcd. ($C_{20}H_{21}N$) | 87.23% | 7.69% | 5.09% |
| Found | 87.31% | 7.78% | 4.99% |

Example 13

Production of 3-[1-(1-ethyl-2-methylindol-3-yl)-1-(4-methoxyphenyl)ethylen-2-yl]-3-(4-diethylaminophenyl)phthalide (compound 98)

Figure 11:
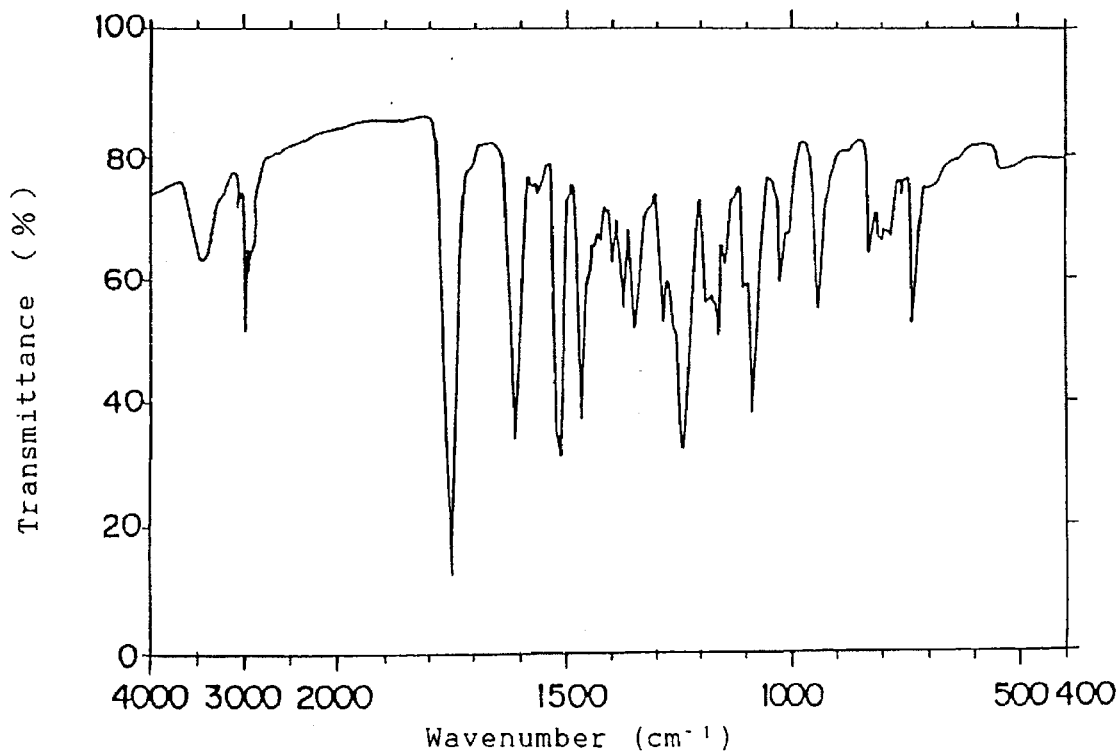
FIG. 11 is an infrared absorption spectrum of compound 98 as synthesized in Example 13.

87.4 g (0.30 mol) of 1-(1-ethyl-2-methylindol-3-yl)-1-(4-methoxyphenyl)ethylene, 89.2 g (0.30 mol) of 2-(4-diethylaminobenzoyl)benzoic acid, 61.3 g (0.60 mol) of acetic anhydride and 120 mL of toluene were stirred together at 50°–55° C. for 2.0 hours. After cooling, 800 mL of toluene and 600 g of 1% sodium hydroxide (aq.) were added. The mixture was further stirred for 1.5 hours and the toluene layer was then separated, washed with warm water, filtered and concentrated. The residue was subjected to column chromatography on silica gel using toluene as an eluent and the eluate was concentrated. The concentrate was stirred in a solvent mixture of 1200 mL of methanol and 120 mL of toluene under reflux for 1 hour. After cooling, the precipitate was collected by filtration and dried to provide white granules. m.p. 109°–115° C. (a foam produced). The granules were then stirred in 1000 ml of n-hexane under reflux for 1 hour. After cooling, the precipitate was collected by filtration and dried to provide 58.2 g (yield 34.0%) of white granules. m.p. 179°–181° C. This granular product was verified by mass spectrometry and elemental analysis to be the title phthalide compound. Its infrared absorption spectrum is presented in FIG. 11. MS (m/z): 570 (M$^+$)

| Elemental analysis: | C | H | N |
|---|---|---|---|
| Calcd. (C$_{38}$H$_{38}$N$_2$O$_3$) | 79.97% | 6.71% | 4.91% |
| Found | 80.06% | 6.81% | 4.99% |

The 1-(1-ethyl-2-methylindol-3-yl)-1-(4-methoxyphenyl)ethylene used in this example was synthesized in the following manner.

79.6 g (0.50 mol) of 1-ethyl-2-methylindole, 82.6 g (0.55 mol) of 4'-methoxyacetophenone, 1.0 g of p-toluenesulfonic acid monohydrate and 150 mL of toluene were stirred together at 118°–120° C. for 4 hours and after cooling, 100 g of 1% sodium hydroxide (aq.) was added. The mixture was further stirred for 10 minutes, after which the toluene layer was separated, washed with warm water, filtered and concentrated. The residue was subjected to column chromatography on silica gel using hexane as an eluent to provide 128.2 g (yield 88%) of light-red liquid. This liquid was verified by the following analyses to be the objective ethylene compound. MS (m/z): 291 (M$^+$)

| Elemental analysis: | C | H | N |
|---|---|---|---|
| Calcd. (C$_{20}$H$_{21}$NO) | 82.44% | 7.26% | 4.81% |
| Found | 82.50% | 7.24% | 4.85% |

Example 14

Production of 3-[1-(1-ethyl-2-methylindol-3-yl)-1-(4-chlorophenyl)ethylen-2-yl]-3-(4-diethylaminophenyl)phthalide (compound 108)

Figure 12:
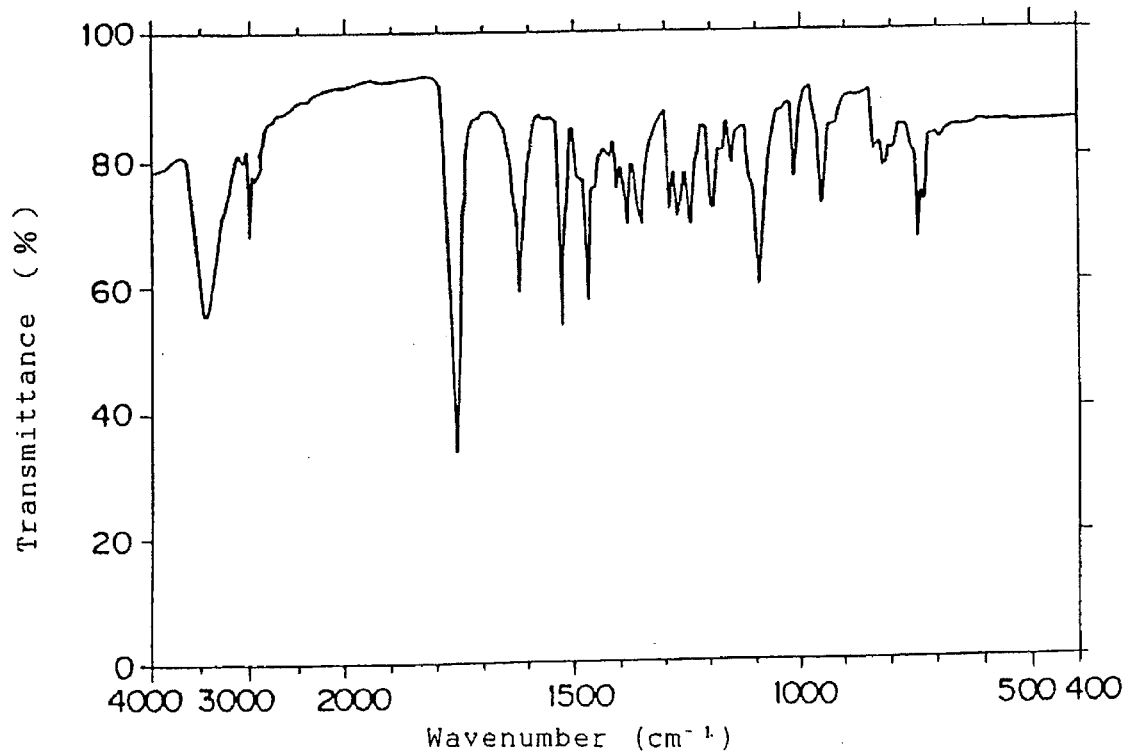
FIG. 12 is an infrared absorption spectrum of compound 108 as synthesized in Example 14.

88.7 g (0.30 mol) of 1-(1-ethyl-2-methylindol-3-yl)-1-(4-chlorophenyl)ethylene, 89.2 g (0.30 mol) of 2-(4-diethylaminobenzoyl)benzoic acid, 61.3 g (0.60 mol) of acetic anhydride and 120 mL of toluene were stirred together at 50°–55° C. for 4.0 hours. After cooling, 1000 mL of toluene and 500 g of 5% sodium hydroxide (aq.) were added. The mixture was further stirred for 1 hour and the toluene layer was then separated, washed with warm water, filtered and concentrated. The residue was subjected to column chromatography on silica gel using toluene as an eluent and the eluate was concentrated. The concentrate was stirred in 1000 mL of methanol under reflux for 1 hour. After cooling, the precipitate was collected by filtration and dried to provide 52.6 g (yield 30.5%) of white powder. m.p. 144°–146° C. This powder was verified by mass spectrometry and elemental analysis to be the title phthalide compound. Its infrared absorption spectrum is presented in FIG. 12. MS (m/z): 574 (M$^+$)

| Elemental analysis: | C | H | N |
|---|---|---|---|
| Calcd. (C$_{37}$H$_{35}$N$_2$O$_2$Cl) | 77.27% | 6.13% | 4.87% |
| Found | 77.31% | 6.08% | 4.81% |

The 1-(1-ethyl-2-methylindol-3-yl)-1-(4-chlorophenyl)ethylene used in this example was synthesized in the following manner.

79.6 g (0.50 mol) of 1-ethyl-2-methylindole, 80.4 g (0.52 mol) of 4'-chloroacetophenone, 1.0 g of p-toluenesulfonic acid monohydrate and 150 mL of toluene were stirred together at 118°–120° C. for 4 hours and after cooling, 100 g of 1% sodium hydroxide (aq.) was added. The mixture was further stirred for 10 minutes, after which the toluene layer was separated, washed with warm water, filtered and concentrated. The residue was subjected to column chromatography on silica gel using hexane as an eluent to provide 121.3 g (yield 82%) of light-red liquid. This liquid was verified by the following analyses to be the objective ethylene compound. MS (m/z): 295 (M$^+$)

| Elemental analysis: | C | H | N |
|---|---|---|---|
| Calcd. (C$_{19}$H$_{18}$NCl) | 77.15% | 6.13% | 4.74% |
| Found | 77.20% | 6.19% | 4.70% |

Example 15

Production of 3-[1-(1-ethyl-2-methylindol-3-yl)-1-(4-methylphenyl)ethylen-2-yl]-3-(4-diethylaminophenyl)benzo(f)phthalide (compound 144)

Figure 13:
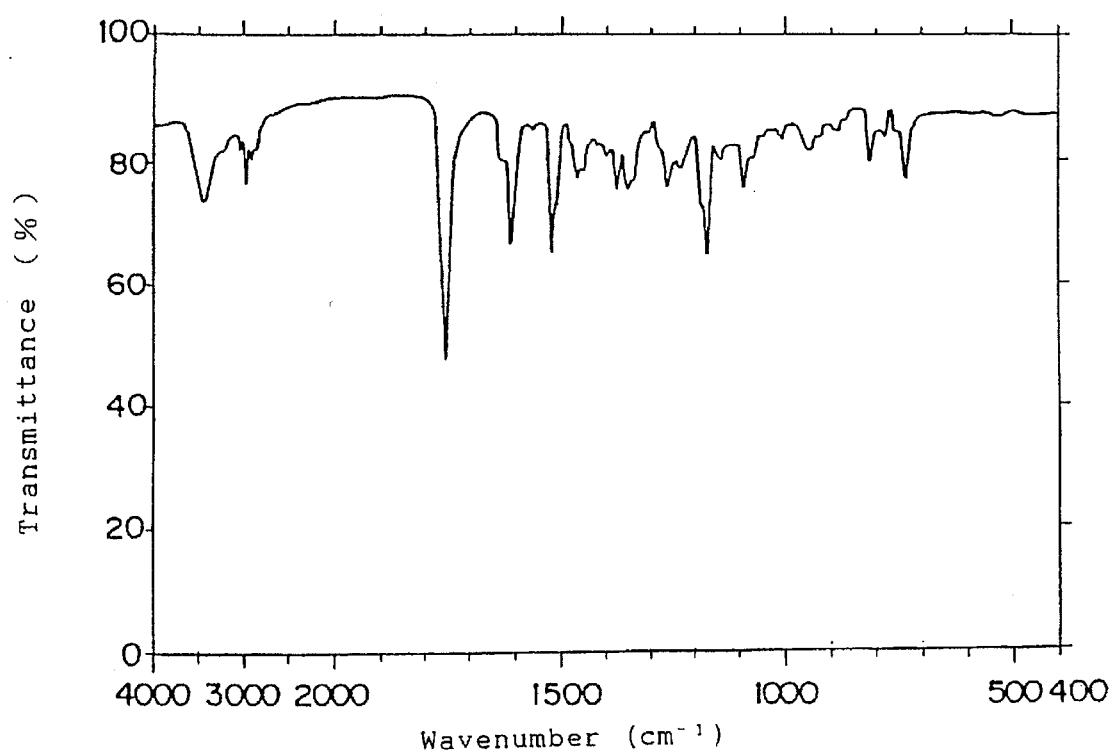
FIG. 13 is an infrared absorption spectrum of compound 144 as synthesized in Example 15.

41.3 g (0.15 mol) of 1-(1-ethyl-2-methylindol-3-yl)-1-(4-methylphenyl)ethylene, 52.1 g (0.15 mol) of 2-carboxy-3-(4-diethylaminobenzoyl)naphthalene, 40.8 g (0.40 mol) of acetic anhydride and 10 mL of toluene were stirred together at 45°–50° C. for 4.0 hours. After cooling, 150 mL of toluene and 150 mL of water were added. The mixture was further stirred for 1 hour and the toluene layer was then separated, washed with warm water, filtered and concentrated. The residue was subjected to column chromatography on silica gel using toluene as an eluent to obtain the objective fraction. This fraction was further purified by recrystallization from methanol to provide 19.5 g (yield 21.5%) of white powder. m.p. 182°–184° C. This powder was verified by mass spectrometry and elemental analysis to be the title phthalide compound. Its infrared absorption spectrum is presented in FIG. 13. MS (m/z): 604 (M$^+$)

| Elemental analysis: | C | H | N |
|---|---|---|---|
| Calcd. (C$_{42}$H$_{40}$N$_2$O$_2$) | 83.41% | 6.67% | 4.63% |
| Found | 83.29% | 6.70% | 4.60% |

The 2-carboxy-3-(4-diethylaminobenzoyl)naphthalene used in this example was synthesized in the following manner.

To a mixture of 207 g of chlorobenzene and 93.5 g of aluminum chloride was added 104.3 g (0.70 mol) of diethylaniline dropwise under ice-cooling and stirring. Then, 69.3 g (0.35 mol) of 2,3-naphthalenedicarboxylic anhydride was added and the mixture was stirred at 45°–50° C. for 4 hours. The reaction mixture was poured into 1 L of water and the chlorobenzene was distilled off. The precipitate was separated, diluted with 100 mL of toluene and extracted with 500 g of 15% aqueous sodium hydroxide solution. The extract was precipitated from 5% hydrochloric acid and the precipitate was collected and washed with warm water. It was then recrystallized from toluene-methanol to provide 85.0 g (yield 69.9%) of yellow-greenish white powder. This powder was verified by the following analyses to be the objective benzoic acid derivative. MS (m/z): 347 (M$^+$)

| Elemental analysis: | C | H | N |
|---|---|---|---|
| Calcd. (C$_{22}$H$_{21}$NO$_3$) | 76.06% | 6.09% | 4.03% |
| Found | 76.00% | 6.06% | 4.10% |

Example 16

Production of 3-[1-(1-ethyl-2-methylindol-3-yl)-1-(4-methylphenyl)ethylen-2-yl]-3-(4-diethylaminophenyl)-4,5,6,7-tetrachlorophthalide (compound 155)

Figure 14:
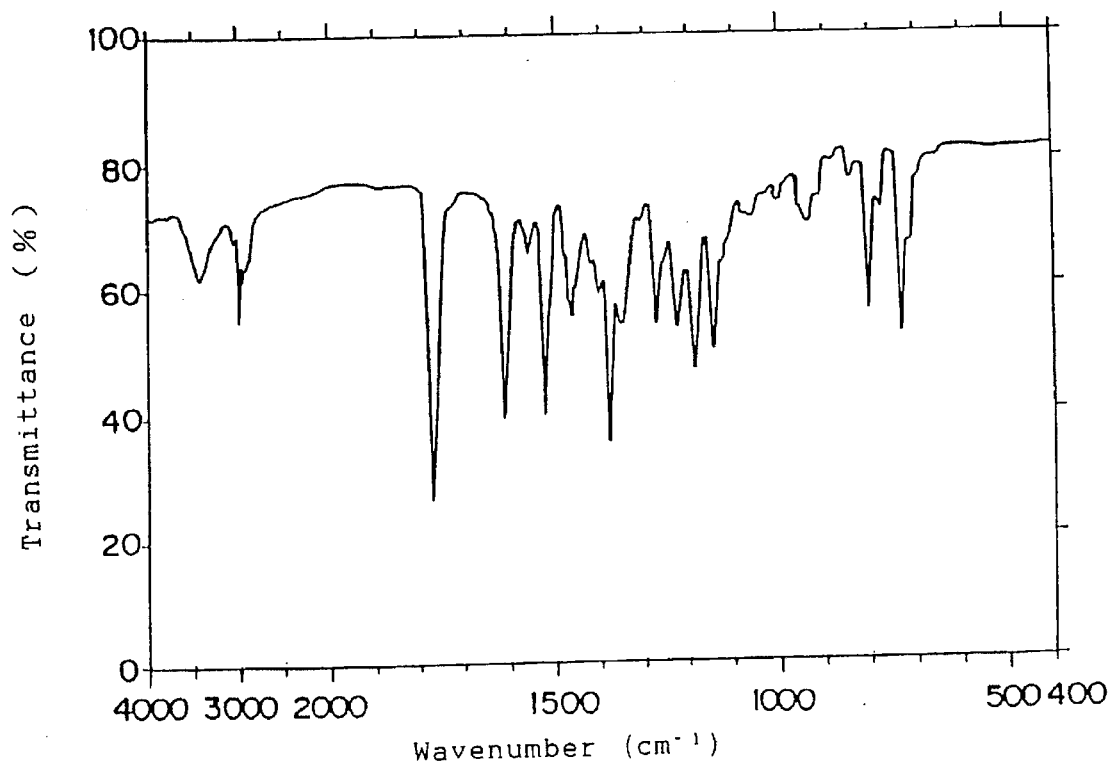
FIG. 14 is an infrared absorption spectrum of compound 155 as synthesized in Example 16.

41.3 g (0.15 mol) of 1-(1-ethyl-2-methylindol-3-yl)-1-(4-methylphenyl)ethylene, 65.3 g (0.15 mol) of 2-(4-diethylaminobenzoyl)-3,4,5,6-tetrachlorobenzoic acid, 40.8 g (0.40 mol) of acetic anhydride and 10 mL of toluene were stirred together at 45°–50° C. for 4.0 hours. After cooling, 150 mL of toluene and 150 mL of water were added. The mixture was further stirred for 1 hour and the toluene layer was then separated, washed with warm water, filtered and concentrated. The residue was subjected to column chromatography on silica gel using toluene as an eluent to obtain the objective fraction. This fraction was further purified by recrystallization from methanol to provide 31.4 g (yield 30.2%) of light yellow white powder. m.p. 175°–177° C. This powder was verified by mass spectrometry and elemental analysis to be the title phthalide compound. Its infrared absorption spectrum is presented in FIG. 14. MS (m/z): 692 (M$^+$)

| Elemental analysis: | C | H | N |
|---|---|---|---|
| Calcd. (C$_{38}$H$_{34}$N$_2$O$_2$Cl$_4$) | 65.91% | 4.95% | 4.05% |
| Found | 65.95% | 4.98% | 4.10% |

The 2-(4-diethylaminobenzoyl)-3,4,5,6-tetrachlorobenzoic acid used in this example was synthesized in the following manner.

To a mixture of 944 g of chlorobenzene and 227 g of aluminum chloride was added 253.3 g (1.70 mol) of diethylaniline dropwise under ice-cooling and stirring. Then, 243.1 g (0.85 mol) of 3,4,5,6-tetrachlorophthalic anhydride was added and the mixture was stirred at 35°–40° C. for 2 hours. The reaction mixture was then poured into 1 L of water and the chlorobenzene was distilled off. The precipitate was collected, washed with warm water, dried and recrystallized from toluene-methaol to provide 330.2 g (yield 89%) of yellowish white powder. This powder was verified by the following analyses to be the objective benzoic acid derivative. MS (m/z): 435 (M$^+$)

| Elemental analysis: | C | H | N |
|---|---|---|---|
| Calcd. (C$_{18}$H$_{15}$NO$_3$Cl$_4$) | 49.69% | 3.47% | 3.22% |
| Found | 49.77% | 3.53% | 3.29% |

Comparison Example of Synthesis-1

Production of 3-[1-(1-ethyl-2-methylindol-3-yl)-1-(4-dimethylaminophenyl)ethylen-2-yl]-3-(4-diethylaminophenyl)phthalide (compound A)

10.65 g (0.035 mol) of 1-(1-ethyl-2-methylindol-3-yl)-1-(4-dimethylaminophenyl)ethylene, 10.41 g (0.035 mol) of 2-(4-diethylaminobenzoyl)benzoic acid, 7.1 g (0.07 mol) of acetic anhydride and 15 mL of toluene were stirred together at 55°–60° C. for 4.5 hours. After cooling, 100 mL of toluene and 50 g of 10% sodium hydroxide (aq.) were added. The mixture was stirred for 1 hour and the toluene layer was then separated, washed with warm water, filtered and concentrated. The residue was subjected to column chromatography on silica gel using toluene as an eluent to isolate the objective compound. This product was further stirred in 50 mL of hexane under reflux for 1 hour. After cooling, the precipitate was collected by filtration and dried to provide 9.3 g (yield 45.5%) of beige powder. m.p. 76°–78° C. This powder was further purified by recrystallization from 150 mL of IPA to provide 7.6 g (yield 37.2%) of white powder. m.p. 149°–152° C. This powder was verified by mass spectrometry and elemental analysis to be the title phthalide compound. MS (m/z): 583 (M$^+$)

| Elemental analysis: | C | H | N |
|---|---|---|---|
| Calcd. (C$_{39}$H$_{41}$N$_3$O$_2$) | 80.23% | 7.09% | 7.12% |
| Found | 80.25% | 7.05% | 7.13% |

The 1-(1-ethyl-2-methylindol-3-yl)-1-(4-dimethylaminophenyl)ethylene used in this comparison example of synthesis was synthesized in the following manner.

22.1 g (0.139 mol) of 1-ethyl-2-methylindole, 25.0 g (0.153 mol) of 4'-dimethylaminoacetophenone, 1.0 g of p-toluenesulfonic acid monohydrate and 75 mL of toluene were stirred together at 118°–122° C. for 6.5 hours and after cooling, 100 mL of toluene and 50 g of 1% sodium hydroxide (aq.) was added. The mixture was further stirred for 10 minutes, after which the toluene layer was separated, washed with warm water, filtered and concentrated. The residue was subjected to column chromatography on silica gel using toluene as an eluent to provide 18.3 g (yield 43.2%) of light-red liquid. This liquid was verified by the following analyses to be the objective ethylene compound. MS (m/z): 304 (M$^+$)

| Elemental analysis: | C | H | N |
|---|---|---|---|
| Calcd. (C$_{21}$H$_{24}$N$_2$) | 82.85% | 7.95% | 9.20% |
| Found | 82.80% | 7.91% | 9.16% |

Comparison Example of Synthesis-2

Production of 3-[1-(1-ethyl-2-methylindol-3-yl)-1-(4-dimethylaminophenyl)ethylen-2-yl]-3-(2-n-butoxy-4-diethylaminophenyl)phthalide (compound B)

23.7 g (0.078 mol) of 1-(1-ethyl-2-methylindol-3-yl)-1-(4-dimethylaminophenyl)ethylene, 45.0 g (0.122 mol) of 2-(2-n-butoxy-4-diethylaminobenzoyl)benzoic acid, 24.9 g (0.244 mol) of acetic anhydride and 40 mL of toluene were stirred together at 50°–53° C. for 1.5 hours. After cooling, 100 g of 10% sodium hydroxide (aq.) and 100 mL of toluene were added. The mixture was further stirred for 1 hour and the toluene layer was then separated, washed with warm water, filtered and concentrated. The residue was subjected to column chromatography on silica gel using toluene-ethyl acetate as an eluent and the eluate was concentrated. The residue was stirred in 50 mL of methanol under reflux for 1 hour. After cooling, the precipitate was collected by filtration and dried to provide 15.6 g (yield 30.5%) of greenish white powder. m.p. 148°–151° C. This powder was verified by mass spectrometry and elemental analysis to be the title phthalide compound. MS (m/z): 655 (M$^+$)

| Elemental analysis: | C | H | N |
|---|---|---|---|
| Calcd. ($C_{43}H_{49}N_3O_3$) | 78.74% | 7.53% | 6.41% |
| Found | 78.70% | 7.48% | 6.43% |

Example 17

Production of a near infrared absorber 0.15 g of 3-[1-(1-ethyl-2-methylindol-3-yl)-1-(4-methylphenyl)ethylen-2-yl]-3-(4-diethylaminophenyl)phthalide (compound 1) and 0.30 g of benzyl p-hydroxybenzoate were heated together to provide a melt.

The melt was coated thinly on a glass sheet and cooled. The absorption characteristics of the near infrared absorbing device thus fabricated were determined on Spectrophotometer UV365 (Shimadzu Corporation). This device was found to have an absorption maximum at 720 nm. The region corresponding to not less than 80% absorbance relative to this absorption maximum was 700 nm–750 nm and the region corresponding to not less than 50% absorbance relative to said absorption maximum was 670 nm–770nm.

Figure 15:
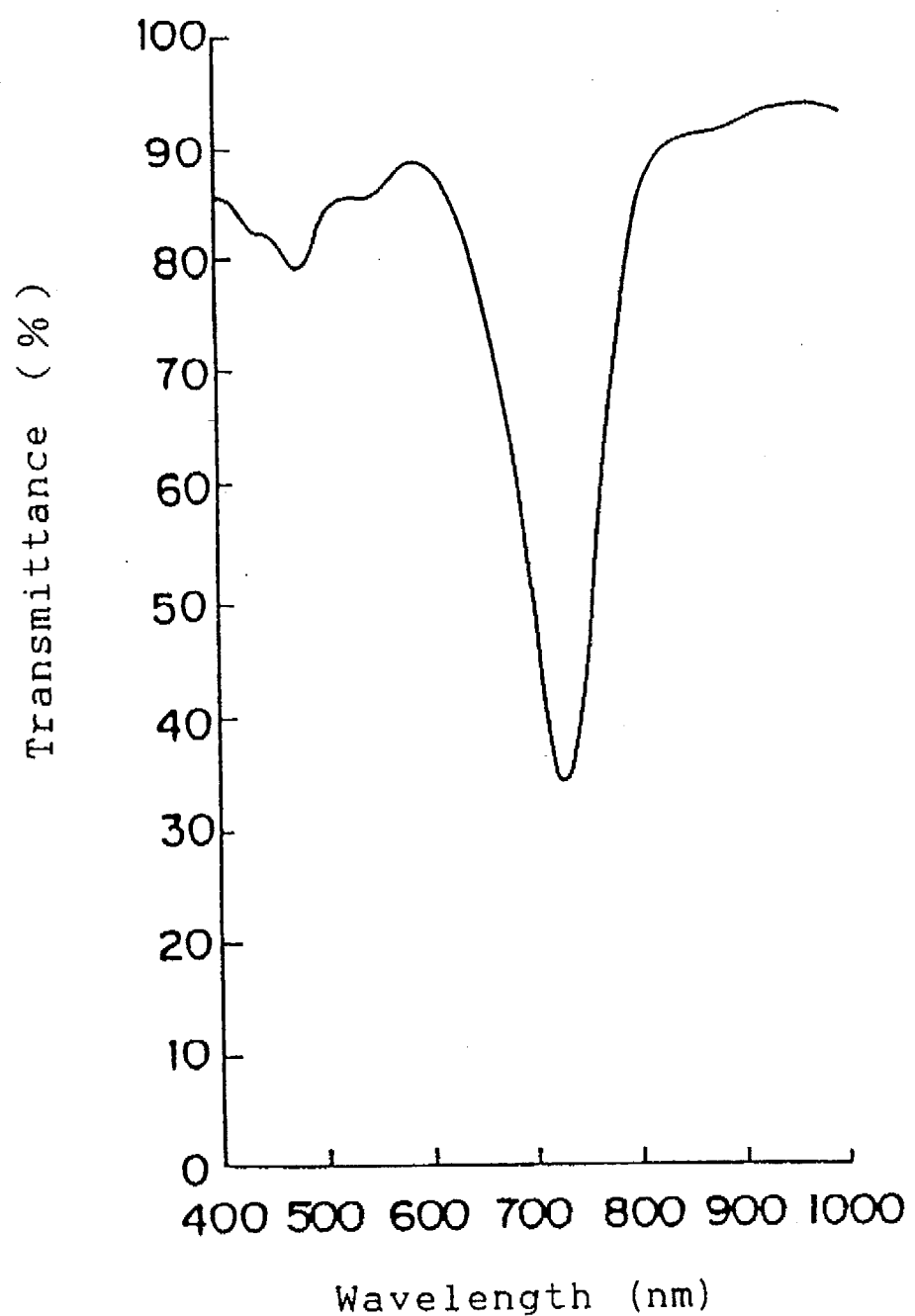
FIG. 15 is an absorption spectrum of the glass sheet coated with the near infrared absorber produced from compound 1 and PHB as manufactured in Example 17.

The absorption spectrum of a glass sheet coated with the near infrared absorber of this invention [the reaction product of Compound 1 and benzyl p-hydroxybenzoate] is presented in FIG. 15.

Comparison Example 1

Production of a near infrared absorber

The procedure of Example 17 was repeated except that compound A as synthesized in Comparison Example of Synthesis-1 was used in lieu of 3-[1-(1-ethyl-2-methylindol-3-yl)-1-(4-methylphenyl)ethylen-2-yl]-3-(4diethylaminophenyl)phthalide (compound 1). The resulting near infrared absorber was green-blue with a absorption maximum at 745 nm and a characteristic absorption at 620 nm. The region corresponding to not less than 80% absorbance relative to the above absorption maximum was 690 nm–780 nm and the region corresponding to not less than 50% absorbance relative to said absorption maximum was 585 nm–800 nm.

Figure 16:
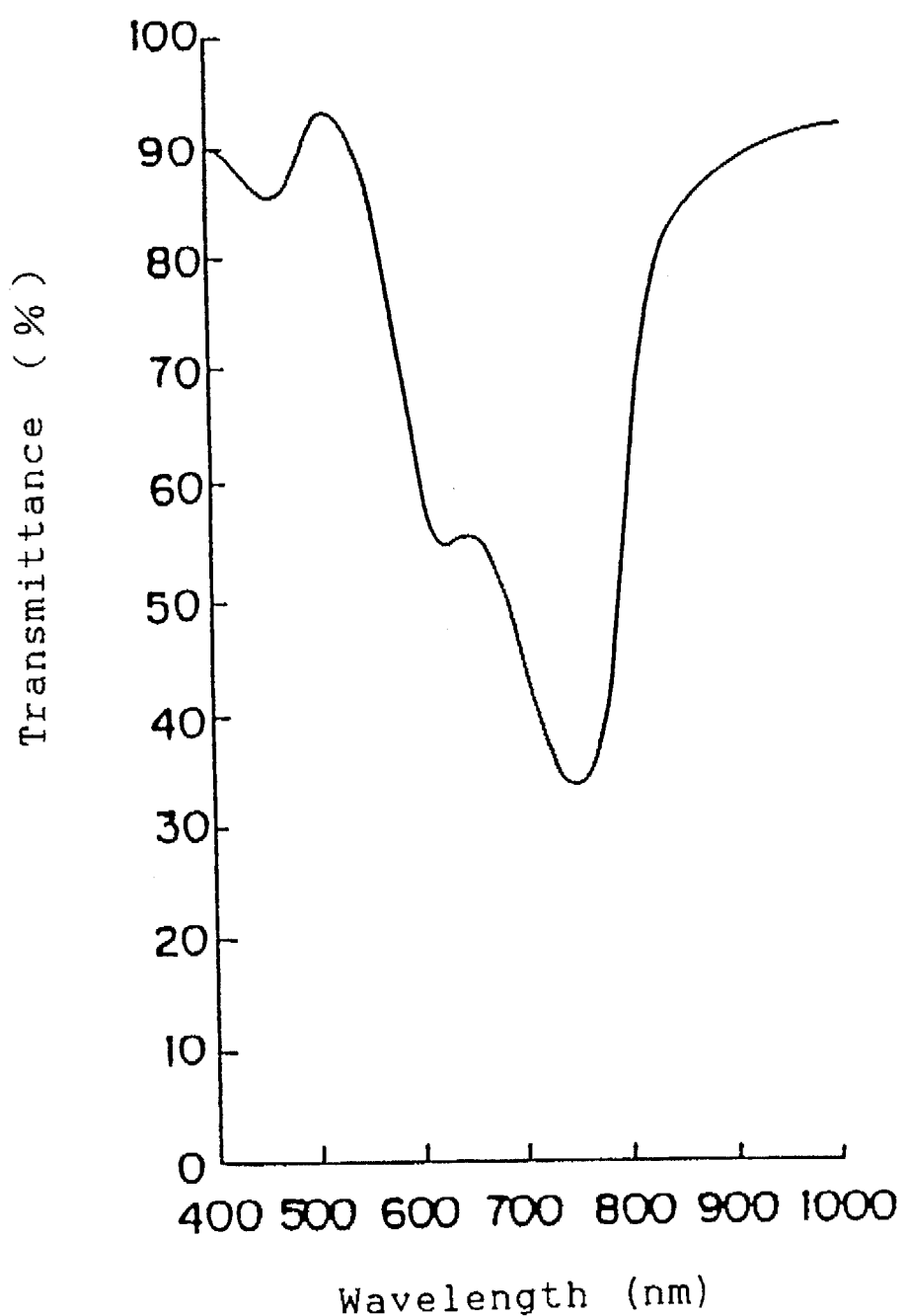
FIG. 16 is an absorption spectrum of the glass sheet coated with the near infrared absorber produced from compound A and PHB as manufactured in Comparison Example 1.

The absorption spectrum of a glass sheet coated with the reaction product of compound A (Comparison Example of Synthesis-1) and benzyl p-hydroxybenzoate is presented in FIG. 16.

Example 18

Production of a near infrared absorber

In 5 ml of THF were dissolved 15 mg of 3-[1-(1-ethyl-2-methylindol-3-yl)-1-(4-methylphenyl)ethylen-2-yl]-3-(4-diethylaminophenyl)phthalide (compound 1) and 30 mg of bisphenol A to prepare a solution.

This solution was coated on a sheet of wood-free paper and allowed to dry. The paper carrying the near infrared absorber was as white as the substrate paper.

The absorption characteristics of the above paper were determined in terms of reflectance using Spectrophotometer UV365 (Shimadzu Corporation). The absorbance is expressed by the following equation.

Absorbance (%)=100−reflectance (%)

(The term 'absorbance' as used herein means the value calculated by means of the above equation).

The above paper was found to have an absorption maximum at 725 nm and the wavelength region corresponding to not less than 80% absorbance relative to the above absorption maximum was 675 nm–770 nm.

Figure 17:
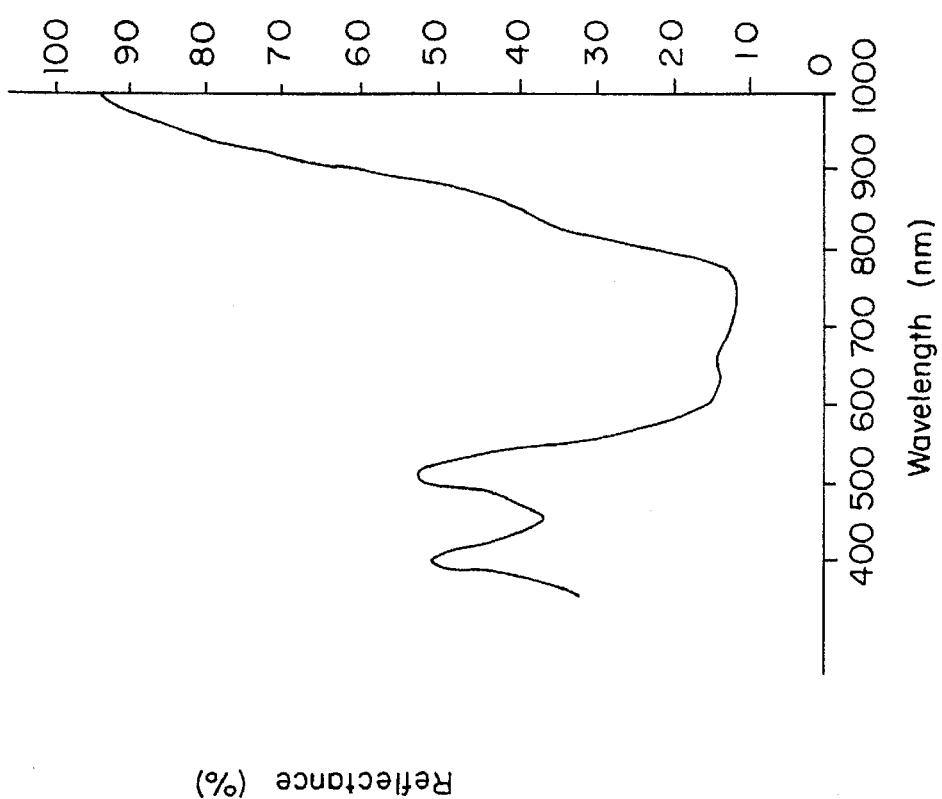
FIG. 17 is a reflection spectrum of the sheet of paper coated with the near infrared absorber produced from compound 1 and bisphenol A as manufactured in Example 18.

The reflectance spectrum of the paper coated with the near infrared absorber of this invention (the product of reaction between compound 1 and bisphenol A) is presented in FIG. 17.

Comparison Example 2

Production of a near infrared absorber

The procedure of Example 18 was repeated except that compound A as synthesized in Comparison Example of Synthesis-1 was used in lieu of 3-[1-(1-ethyl-2-methylindol-3-yl)-1-(4-methylphenyl)ethylen-2-yl]-3-(4-diethylaminophenyl)phthalide (compound 1). The coated paper was distinct green-blue. This paper had an absorption maximum at 735 nm and the wavelength region corresponding to not less than 80% absorbance relative to said absorption maximum was 560 nm–815 nm.

Figure 18:
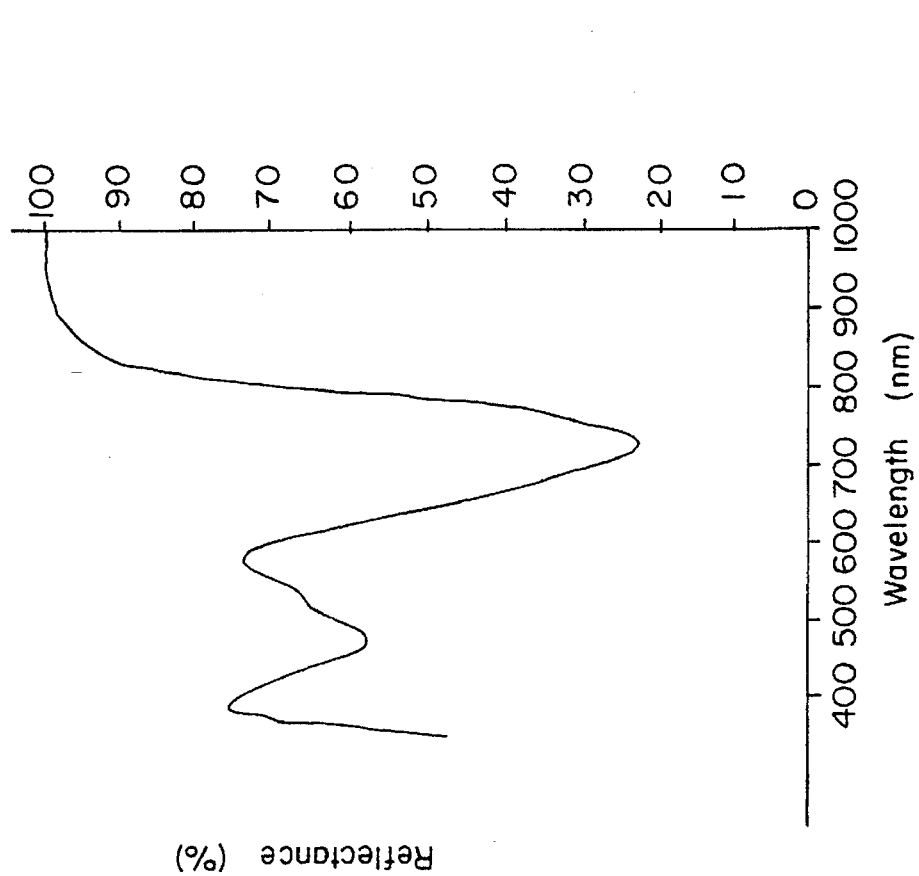
FIG. 18 is a reflection spectrum of the sheet of paper coated with the near infrared absorber produced from compound A and bisphenol A as manufactured in Comparison Example 2.
Figures 19, 20:
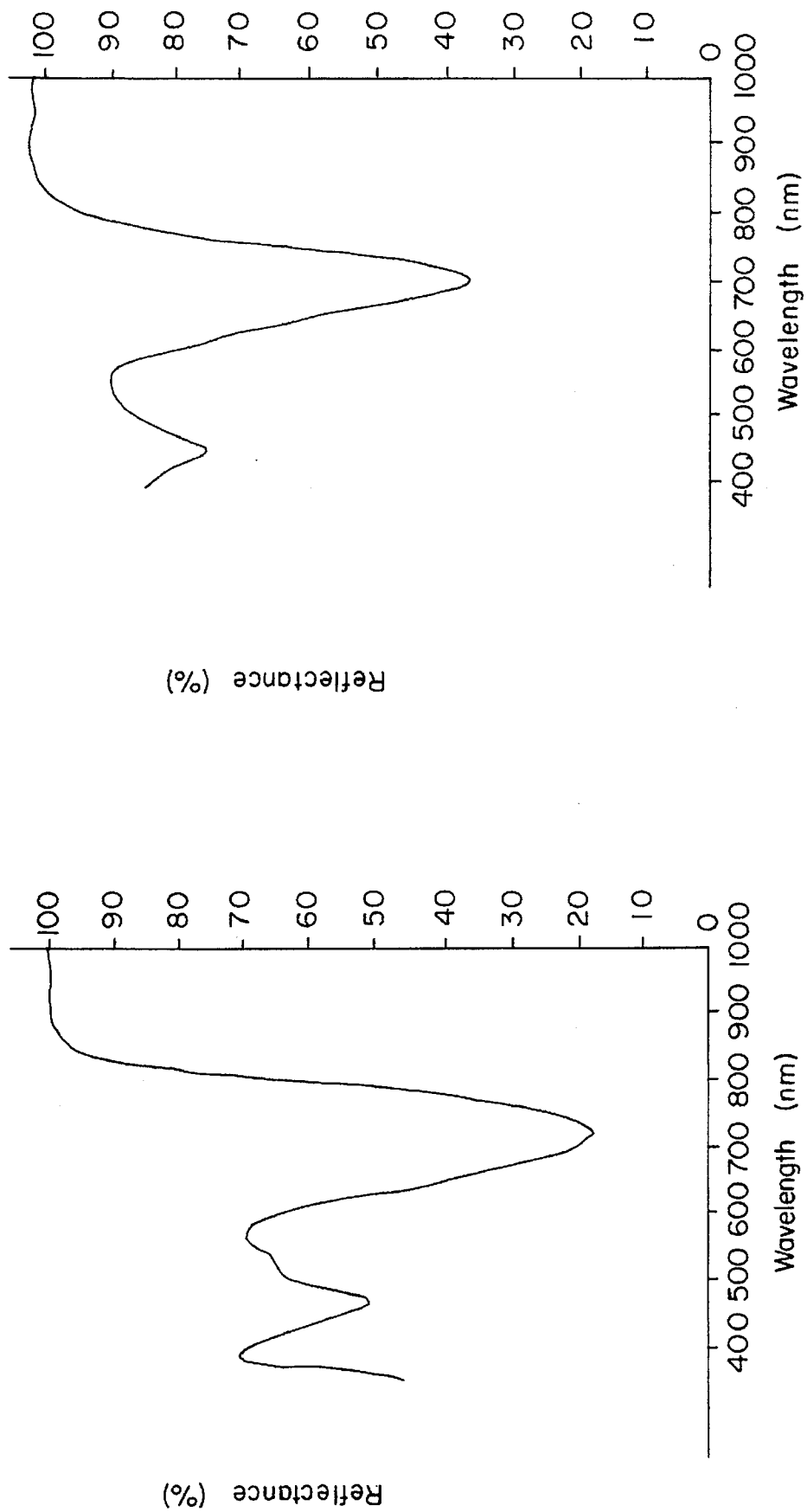
FIG. 19 is a reflection spectrum of the sheet of paper coated with the near infrared absorber produced from compound 13 and TG-SA as manufactured in Example 28.
FIG. 20 is a reflection spectrum of the sheet of paper coated with the near infrared absorber produced from compound 23 and D-8 as manufactured in Example 34.
Figure 21:
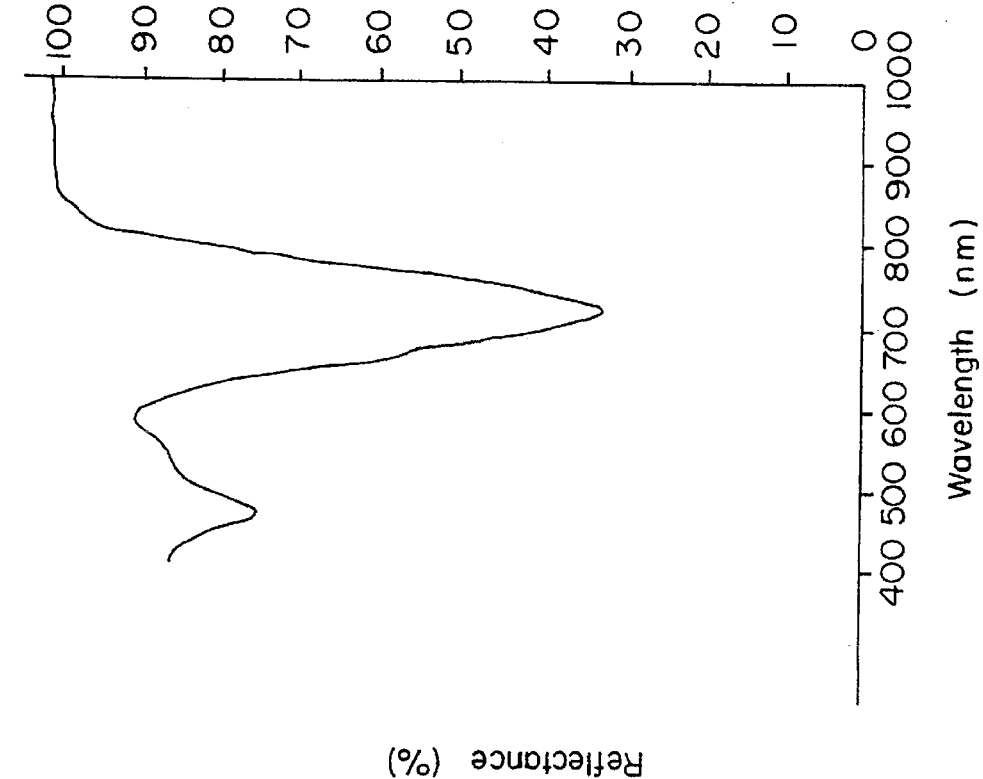
FIG. 21 is a reflection spectrum of the sheet of paper coated with the near infrared absorber produced from compound 41 and bisphenol S as manufactured in Example 45.
Figure 22:
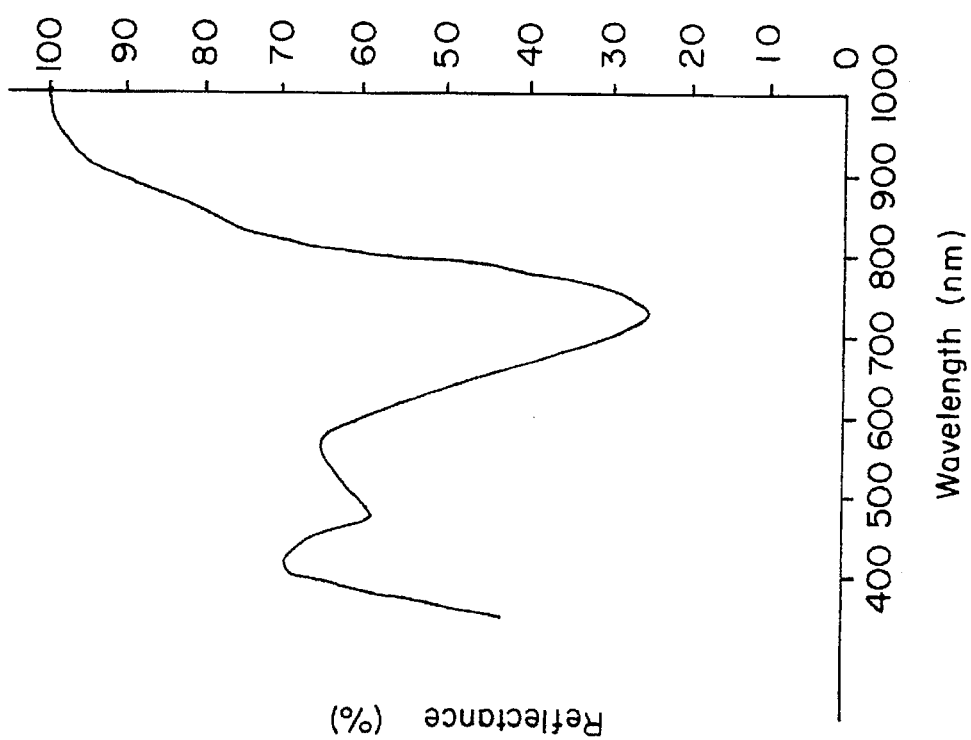
FIG. 22 is a reflection spectrum of the sheet of paper coated with the near infrared absorber produced from compound 57 and PHB as manufactured in Example 51.
Figure 23:
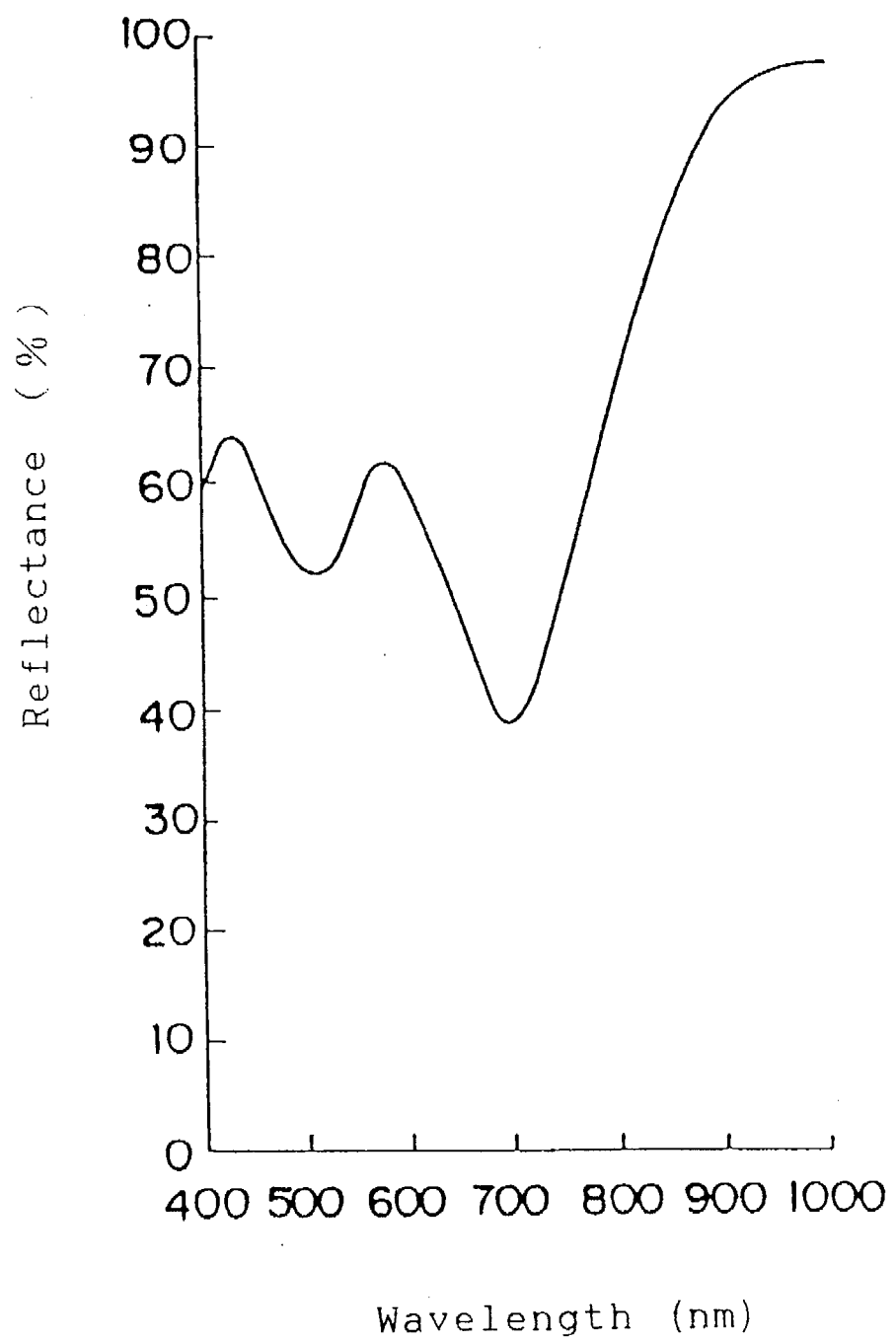
FIG. 23 is a reflection spectrum of the sheet of paper coated with the near infrared absorber produced from compound 87 and bisphenol A as manufactured in Example 61.
Figure 24:
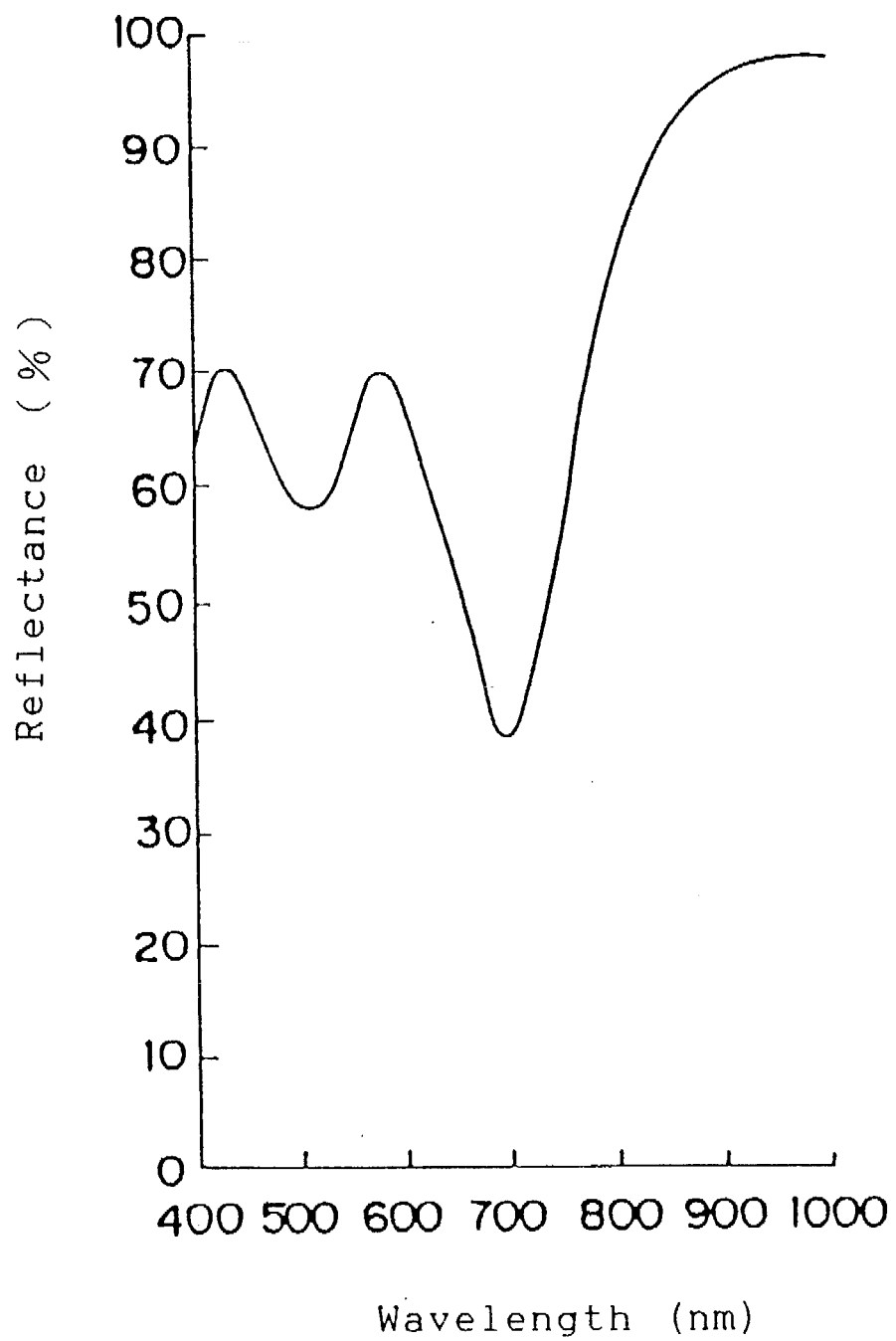
FIG. 24 is a reflection spectrum of the sheet of paper coated with the near infrared absorber produced from compound 89 and PHB as manufactured in Example 66.
Figure 25:
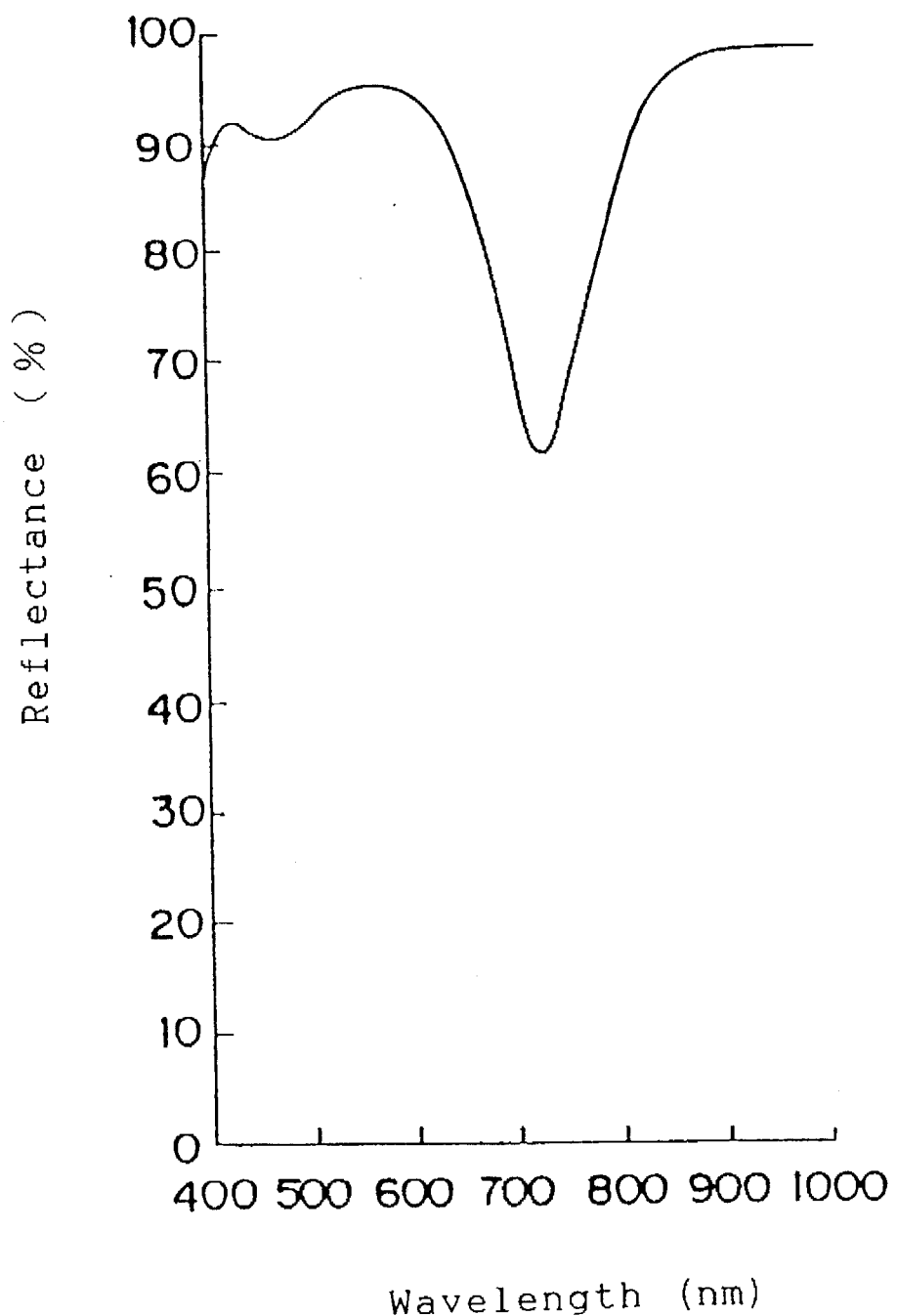
FIG. 25 is a reflection spectrum of the sheet of paper coated with the near infrared absorber produced from compound 91 and bisphenol A as manufactured in Example 67.
Figure 27:
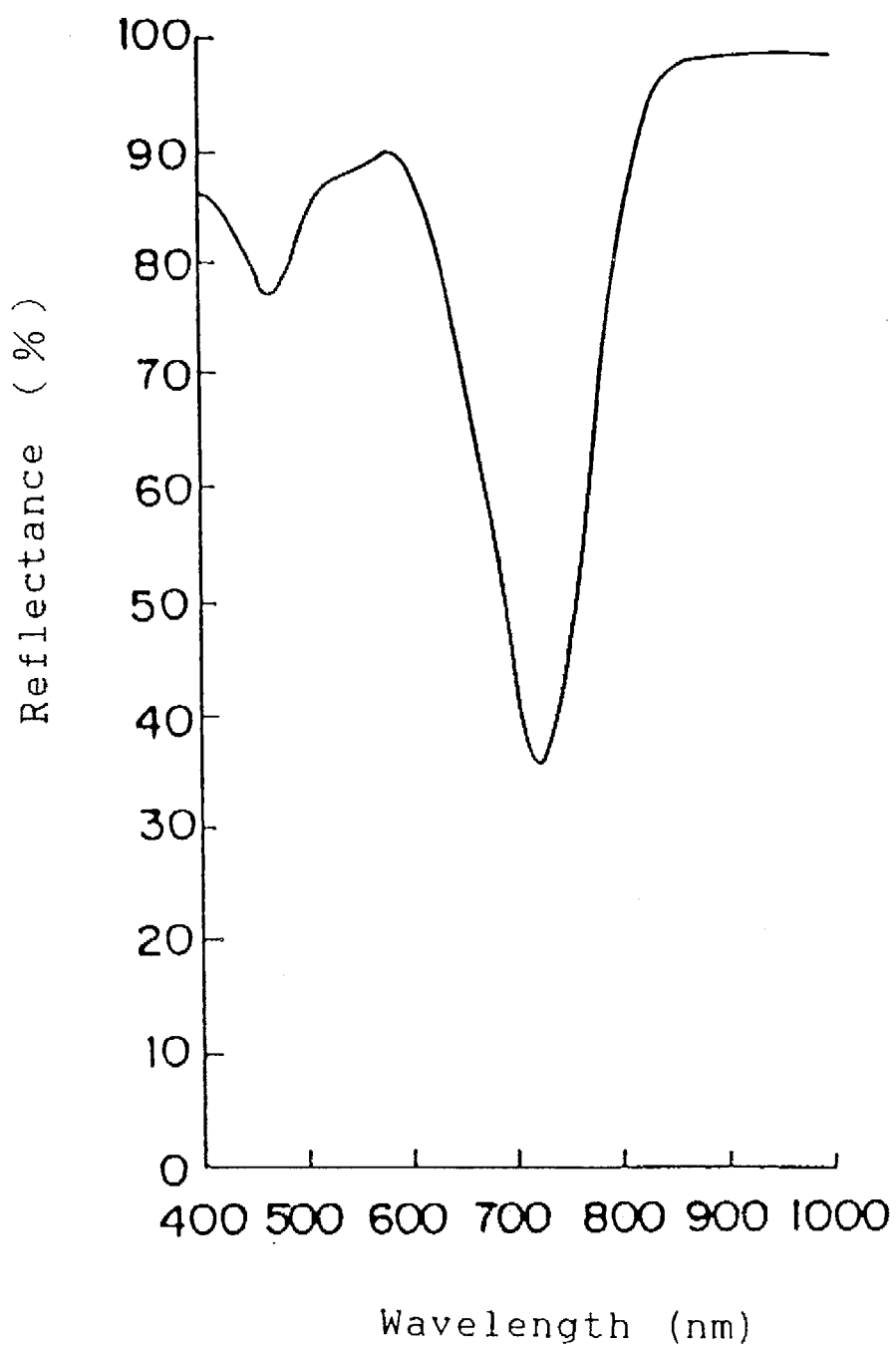
FIG. 27 is a reflection spectrum of the sheet of paper coated with the near infrared absorber produced from compound 97 and PHB as manufactured in Example 75.
Figure 28:
FIG. 28 is a reflection spectrum of the sheet of paper coated with the near infrared absorber produced from compound 98 and bisphenol A as manufactured in Example 76.
Figure 29:
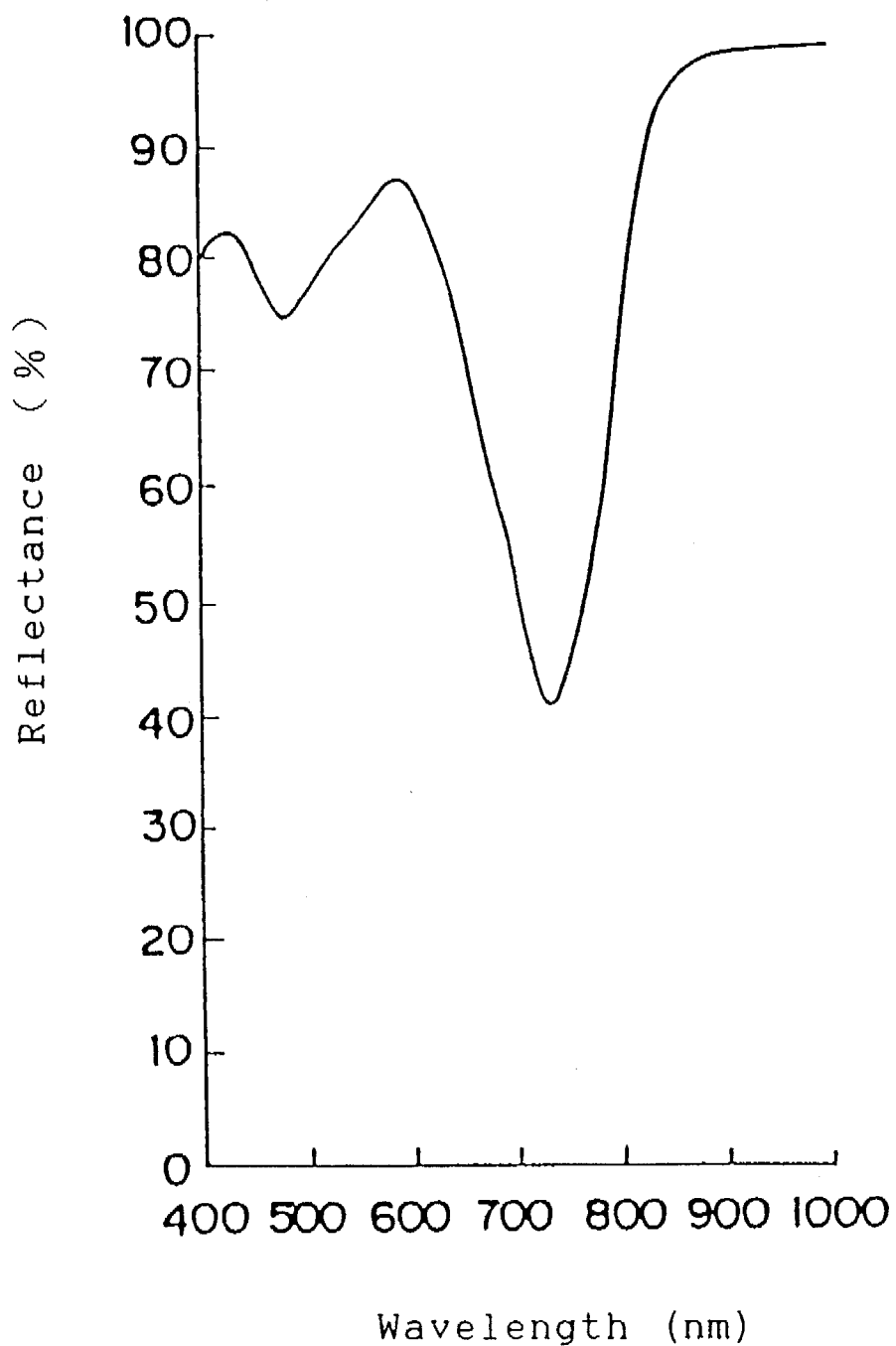
FIG. 29 is a reflection spectrum of the sheet of paper coated with the near infrared absorber produced from compound 108 and bisphenol A as manufactured in Example 79.
Figure 30:
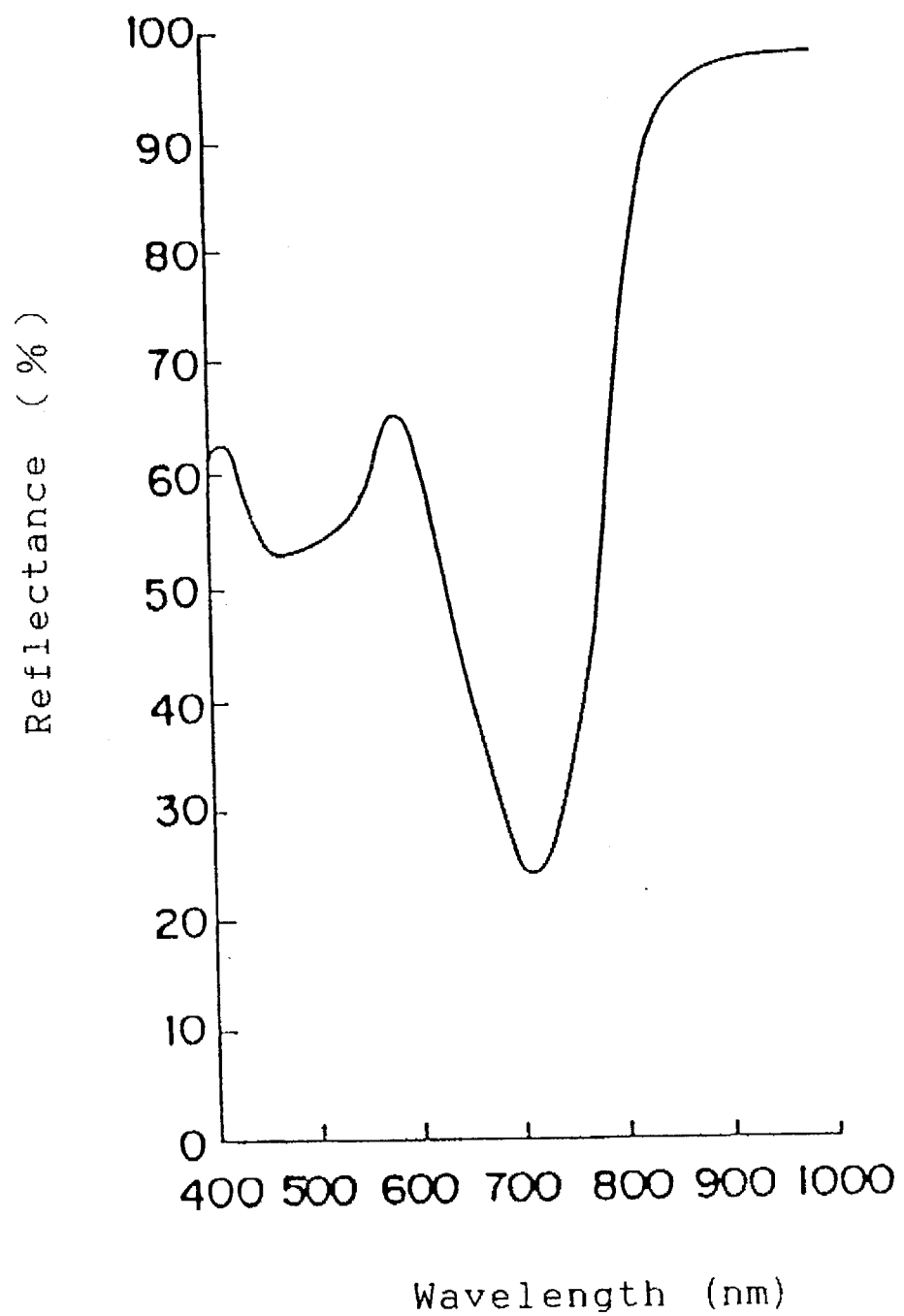
FIG. 30 is a reflection spectrum of the sheet of paper coated with the near infrared absorber produced from compound 144 and D-8 as manufactured in Example 83.
Figure 31:
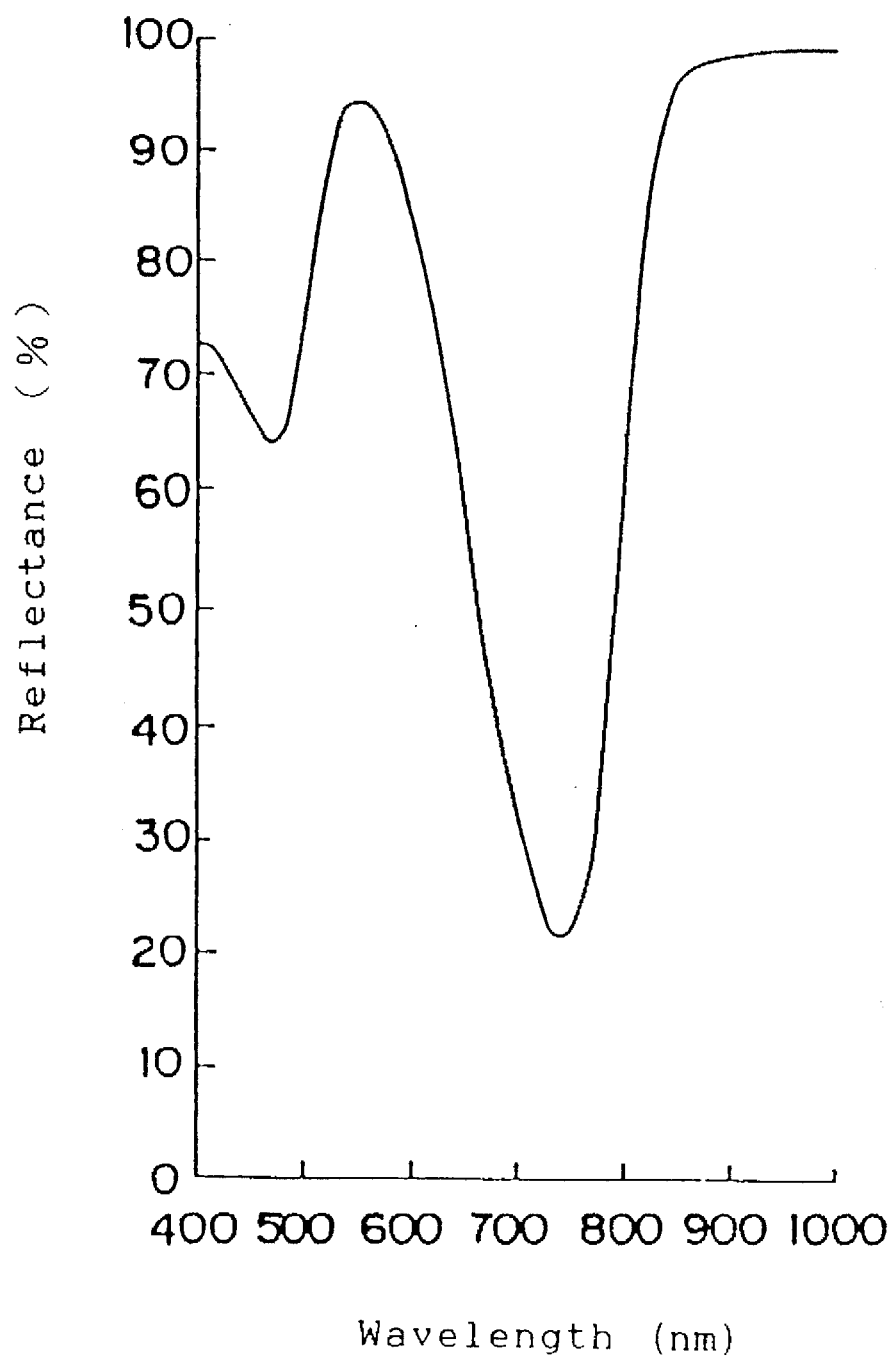
FIG. 31 is a reflection spectrum of the sheet of paper coated with the near infrared absorber produced from compound 155 and D-8 as manufactured in Example 86.

The reflectance spectrum of the paper coated with the product of reaction between compound A (Comparison Example of Synthesis-1) and bisphenol A is presented in FIG. 18.

Examples 19–14

Production of near infrared absorbers

The procedure of Example 18 was repeated except that the electron-accepting compounds listed below in Table 2 were respectively used in lieu of bisphenol A. The results are shown in Table 2. The sheets of paper coated with the respective near infrared absorbers produced above absorbed strongly the near infrared region as did the coated paper fabricated in Example 18 but absorbed little the visible region so that the papers were either white or of pale color.

Comparison Examples 3–9

Production of near infrared absorbers

The procedure of Example 18 was repeated except that compound A was used in lieu of 3-[1-(1-ethyl-2-methylindol-3-yl)-1-(4-methylphenyl)ethylen-2-yl]-3-(4-diethylaminophenyl)phthalide (compound 1) and that the electron accepting compounds shown below in Table 2 were respectively used. The results are shown in Table 2.

TABLE 2

| | | Absorption Characteristics | | |
|---|---|---|---|---|
| | Electron-accepting compound | Maximum absorption wavelength (nm) | The region of ≧80% absorbance relative to maximum absorption (nm) | Color, by visual obervation |
| Example 19 | D-8 | 715 | 685–750 | White |
| Example 20 | AP-5 | 720 | 690–760 | White |
| Example 21 | TG-SA | 725 | 650–740 | Pale grayish white |
| Example 22 | PHB | 725 | 690–755 | White |
| Example 23 | Tamanol P | 720 | 695–745 | White |
| Example 24 | Hitanol 1501 | 720 | 685–755 | White |
| Comparison Example 3 | D-8 | 740 | 565–805 | Green-blue |
| Comparison Example 4 | AP-5 | 740 | 570–805 | Green-blue |
| Comparison | TG-SA | 745 | 565–815 | Green-blue |

TABLE 2-continued

| | | Absorption Characteristics | | |
|---|---|---|---|---|
| | Electron-accepting compound | Maximum absorption wavelength (nm) | The region of ≧80% absorbance relative to maximum absorption (nm) | Color, by visual obervation |
| Example 5 Comparison Example 6 | PHB | 740 | 570–805 | Light green-blue |
| Comparison Example 7 | Bisphenol S | 745 | 555–815 | Green-blue |
| Comparison Example 8 | Tamanol P | 740 | 595–780 | Green-blue |
| Comparison Example 9 | Hariester 510 | 740 | 620–775 | Light Blue |

In the table, D-8 stands for 4-hydroxy-4'-isopropoxy-diphenyl sulfone, AP-5 for 2,2-bis(p-hydroxyphenyl)-4-methyl-pentane, TG-SA for 3,3'-diallyl-4,4'-dihydroxydiphenyl sulfone, and PHB for benzyl p-hydroxybenzoate.

Examples 25–87

Production of near infrared absorbers

The procedure of Example 18 was repeated except that the phthalide compounds listed in Table 3 were respectively used in lieu of 3-[1-(1-ethyl-2-methylindol-3-yl)-1-(4-methylphenyl)ethylen-2-yl]-3-(4-diethylaminophenyl)phthalide (compound 1) and that the electron accepting compounds shown in Table 3 were respectively used. The results are shown in Table 3.

The reflectance spectra of the coated papers according to Examples 28, 34, 45, 51, 61, 66, 67, 71, 75, 76, 79, 83 and 86 are presented in FIG. 19, 20, 21, 22, 23, 24, 25, 26, 27, 28, 29, 30 and 31, respectively.

Comparison Examples 10–12

The procedure of Example 18 was repeated except that compound B prepared in Comparison Example of Synthesis-2 was used in lieu of 3-[1-(1-ethyl-2-methylindol-3-yl)-1-(4-methylphenyl)ethylen-2-yl]-3-(4-diethylaminophenyl)phthalide (compound 1) and that the electron accepting compounds shown below in Table 3 were respectively used. The results are shown in Table 3.

TABLE 3

| | | | Absorption characteristics | | |
|---|---|---|---|---|---|
| | Phthalide Compound No. | Electron-accepting compound | Maximum absorption wavelength (nm) | The region of ≧80% absorbance relative to maximum absorption (nm) | Color, by visual observation |
| Example 25 | Compound 13 | Bisphenol A | 725 | 690–760 | White |
| Example 26 | Compound 13 | D-8 | 720 | 695–745 | White |
| Example 27 | Compound 13 | AP-5 | 725 | 695–750 | White |
| Example 28 | Compound 13 | TG-SA | 720 | 660–770 | Pale greenish white |
| Example 29 | Compound 13 | PHB | 720 | 700–745 | White |
| Example 30 | Compound 13 | Bisphenol S | 725 | 650–780 | Pale greenish white |
| Example 31 | Compound 13 | Tamanol P | 720 | 695–735 | White |
| Example 32 | Compound 13 | Hitanol 1501 | 720 | 700–740 | White |
| Example 33 | Compound 23 | Bisphenol A | 730 | 685–775 | Pale greenish white |
| Example 34 | Compound 23 | D-8 | 720 | 685–755 | White |
| Example 35 | Compound 23 | AP-5 | 725 | 685–765 | White |
| Example 36 | Compound 23 | TG-SA | 725 | 650–750 | Pale green |
| Example 37 | Compound 23 | PHB | 720 | 680–765 | White |
| Example 38 | Compound 23 | Tamanol P | 720 | 700–740 | White |
| Example 39 | Compound 23 | Hitanol 1501 | 720 | 695–735 | White |
| Example 40 | Compound 41 | Bisphenol A | 725 | 700–755 | White |
| Example 41 | Compound 41 | D-8 | 725 | 705–750 | White |
| Example 42 | Compound 41 | AP-5 | 725 | 705–750 | White |
| Example 43 | Compound 41 | TG-SA | 725 | 685–755 | Pale greenish white |
| Example 44 | Compound 41 | PHB | 725 | 680–770 | White |
| Example 45 | Compound 41 | Bisphenol S | 730 | 675–775 | Pale grayish white |
| Example 46 | Compound 41 | Tamanol P | 720 | 690–750 | White |
| Example 47 | Compound 57 | Bisphenol A | 720 | 655–765 | Pale greenish |

TABLE 3-continued

| | Phthalide Compound No. | Electron-accepting compound | Absorption characteristics | | Color, by visual observation |
|---|---|---|---|---|---|
| | | | Maximum absorption wavelength (nm) | The region of ≧80% absorbance relative to maximum absorption (nm) | |
| | | | | | white |
| Example 48 | Compound 57 | D-8 | 720 | 690–750 | White |
| Example 49 | Compound 57 | AP-5 | 720 | 690–755 | White |
| Example 50 | Compound 57 | TG-SA | 720 | 660–770 | Pale green |
| Example 51 | Compound 57 | PHB | 720 | 690–760 | White |
| Example 52 | Compound 57 | Tamanol P | 720 | 695–740 | White |
| Example 53 | Compound 57 | Hitanol 1501 | 720 | 695–740 | White |
| Example 54 | Compound 70 | Bisphenol A | 730 | 695–775 | White |
| Example 55 | Compound 70 | D-8 | 720 | 695–760 | White |
| Example 56 | Compound 70 | AP-5 | 725 | 695–765 | White |
| Example 57 | Compound 70 | TG-SA | 725 | 680–790 | Pale yellowish white |
| Example 58 | Compound 70 | PHB | 720 | 695–755 | White |
| Example 59 | Compound 70 | Bisphenol S | 725 | 675–810 | Pale yellowish white |
| Example 60 | Compound 70 | Hitanol 1501 | 725 | 695–760 | White |
| Example 61 | Compound 87 | Bisphenol A | 695 | 640–750 | Pale grayish white |
| Example 62 | Compound 87 | D-8 | 695 | 650–735 | Pale grayish white |
| Example 63 | Compound 87 | PHB | 690 | 630–740 | White |
| Example 64 | Compound 89 | Bisphenol A | 690 | 610–745 | Pale grayish white |
| Example 65 | Compound 89 | D-8 | 685 | 615–730 | Pale grayish white |
| Example 66 | Compound 89 | PHB | 695 | 655–740 | White |
| Example 67 | Compound 91 | Bisphenol A | 725 | 700–760 | White |
| Example 68 | Compound 91 | D-8 | 720 | 690–755 | White |
| Example 69 | Compound 91 | PHB | 725 | 700–755 | White |
| Example 70 | Compound 92 | Bisphenol A | 720 | 665–760 | Pale greenish white |
| Example 71 | Compound 92 | D-8 | 715 | 675–750 | Pale greenish white |
| Example 72 | Compound 92 | PHB | 715 | 685–745 | White |
| Example 73 | Compound 97 | Bisphenol A | 720 | 680–760 | Pale greenish white |
| Example 74 | Compound 97 | D-8 | 720 | 690–750 | White |
| Example 75 | Compound 97 | PHB | 720 | 690–750 | White |
| Example 76 | Compound 98 | Bisphenol A | 720 | 675–765 | Pale grayish white |
| Example 77 | Compound 98 | D-8 | 715 | 680–755 | White |
| Example 78 | Compound 98 | PHB | 715 | 680–760 | White |
| Example 79 | Compound 108 | Bisphenol A | 730 | 695–765 | White |
| Example 80 | Compound 108 | D-8 | 725 | 700–750 | White |
| Example 81 | Compound 108 | PHB | 725 | 700–755 | White |
| Example 82 | Compound 144 | Bisphenol A | 720 | 650–785 | Pale grayish white |
| Example 83 | Compound 144 | D-8 | 715 | 665–770 | Pale grayish white |
| Example 84 | Compound 144 | PHB | 715 | 670–770 | White |
| Example 85 | Compound 155 | Bisphenol A | 740 | 700–780 | Pale green-white |
| Example 86 | Compound 155 | D-8 | 740 | 685–780 | Pale greenish white |
| Example 87 | Compound 155 | PHB | 740 | 705–765 | White |
| Comparison Example 10 | Compound B | Bisphenol A | 730 | 590–780 | Green-blue |
| Comparison Example 11 | Compound B | D-8 | 730 | 570–785 | Green-blue |
| Comparison Example 12 | Compound B | PHB | 730 | 560–790 | Green-blue |

In the table, Tamanol P: p-alkylphenol-formaldehyde resin, Arakawa Chemical Industries, Ltd.; Hitanol 1501: p-alkylphenol-formaldehyde resin, Hitachi Chemical Co., Ltd.

Comparison Example 13

The procedure of Example 18 was repeated except that compound B as synthesized in Comparison Example of Synthesis-2 was used in lieu of 3-[1-(1-ethyl-2-methylindol-3-yl)-1-(4-methylphenyl)ethylen-2-yl ]-3-(4-diethylaminophenyl)phthalide (compound 1) and the quantity of THF was doubled (10 mL). The paper carrying the near infrared absorber thus produced was green-blue with an absorption maximum at 730 nm and a characteristic absorption at 610 nm. The wavelength region corresponding to not less than 80% absorbance relative to the above absorption maximum was 675 nm–770 nm and the region corresponding to not less than 50% absorbance relative to said absorption maximum was 565 nm–790 nm. The reflection spectrum of this paper (a sheet of paper coated with the product of reaction between compound B and bisphenol A) is presented in FIG. 32.

Example 88

Production of a secret ink

A secret ink was produced by dissolving 10 mg of 3-[1-(1-ethyl-2-methylindol-3-yl)-1-(4-methylphenyl)ethylen-2-yl]-3-(4-diethylaminophenyl)phthalide (compound 1) and 20 mg of bisphenol A in an acrylic varnish (methyl acrylate-methyl methacrylate).

Using this ink and a pen, characters were written on a sheet of paper and dried. The resulting record could not be read with the eye but could be read with the OCR.

Examples 89–103

Production of a secret ink

The procedure of Example 88 was repeated except that the phthalide compounds synthesized in Examples 2–16 were respectively used in lieu of 3-[1-(1-ethyl-2-methylindol-3-yl)-1-(4-methylphenyl)ethylen-2-yl]-3-(4-diethylaminophenyl)phthalide to prepare secret inks and using each ink and a pen, characters were written on sheets of paper. The resulting image records were as satisfactory as the record obtained in Example 88.

Example 104

Production of a pressure-sensitive recording material

In 47 g of KMC-113 (a solvent manufactured by Kureha Chemical Industry Co., Ltd.) was dissolved 3 g of 3-[1-(1-ethyl-2-methylindol-3-yl)-1-(4-methylphenyl)ethylen-2-yl]-3-(4-diethylaminophenyl)phthalide (compound 1) with heating. Separately, 5 g of a system modifier (SM-100, manufactured by Mitsui Toatsu Chemicals, Inc.) was added to 100 g of water and the mixture was adjusted to pH 4 with aqueous sodium hydroxide solution. To this solution was added the solution prepared above together with 10 g of melamineformaldehyde precondensate (UMC-300, manufactured by Mitsui Toatsu Chemicals, Inc.) and the mixture was emulsified with a homo-mixer until the size of oil droplets reached 4 microns. The emulsion was heated to 60° C. with stirring and further stirred at this temperature for 1 hour. After cooling to ambient temperature, the emulsion was adjusted to pH 7.5 with 25% aqueous ammonia to provide a microencapsulated color former dispersion.

Ten (10) grams of the microcapsule dispersion thus obtained was mixed thoroughly with 2 g of wheat starch and 1 g of latex and the composition was coated in a coverage of 5 g (solids)/m² on a sheet of wood-free paper weighing 50 g/m² to provide a CB sheet.

The CB sheet thus prepared was superimposed on a CF sheet having a zinc-modified p-octylphenol-formaldehyde resin coating with the coated sides in contact and typed with a typewriter. As a result, no detectable color change was found on the CF sheet. When the absorption characteristics of the recorded image were determined with a UV spectrometer, it absorbed strongly the near infrared region with an absorption maximum at 720 nm and no appreciable absorption was found in the visible region. Characteristically this recorded image could hardly be recognized by the eye but could be read with the OCR. The absorption characteristics of the recorded image are shown in Table 4.

Examples 105–118

Production of pressure-sensitive recording materials

The procedure of Example 104 was repeated except that the phthalide compounds listed below in Table 4 were respectively used in lieu of 3-[1-(1-ethyl-2-methylindol-3-yl)-1-(4-methylphenyl)ethylen-2-yl]-3-(4-diethylaminophenyl)phthalide (compound 1) to provide white CB sheets, which were then placed on CF sheets, respectively, and typed with a typewriter. Like the image obtained in Example 104, there was no apparent change in the color of the CF sheets and characteristically the images could hardly be identified by the eye but could be read with the OCR. The absorption characteristics of the respective recorded images are shown in Table 4.

Comparison Example 14

Production of a pressure-sensitive recording material

The procedure of Example 104 was repeated except that compound A as synthesized in Comparison Example of Synthesis-1 was used in lieu of 3-[1-(1-ethyl-2-methylindol-3-yl)-1-(4-methylphenyl)ethylen-2-yl]-3-(4-diethylaminophenyl)phthalide (compound 1) to provide a CB sheet, which was then superimposed on a CF sheet and typed. The recorded image obtained using compound A assumed a distinct green-blue color. The absorption characteristics of this recorded image are presented in Table 4.

Comparison Example 15

Production of a pressure-sensitive recording material

The procedure of Example 104 was repeated except that compound B as synthesized in Comparison Example of Synthesis-2 was used in lieu of 3-[1-(1-ethyl-2-methylindol-3-yl)-1-(4-methylphenyl)ethylen-2-yl]-3-(4-diethylaminophenyl)phthalide (compound 1) to provide a CB sheet, which was then superimposed on a CF sheet and typed. The recorded image obtained using compound B had a distinct green-blue color. The absorption characteristics of this recorded image are presented in Table 4.

TABLE 4

| | | Absorption characteristics of the recorded image on CF sheet[1] | |
|---|---|---|---|
| | Phthalide compound No. | Maximum absorption wavelength (nm) | The region of ≧80% absorbance relative to max imum absorption (nm) |
| Example 104 | Compound 1 | 720 | 695–765 |
| Example 105 | Compound 13 | 725 | 690–755 |
| Example 106 | Compound 23 | 725 | 695–765 |
| Example 107 | Compound 41 | 725 | 695–755 |
| Example 108 | Compound 57 | 725 | 700–755 |
| Example 109 | Compound 70 | 735 | 705–775 |
| Example 110 | Compound 87 | 710 | 680–755 |
| Example 111 | Compound 89 | 705 | 660–760 |
| Example 112 | Compound 91 | 720 | 700–755 |
| Example 113 | Compound 92 | 720 | 790–750 |
| Example 114 | Compound 97 | 720 | 695–770 |
| Example 115 | Compound 98 | 720 | 690–760 |
| Example 116 | Compound 108 | 730 | 705–760 |
| Example 117 | Compound 144 | 725 | 680–785 |

TABLE 4-continued

| | Phthalide compound No. | Absorption characteristics of the recorded image on CF sheet[1] | |
|---|---|---|---|
| | | Maximum absorption wavelength (nm) | The region of ≧80% absorbance relative to maximum absorption (nm) |
| Example 118 | Compound 155 | 745 | 725–765 |
| Comparison Example 14 | Compound A | 745 | 590–795 |
| Comparison Example 15 | Compound B | 735 | 590–785 |

[1])CF sheet: zinc-modified p-octylphenol-formaldehyde resin

Example 119

Production of a pressure-sensitive recording material

In 47 g of KMC-113 were dissolved 1.5 g of 3-[1-(1-ethyl-2-methylindol-3-yl)-1-(4-methylphenyl)ethylen-2-yl]-3-(4-diethylaminophenyl)phthalide (compound 1) and 1.5 g of 2-anilino-3-methyl-6-diethylaminofluorane with heating. On the other hand, 5 g of a system modifier (SM-100) was added to 100 g of water and the mixture was adjusted to pH 4 with aqueous sodium hydroxide solution. To this were added the solution prepared above and 10 g of melamine-formaldehyde precondensate (UMC-300) and the mixture was emulsified with a homo-mixer until the size of oil droplets became 4 microns. This emulsion was heated to 60° C. with stirring and further stirred for 1 hour. After cooling to ambient temperature, the emulsion was adjusted to pH 7.5 with 25% aqueous ammonia to provide a micro-encapsulated color former dispersion.

Ten (10) grams of the microcapsule dispersion was mixed with 2 g of wheat starch and 1 g of latex and the composition was coated in a coverage of 5 g solids/m$^2$ on a sheet of wood-free paper weighing 50 g/m$^2$ to provide a CB sheet.

The CB sheet thus prepared was superimposed on a CF sheet coated with zinc-modified p-octylphenol-form-aldehyde resin with the coated sides in contact with each other and typed with a typewriter, whereupon a distinct black image was recorded on the CF sheet. This recorded image could be read with the OCR.

Examples 120–134

Production of pressure-sensitive recording materials

The procedure of Example 119 was repeated except that the phthalide compounds listed below in Table 5 were respectively used in lieu of 3-[1-(1-ethyl-2-methylindol-3-yl)-1-(4-methylphenyl)ethylen-2-yl]-3-(4-diethylaminophenyl)phthalide and the fluorane compounds mentioned in Table 5 were respectively used in lieu of 2-anilino-3-methyl-6-diethylaminofluorane to provide white CB sheets. Each of the CB sheets was placed on a CF sheet and typed with a typewriter. The recorded images thus obtained were invariably distinct black and could be read with the OCR.

TABLE 5

| | Fluorane compound | Phthalide compound No. |
|---|---|---|
| Example 120 | 2-Anilino-3-methyl-6-(N-ethyl-N-isobutylamino)fluorane | Compound 1 |
| Example 121 | 2-Anilino-3-methyl-6-(N-ethyl-N-isopentylamino)fluorane | Compound 1 |
| Example 122 | 2-(2,4-Dimethylanilino)-3-methyl-6-diethylaminofluorane | Compound 13 |
| Example 123 | 2-(2,6-Diethylanilino)-3-methyl-6-diethylaminofluorane | Compound 13 |
| Example 124 | 2-(2,6-Dimethylanilino)-3-methyl-6-diethylaminofluorane | Compound 41 |
| Example 125 | 2-(3-Methylanilino)-3-methyl-6-diethylaminofluorane | Compound 57 |
| Example 126 | 2-(2,4-Dimethylanilino)-3-methyl-6-diethylaminofluorane | Compound 57 |
| Example 127 | 2-Anilino-3-methyl-6-(N-methyl-N-cyclohexylamino)fluorane | Compound 70 |
| Example 128 | 2-Anilino-3-chloro-6-diethylaminofluorane | Compound 70 |
| Example 129 | 2-Anilino-3-methyl-6-(N-ethyl-N-isobutylamino)fluorane | Compound 89 |
| Example 130 | 2-(2,4-Dimethylanilino)-3-methyl-6-diethylaminofluorane | Compound 92 |
| Example 131 | 2-(2,6-Dimethylanilino)-3-methyl-6-diethylaminofluorane | Compound 97 |
| Example 132 | 2-(2,4-Dimethylanilino)-3-methyl-6-diethylaminofluorane | Compound 98 |
| Example 133 | 2-Anilino-3-chloro-6-diethylaminofluorane | Compound 108 |
| Example 134 | 2-Anilino-3-methyl-6-(N-ethyl-N-tetrahydrofurfurylamino)fluorane | Compound 144 |

Example 135

Production of a thermo-sensitive recording material

Using a sandmill, 5.0 g of 3-[1-(1-ethyl-2-methylindol-3-yl)-1-(4-methylphenyl)ethylen-2-yl]-3-(4-diethylaminophenyl)phthalide (compound 1) was pulverized in the presence of 45 g of 2.5% aqueous poly(vinyl alcohol) solution until a mean particle size of 1 μm was attained to provide a dispersion.

On the other hand, 10 g of bisphenol A and 10 g of p-benzylbiphenyl were pulverized in the presence of 80 g of 2.5% aqueous polyvinyl alcohol solution in a sandmill until a mean particle size of 1 μm was attained to provide a dispersion.

The two dispersions prepared above were thoroughly blended with 30 g of 50% calcium carbonate dispersion and 15 g of 30% paraffin wax dispersion to provide a thermo-sensitive coating.

This thermo-sensitive coating was coated in a coverage of 5 g (solids)/m$^2$ on a sheet of wood-free paper weighing 50 g/m$^2$, dried and calendered until the Bekk smoothness value of the thermo-sensitive recording layer being 200 seconds to provide a white thermo-sensitive recording material.

Using a TH-PMD printer (manufactured by Ohkura Electric Machinery Co., Ltd.), the above thermo-sensitive recording material was developed at a pulse width of 1.15 ms and the optical density (OD value) of the image was measured on Macbeth RD-914 (filter: Visual). The absorption characteristics of the image thus obtained were also determined on Spectrophotometer UV365 (manufactured by Shimadzu Corporation). The results are shown in Table 6. This image record could hardly be read with the eye but could be read with the OCR.

Examples 136–146

Production of thermo-sensitive recording materials

The procedure of Example 135 was repeated except that the phthalide compounds listed below in Table 6 were respectively used in lieu of 3-[1-(1-ethyl-2-methylindol-3- yl)-1-(4-methylphenyl)ethylen-2-yl]-3-(4-diethylaminophenyl)phthalide (compound 1) to provide white thermo-sensitive recording materials, which were then tested as in Example 135. The results are presented in Table 6.

The image records obtained were hardly legible to the eye but could be read with the OCR.

Comparison Example 16

Production of a thermo-sensitive recording material

The procedure of Example 135 was repeated except that compound A as produced in Comparison Example of Synthesis-1 was used in lieu of 3-[1-(1-ethyl-2-methylindol-3-yl)-1-(4-methylphenyl)ethylen-2-yl]-3-(4-diethylaminophenyl)phthalide (compound 1) to provide a white thermo-sensitive recording material, which was then tested as in Example 135. The results are presented in Table 6.

This image record was green-blue.

Comparison Example 17

Production of a thermo-sensitive recording material

The procedure of Example 135 was repeated except that compound B as synthesized in Comparison Example of Synthesis-2 was used in lieu of 3-[1-(1-ethyl-2-methylindol-3-yl)-1-(4-methylphenyl)ethylen-2-yl]-3-(4-diethylaminophenyl)phthalide (compound 1) to provide a white thermo-sensitive recording material, which was then tested as in Example 135. The results are presented in Table 6.

This recorded image was green-blue.

TABLE 6

| | Phthalide compound No. | Developed color image density (OD) | Maximum absorption wavelength (nm) | Absorption characteristics of the recorded image: The region of ≧80% absorbance relative to maximum absorption (nm) |
|---|---|---|---|---|
| Example 135 | Compound 1 | 0.13 | 725 | 690–760 |
| Example 136 | Compound 13 | 0.10 | 720 | 695–750 |
| Example 137 | Compound 70 | 0.07 | 725 | 695–765 |
| Example 138 | Compound 87 | 0.24 | 695 | 640–750 |
| Example 139 | Compound 89 | 0.28 | 690 | 615–745 |
| Example 140 | Compound 91 | 0.08 | 725 | 695–760 |
| Example 141 | Compound 92 | 0.14 | 725 | 690–760 |
| Example 142 | Compound 97 | 0.12 | 720 | 675–765 |
| Example 143 | Compound 98 | 0.14 | 720 | 680–765 |
| Example 144 | Compound 108 | 0.12 | 730 | 695–765 |
| Example 145 | Compound 144 | 0.28 | 720 | 645–785 |
| Example 146 | Compound 155 | 0.27 | 740 | 695–780 |
| Comparison Example 16 | Compound A | 0.55 | 740 | 575–795 |
| Comparison Example 17 | Compound B | 0.57 | 730 | 590–780 |

Example 147

Production of a thermo-sensitive recording material

Using a sandmill, 2.5 g of 3-[1-(1-ethyl-2-methylindol-3-yl)-1-(4-methylphenyl)ethylen-2-yl]-3-(4-diethylaminophenyl)phthalide (compound 1) and 2.5 g of 2-anilino-3-methyl-6-di-n-butylaminofluorane were pulverized in the presence of 45 g of 2.5% aqueous poly(vinyl alcohol) solution until a mean particle size of 1μ was attained to provide a dispersion.

On the other hand, 10 g of bisphenol A and 10 g of p-benzylbiphenyl were comminuted in the presence of 80 g of 2.5% aqueous poly(vinyl alcohol) solution until a mean particle size of 1 μm was attained to provide a dispersion.

The two dispersions prepared above were thoroughly blended with 30 g of 50% calcium carbonate dispersion and 15 g of 30% paraffin wax dispersion to prepare a thermo-sensitive coating. This thermo-sensitive coating was coated in a coverage of 5 g (solids)/$m^2$ on a sheet of wood-free paper weighing 50 g/$m^2$, dried and calendered until the Bekk smoothness of the thermo-sensitive recording layer being 200 seconds to provide a white thermo-sensitive recoding layer.

When this heat-responsive recording material was typed with the TH-PMD printer, a black recorded image was obtained. This image could be read with the OCR.

Examples 148–165

Production of thermo-sensitive recording materials

The procedure of Example 147 was repeated except that the phthalide compounds listed below in Table 7 were respectively used in lieu of 3-[1-(1-ethyl-2-methylindol-3-yl)-1-(4-methylphenyl)ethylen-2-yl]-3-(4-diethylaminophenyl)phthalide (compound 1) and the fluorane compounds listed in Table 7 were respectively used in lieu of 2-anilino-3-methyl-6-di-n-butylaminofluorane to provide white thermo-sensitive recording materials, which were then typed with the TH-PMD printer.

The recorded images thus obtained were distinct black and could be read with the OCR.

TABLE 7

| | Fluorane compound | Phthalide Compound No. |
|---|---|---|
| Example 148 | 2-Anilino-3-methyl-6-(N-ethyl-N-isobutylamino)fluorane | Compound 1 |
| Example 149 | 2-Anilino-3-methyl-6-(N-ethyl-N-isopentylamino)fluorane | Compound 1 |
| Example 150 | 2-(2,4-Dimethylanilino)-3-methyl-6-diethylaminofluorane | Compound 1 |
| Example 151 | 2-(2,6-Diethylanilino)-3-methyl-6-diethylaminofluorane | Compound 13 |
| Example 152 | 2-(2,6-Dimethylanilino)-3-methyl-6-diethylaminofluorane | Compound 13 |
| Example 153 | 2-(3-Methylanilino)-3-methyl-6-diethylaminofluorane | Compound 13 |
| Example 154 | 2-(2,4-Dimethylanilino)-3-methyl-6-diethylaminofluorane | Compound 57 |
| Example 155 | 2-Anilinl-3-methyl-6-(N-methyl-N-cyclohexylamino)fluorane | Compound 57 |
| Example 156 | 2-Anilino-3-chloro-6-diethylaminofluorane | Compound 57 |
| Example 157 | 2-Anilino-3-methyl-6-(N-ethyl-N-isobutylamino)fluorane | Compound 87 |
| Example 158 | 2-Anilino-3-methyl-6-(N-ethyl-N-isopentylamino)fluorane | Compound 89 |
| Example 159 | 2-Anilino-3-methyl-6-di-n-pentylaminofluorane | Compound 91 |
| Example 160 | 2-(3-Methylanilino)-3-methyl-6-diethylaminofluorane | Compound 92 |
| Example 161 | 2-(3-Methylanilino)-3-methyl-6-di-n-butylaminofluorane | Compound 97 |
| Example 162 | 2-Anilino-3-methyl-6-(N-methyl-N-n-propylamino)fluorane | Compound 98 |
| Example 163 | 2-Anilino-3-methyl-6-(n-ethyl-N-ethoxypropylamino)fluorane | Compound 108 |
| Example 164 | 2-(2-Chloroanilino)-6-diethylaminofluorane | Compound 144 |
| Example 165 | 2-(2-Chloroanilino)-6-(di-n-butylamino)fluorane | Compound 155 |

EFFECT OF THE INVENTION

The near infrared absorber employing the phthalide compound of this invention and the recorded image obtainable with the recording material of this invention absorb strongly the near infrared region but only slightly the visible region. Therefore, the near infrared absorber of this invention is either colorless or pale in color to the eye but has a large capacity to absorb near infrared radiation and the recorded image obtainable with the recording material of this invention is hardly legible to the eye but can be read with an OCR. Moreover, in the recording material employing the phthalide compound of this invention in combination with other conventional color formers, the influence of the compound on the color of the other color formers is minimal.

What is claimed is:

1. A phthalide compound of general formula (I)

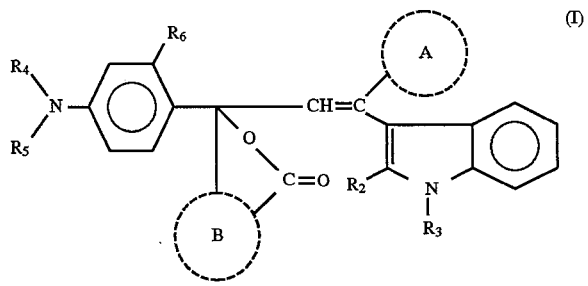

wherein ring A represents a substituent group of the following structural formula

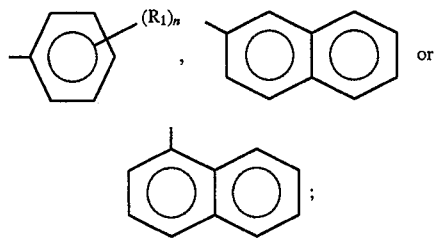

where $R_1$ represents hydrogen, alkyl, alkoxy or halogen; n represents an integer of 1–3, inclusive;

ring B represents a substituent group of the following structural formula

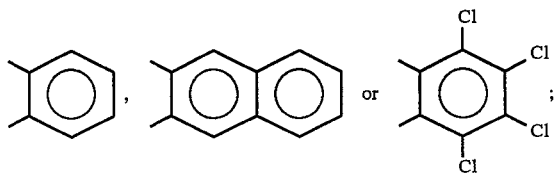

where $R_2$ represents alkyl or aryl; $R_3$ represents alkyl; $R_4$ and $R_5$ independently represent alkyl or unsubstituted or substituted phenyl wherein the substituent on said phenyl is selected from the group consisting of alkyl, alkoxy and halogen; and $R_6$ represents hydrogen, alkyl or alkoxy.

2. The phthalide compound according to claim 1 wherein $R_1$ on ring A represents hydrogen, $C_{1-8}$ alkyl, $C_{1-4}$ alkoxy or halogen.

3. The phthalide compound according to claim 1 wherein $R_2$ represents $C_{1-4}$ alkyl or unsubstituted or substituted phenyl wherein the substituent on said phenyl is selected from the group consisting of alkyl and halogen.

4. The phthalide compound according to claim 1 wherein $R_3$ is $C_{1-12}$ alkyl.

5. The phthalide compound according to claim 1 wherein $R_4$ and $R_5$ independently represent $C_{1-8}$ alkyl or unsubstituted or substituted phenyl wherein the substituent on said phenyl is selected from the group consisting of alkyl, alkoxy and halogen.

6. The phthalide compound according to claim 1 wherein $R_6$ represents hydrogen, $C_{1-4}$ alkyl or $C_{1-8}$ alkoxy.

7. A near infrared absorber which is obtained by reacting a phthalide compound of general formula (I) in claim 1 with one or more developer under reaction conditions which allow an electron transfer reaction between said phthalide compound and said developer.

8. The near infrared absorber according to claim 7 wherein said developer is one or more compounds selected from the group consisting of phenol derivative, acidic polymer or its metal modification product, and organic carboxylic acid or its metal salt.

9. The near infrared absorber according to claim 8 wherein said phenol derivative is bisphenol A, bisphenol S, benzyl p-hydroxybenzoate, 2,2-bis(p-hydroxyphenyl)-4-methylpentane, 3,3'-diallyl-4,4'-dihydroxydiphenyl sulfone, 4-hydroxy-4'-isopropoxydiphenyl sulfone, 3,4-dihydroxy-4'-methyldiphenyl sulfone, or 1,7-bis(4-hydroxyphenylthio)-3,5-dioxaheptane.

10. The near infrared absorber according to claim 8 wherein said acidic polymer or metal modification product thereof is zinc-modified p-octylphenol resin, p-phenylphenol resin or alkylphenol resin.

11. The near infrared absorber according to claim 8 wherein said organic carboxylic acid or metal salt thereof is a salicylic acid derivative.

12. A near infrared absorbing composition containing the near infrared absorber claimed in claim 7.

13. A secret ink composition comprising a phthalide compound of general formula (I) as claimed in claim 1 and an electron-accepting compound.

14. A recording material utilizing the reaction of an electron-donating color former with an electron-accepting developer, wherein said recording material comprises a phthalide compound as claimed in claim 1 as the electron-donating color former.

15. A recording material utilizing the reaction of an electron-donating color former with an electron-accepting developer, wherein said recording material comprises a phthalide compound as claimed in claim 1 as the electron-donating color former, wherein one or more species of the phthalide compound claimed in claim 1 as the electron-donating color former are used in combination with one or more species of the fluorane compound of general formula (IV)

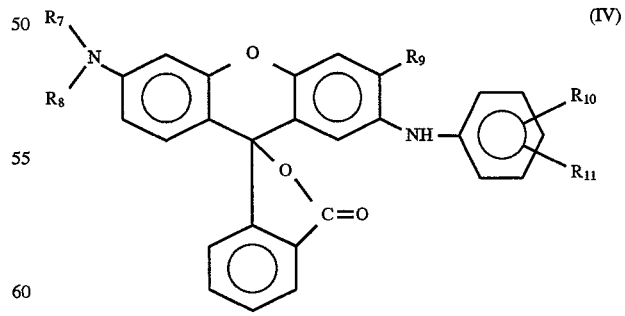

wherein $R_7$ and $R_8$ independently represent alkyl, alkoxyalkyl, cycloalkyl, aryl or tetrahydrofurfuryl; $R_9$ represents hydrogen, methyl or chlorine; $R_{10}$ and $R_{11}$ independently represent hydrogen, alkyl, chlorine or fluorine; $R_7$ and $R_8$ may, taken together with the adjacent nitrogen atom, form a heterocyclic group.

16. The recording material according to claim 14 which is a pressure-sensitive recording material.

17. The recording material according to claim 14 which is a thermo-sensitive recording material.

18. A process for producing a phthalide compound of claim 1 which comprises reacting an ethylene compound of general formula (II) with a benzoic acid derivative of general formula (III) in the presence of a dehydrative condensing agent.

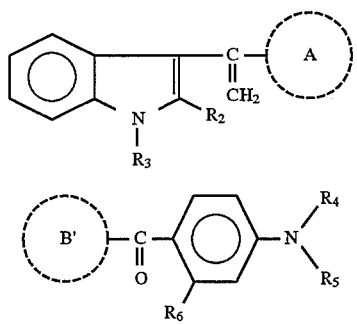

wherein ring A, $R_2$, $R_3$, $R_4$, $R_5$ and $R_6$ are respectively as defined in claim 1; and ring B' represents a substituent group of the following structural formula

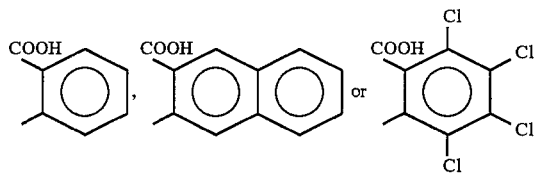

19. A near infrared absorbing composition comprising the near infrared absorber of claim 7 and a binder or vehicle for said absorber.

* * * * *